United States Patent
Thaning et al.

(10) Patent No.: US 10,730,897 B2
(45) Date of Patent: Aug. 4, 2020

(54) MANGANESE CHELATE COMPOUNDS

(71) Applicant: GE HEALTHCARE AS, Oslo (NO)

(72) Inventors: Mikkel Jacob Thaning, Oslo (NO); Andreas Richard Meijer, Oslo (NO); Brian Christopher Bales, Niskayuna, NY (US); Michael James Rishel, Niskayuna, NY (US)

(73) Assignee: GE HEALTHCARE AS, Oslo (NO)

( * ) Notice: Subject to any disclaimer, the term of this patent is extended or adjusted under 35 U.S.C. 154(b) by 0 days.

(21) Appl. No.: 16/472,579

(22) PCT Filed: Dec. 21, 2017

(86) PCT No.: PCT/EP2017/084148
§ 371 (c)(1),
(2) Date: Jun. 21, 2019

(87) PCT Pub. No.: WO2018/115314
PCT Pub. Date: Jun. 28, 2018

(65) Prior Publication Data
US 2020/0062791 A1  Feb. 27, 2020

Related U.S. Application Data

(60) Provisional application No. 62/437,082, filed on Dec. 21, 2016.

(51) Int. Cl.
*C07F 13/00* (2006.01)
(52) U.S. Cl.
CPC .................................. *C07F 13/005* (2013.01)

(58) Field of Classification Search
None
See application file for complete search history.

(56) References Cited

FOREIGN PATENT DOCUMENTS

| WO | 2007042506 A1 | 4/2007 |
| WO | 2011073371 A1 | 6/2011 |

OTHER PUBLICATIONS

European Notice of Allowance corresponding to European Application No. 17822298.0, dated Dec. 3, 2019.
International Search Report and Written Opinion corresponding to International Application No. PCT/EP2017/084148, dated Mar. 22, 2018.
Wen, Jinghan, et al., "A mononuclear Mn2+complex based on a novel tris-(ethyl acetate) pendant-armed tetraazamacrocycle: Effect of pyridine on self-assembly and weak interactions" Inorganic Chemistry Communications, vol. 21, Mar. 30, 2012, pp. 16-20.
Pan, Dipanjan, et al., "Manganese-based MRI contrast agents: past, present, and future", Tetrahedron, vol. 67, No. 44, 2011, pp. 8431-8444.
Gale, Eric M., et al., "A Manganese Alternative to Gadolinium for MRI Contrast", Journal of the American Chemical Society, vol. 137. No. 49, Dec. 16, 2015, pp. 15548-15557.

*Primary Examiner* — Clinton A Brooks
(74) *Attorney, Agent, or Firm* — Culhane Meadows PLLC; Jeff B. Vockrodt

(57) ABSTRACT

The invention provides compounds suitable for use as contrast agents in magnetic resonance imaging (MRI). The compounds of the present invention are manganese (II) complexes having advantageous properties as compared with similar known compounds.

29 Claims, No Drawings

MANGANESE CHELATE COMPOUNDS

CROSS-REFERENCE TO RELATED APPLICATIONS

This application is a filing under 35 U.S.C. 371 of international application number PCT/EP2017/084148, filed Dec. 21, 2017, which claims priority to application number U.S. Provisional Application No. 62/437,082 filed on Dec. 21, 2016, the entire disclosures of each of which are hereby incorporated by reference.

TECHNICAL FIELD OF THE INVENTION

The invention relates to chelate compounds and their use as contrast agents in magnetic resonance procedures.

DESCRIPTION OF RELATED ART

Magnetic resonance imaging (MRI) is a medical imaging technique in which areas of the body are visualised via the nuclei of selected atoms, especially hydrogen nuclei. The MRI signal depends upon the environment surrounding the visualised nuclei and their longitudinal and transverse relaxation times, T1 and T2. Thus, in the case when the visualised nucleus is a proton, the MRI signal intensity will depend upon factors such as proton density and the chemical environment of the protons. Contrast agents can be used in MRI to improve the imaging contrast. They work by effecting the T1, T2 and/or T2* relaxation time and thereby influence the contrast in the images.

It is known that the T1, T2 and/or T2* relaxation times can be optimized for a chelated paramagnetic contrast agents by structural modification. Of particular importance is the presence and residence time of a water molecule bound to the paramagnetic ion and the rotational correlation time of the contrast agent.

The presence and residence time of a water molecule, bound to the paramagnetic ion, can be modulated by the choice of paramagnetic ion and the chelating moiety. The rotational correlation time can be modulated by varying the size of the contrast agent.

It is also known that the paramagnetic ion can interfere with biological pathways and induce toxicity, so that the paramagnetic ion needs to be retained as far as possible within a chelate. The ability of a chelate to retain the paramagnetic ion, from now on denoted as stability, is also a property that can be modulated by structural design of the cheland moiety. Of particular interest is the kinetic stability, measured as a dissociation half-life, which indicates the degree of inertia towards altered chemical surroundings (i.e. endogenous ions).

Several types of contrast agents are known for use in MRI. Blood pool MR contrast agents, for instance superparamagnetic iron oxide particles, are retained within the vasculature for a prolonged time. They have proven extremely useful to enhance contrast e.g. in the liver but also to detect capillary permeability abnormalities such as "leaky" capillary walls in tumours which are a result of tumour angiogenesis.

The solubility of the paramagnetic chelate in water is also an important factor when they are used as contrast agents for MRI because they are administered to patients in relatively large doses. A highly water-soluble paramagnetic chelate requires a lower injection volume, is thus easier to administer to a patient and causes less discomfort. Water-soluble paramagnetic chelates, i.e. complexes of a chelator and a paramagnetic metal ion are well known—for instance the commercially-available gadolinium chelates Omniscan™ (GE Healthcare), Dotarem™ (Guerbet), Gadavist™ (Bayer) and Magnevist™ (Bayer). Because of their low molecular weight they rapidly distribute into the extracellular space (i.e. the blood and the interstitium) when administered into the vasculature. They are also cleared relatively rapidly from the body. U.S. Pat. No. 8,540,966 teaches the following generalised structure:

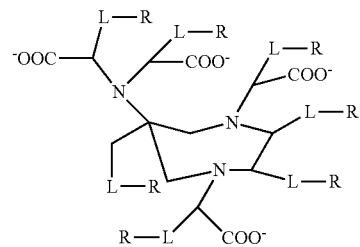

Where L is a linker and R is H or a $C_{2-70}$ aminopolyol moiety. The experimental examples of U.S. Pat. No. 8,540,966 compare certain commercially-available gadolinium chelates with gadolinium chelates of the invention to demonstrate a pharmacokinetic profiled similar to the commercially-available gadolinium chelates but with higher relaxivity. U.S. Pat. No. 8,540,966 does not describe any effect of the aminopolyol moieties on transmetallation inertness.

EP1931673 teaches the following generalised structure:

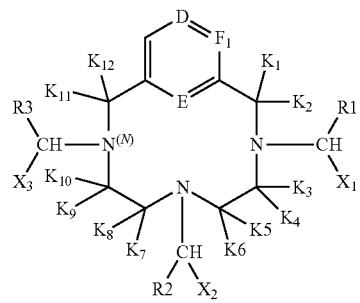

Each R in the above structure is defined in EP1931673 as a co-ordinating ligand and each X comprises at least one $C_{1-6}$ hydroxyalkyl group. EP1931673 emphasises the relaxivity properties of the compounds taught therein. The teachings of EP1931673 note that the above compound may be complexed with a paramagnetic metal ion selected from $Gd^{3+}$, $Mn^{2+}$ and $Fe^{3+}$ but in reality the focus is on chelate structures that are suitable for stable complexation of $Gd^{3+}$ e.g. the following gadolinium-containing complex:

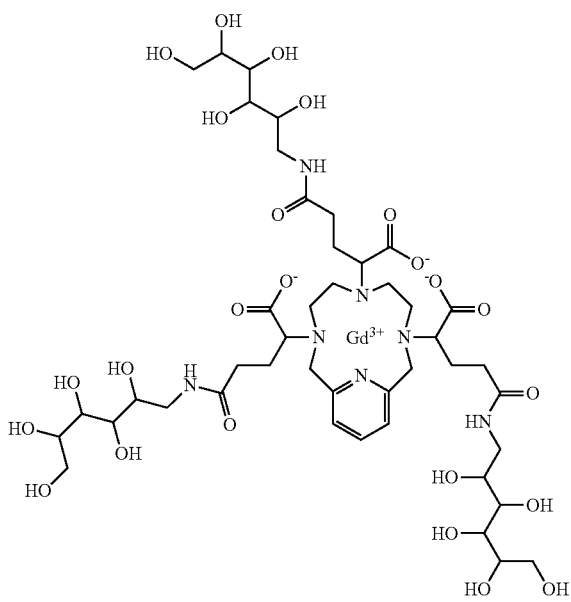

All the exemplified complexes are heptadentate, as four nitrogens and three carboxylic acid groups are coordinating to the complexated metal ion. The detrimental effect of heptadentate manganese chelates has been described in WO2011073371. EP1931673 does not describe any effect of the hydroxyalkyl moieties on transmetallation inertness.

As can be appreciated from the commercially-available agents and the focus of the prior art, gadolinium is the most widely used paramagnetic metal ion for MRI chelates.

The manganese(II) ion is a paramagnetic species with a high spin number and a long electronic relaxation time and the potential of a manganese(II) based high relaxivity contrast agent has been reported in the literature (Tóth, E; Advances in Inorganic Chemistry, 2009, 61(09), 63-129). However, manganese(II) chelates have proved to be much less stable compared to corresponding gadolinium chelates. For example, the manganese chelate of DOTA (MnDOTA) is several hundred times less stable compared to the corresponding gadolinium complex (GdDOTA (Drahos, B; Inorganic Chemistry, 2012(12), 1975-1986).

An important problem to be solved is thus that of obtaining novel manganese chelates exhibiting a high stability while maintaining efficacious relaxation properties.

Certain stable manganese chelates are described in WO2011073371. The molecular design described therein has been demonstrated to favour high chelate stability and a high relaxivity. This makes these compounds very suitable for use as MRI contrast agents. An exemplary compound of WO2011073371 has the following structure:

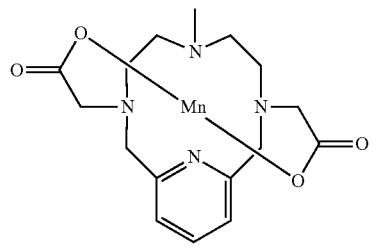

However, there is still scope for further improvements in terms of stability and relaxivity.

SUMMARY OF THE INVENTION

In one aspect the present invention relates to a compound of Formula I or a salt or solvate thereof:

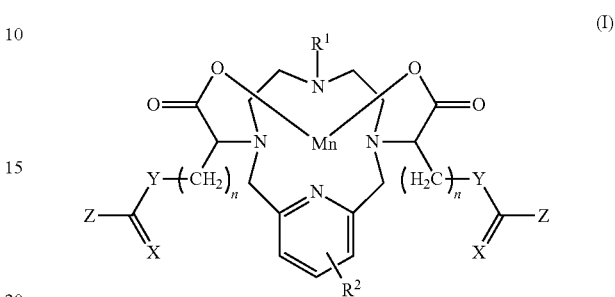

wherein:

X is O or S;

Y is O, S or Q-$R^3$ where Q is N or CH and $R^3$ is selected from the group comprising $C_{1-20}$ hydroxyalkyl, $C_{1-6}$ alkyl or hydrogen;

Z is O-L-$R^4$, S-L-$R^4$ or Q-$R^3$-(L-$R^4$) where Q and $R^3$ are as defined for Y and L is an optional linker selected from the groups comprising $C_{1-6}$ alkylene, $C_{1-6}$ hydroxyalkylene and a PEG linker, $R^4$ is selected from the group comprising $C_{1-6}$ alkyl-$R^5$, $C_{3-6}$ aryl-$R^5$, hydroxy, —O—$C_{1-3}$ alkyl-$R^5$, sulfonyl, a 5-6-membered heterocyclic ring, a carbohydrate moiety, a chelate moiety, an amino acid moiety, wherein $R^5$ represents one or more optional substituents selected from hydroxy, amino, oxo, halo, $C_{1-3}$ alkyl, sulfonamide or —C(═O)—NH—$C_{1-6}$ hydroxyalkyl; or Z itself forms part of a carbohydrate moiety or a 5-6-membered heterocyclic ring;

$R^1$ is $C_{1-3}$ alkyl or —$(CH_2)_m$—$Y^1$—C(═$X^1$)—$Z^1$ wherein $X^1$, $Y^1$ and $Z^1$ are as defined for X, Y and Z and m is an integer from 2-5;

$R^2$ represents 0-3 substituents independently selected from the group comprising hydroxy, halo, amino, amido, $C_{1-6}$ alkyl and $C_{1-6}$ hydroxyalkyl; and, each n is an integer from 0-15;

wherein the compound of Formula I comprises at least two hydroxy groups; and, with the proviso that when Y is Q-$R^3$ where Q is CH, Z is not Q-$R^3$-(L-$R^4$) where Q is N.

In another aspect the present invention relates to a pharmaceutical composition comprising the compound of Formula I of the invention together with a biocompatible carrier in a form suitable for mammalian administration.

In another aspect the present invention relates to a method comprising:

(i) administration to a subject of the compound of Formula I of the invention or the pharmaceutical composition of the invention;

(ii) detection of magnetic resonance (MR) signals from said subject or parts of said subject in which said compound has distributed;

(iii) generation of MR images and/or MR spectra from said detected signals.

In another aspect the present invention provides the compound of Formula I of the invention for use in the method of the invention.

The manganese(II) based chelates of the present invention are kinetically stable and show advantageous water exchange kinetics, and can be used as MRI contrast agents.

Although the compounds described in WO2011073371 have been characterized as very stable (i.e. high level of inertness towards transmetalation), the present inventors have surprisingly succeeded in obtaining manganese chelates endowed with an even greater stability. This surprising inertness towards transmetallation is obtained by embedding the manganese chelate within a hydrophilic shield. The hydrophilic shield is constructed by grafting hydrophilic arms to the chelating carboxyl functional groups. Although the advantageous effects of polyhydroxylated chelates on relaxation properties are known from the prior art, the surprising effect on dissociation kinetics demonstrated by the present invention have however not been described previously.

DETAILED DESCRIPTION OF THE PREFERRED EMBODIMENTS

To more clearly and concisely describe and point out the subject matter of the claimed invention, definitions and exemplary embodiments are provided hereinbelow for specific terms used throughout the present specification and claims. Any exemplification of specific terms herein should be considered as a non-limiting example.

The terms "comprisinq" or "comprises" have their conventional meaning throughout this application and imply that the agent or composition must have the essential features or components listed, but that others may be present in addition. The term 'comprisinq' includes as a preferred subset "consistinq essentially of" which means that the composition has the components listed without other features or components being present.

A "salt" according to the invention, include physiologically acceptable acid addition salts such as those derived from mineral acids, for example hydrochloric, hydrobromic, phosphoric, metaphosphoric, nitric and sulphuric acids, and those derived from organic acids, for example tartaric, trifluoroacetic, citric, malic, lactic, fumaric, benzoic, glycollic, gluconic, succinic, methanesulphonic, and para-toluenesulphonic acids.

A suitable "solvate" according to the invention is selected from ethanol, water, saline, physiological buffer and glycol.

The term "alkyl", alone or in combination, means a straight-chain or branched-chain alkyl radical having the general formula $C_nH_{2n+1}$. Examples of such radicals include methyl, ethyl, and isopropyl.

The term "hydroxyl" refers to the group —OH.

The term "hydroxyalkyl" refers to an alkyl group as defined above comprising a hydroxyl substituent as defined above.

The term "aryl" refers to a functional group or substituent derived from an aromatic ring, usually an aromatic hydrocarbon, examples of which include phenyl and pyridyl. In one embodiment aryl groups of the present invention are aromatic 6-membered rings with between 0-3 heteroatoms selected from O, N and S.

The term "halogen" or "halo" means a substituent selected from fluorine, chlorine, bromine or iodine.

The term "carbohydrate moiety" refers to an aldehyde or a ketone derivative of a polyhydric alcohol and includes monosaccharide, disaccharide and oligosaccharide residues. Non-limiting examples include fructose, glucose and sucrose residues.

The term "alkylene" refers to the bivalent group —$(CH_2)_x$— wherein x is an integer from 1-6. The term "hydroxyalkylene" refers to an alkylene comprising one or more hydroxy substituents.

PEG Linker

The term "hydroxy" refers to the group —OH.

The term "sulfonyl" refers to the group —$SO_2$.

The term "amino acid moiety" refers to between 1-3 amino acids.

The term "chelate moiety" refers to a substituent that is a metal chelate where the term "metal chelate" refers to a coordination complex wherein a metal ion is bonded to a surrounding array of molecules or anions comprised in a cheland.

A "cheland" is defined herein as an organic compound capable of forming coordinate bonds with a paramagnetic metal ion through two or more donor atoms. In a typical cheland suitable for the present invention 2-6, and preferably 2-4, metal donor atoms are arranged such that 5- or 6-membered rings result (by having a non-coordinating backbone of either carbon atoms or non-coordinating heteroatoms linking the metal donor atoms). Examples of suitable donor atom types where the metal ion is a paramagnetic metal ion include amines, thiols, amides, oximes, and phosphines. In one embodiment the metal ion is manganese.

The term "amino" refers to the group —NR'R" wherein R' and R" are independently hydrogen or an alkyl.

The term "amido" refers to the group —C(=O)NR'R" wherein R' and R" are as defined for the term amino.

The term "oxo" refers to the group =O.

The term "sulfonamide" refers to the group —$SO_2$—$NH_2$.

In one embodiment of the compound of the present invention X is O, Y is Q-$R^3$ wherein Q is N and Z is Q-$R^3$-(L-$R^4$) wherein Q is N.

In one embodiment of the compound of the present invention X is S, Y is Q-$R^3$ wherein Q is N and Z is Q-$R^3$-(L-$R^4$) wherein Q is N.

In one embodiment of the compound of the present invention X is O, either Y is O or Z is O-L-$R^4$ and when Y is not O it is Q-$R^3$ wherein Q is N and when Z is not O-L-$R^4$ it is Q-$R^3$-(L-$R^4$) wherein Q is N.

In one embodiment of the compound of the present invention X is S, either Y is O or Z is O-L-$R^4$ and when Y is not O it is Q-$R^3$ wherein Q is N and when Z is not O it is Q-$R^3$-(L-$R^4$) wherein Q is N.

In one embodiment of the compound of the present invention X is O, Y is Q-$R^3$ wherein Q is N and Z is Q-$R^3$-(L-$R^4$) wherein Q is CH.

In one embodiment of the compound of the present invention X is O, either Y is O or Z is O-L-$R^4$ and when Y is not O it is Q-$R^3$ wherein Q is CH and when Z is not O it is Q-$R^3$-(L-$R^4$) wherein Q is CH.

In one embodiment of the compound of the present invention each -L-$R^4$ is $C_{1-12}$ hydroxyalkyl.

In one embodiment of the compound of the present invention each -L-$R^4$ is $C_{3-6}$ hydroxyalkyl.

In one embodiment of the compound of the present invention each -L-$R^4$ is $C_6$ hydroxyalkyl.

In one embodiment of the compound of the present invention each -L-$R^4$ is independently selected from the group comprising:

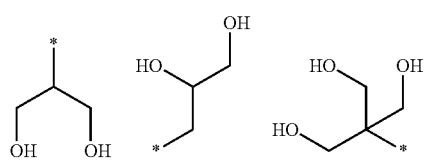

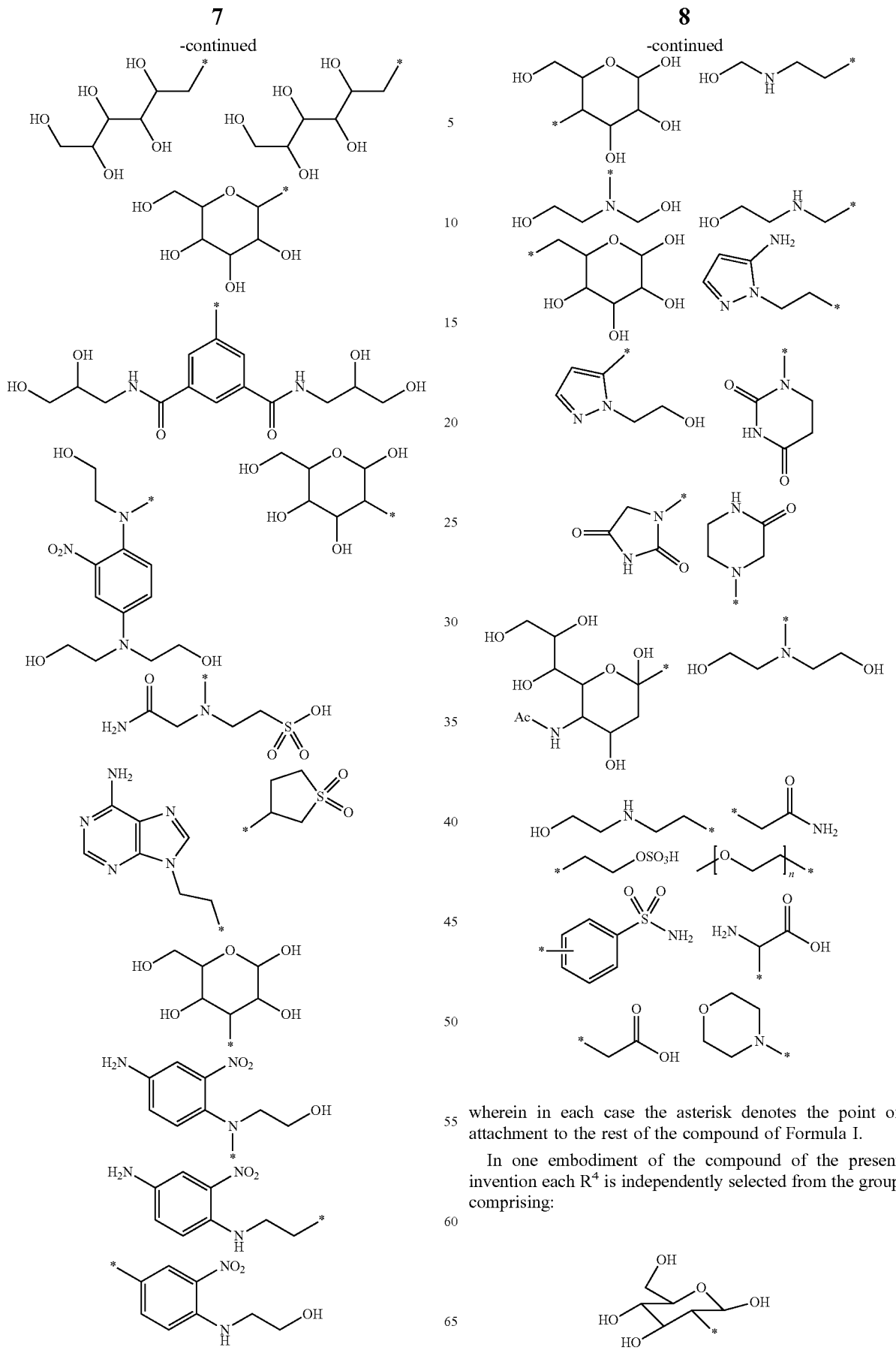
wherein in each case the asterisk denotes the point of attachment to the rest of the compound of Formula I.
In one embodiment of the compound of the present invention each $R^4$ is independently selected from the group comprising:
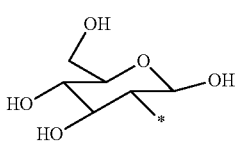

-continued

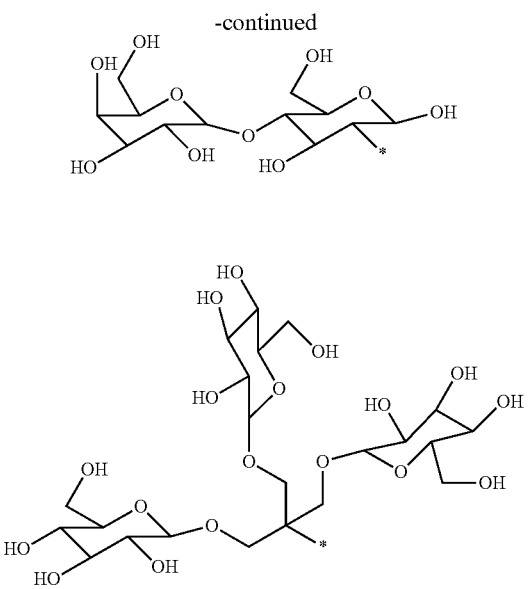

wherein in each case the asterisk denotes the point of attachment to the rest of the compound of Formula I.

In one embodiment of the compound of the present invention each $R^4$ is a $C_{3-6}$ aryl-$R^5$ where $R^5$ is selected from halo and —C(=O)—NH—$C_{1-6}$ hydroxyalkyl.

In one embodiment of the compound of the present invention said halo is iodo.

In one embodiment of the compound of the present invention said $C_{3-6}$ aryl is phenyl.

In one embodiment of the compound of the present invention each $R^4$ is a triiodinated phenyl.

In one embodiment of the compound of the present invention each $R^4$ is:

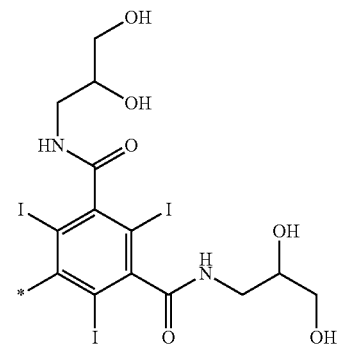 [SMILES: *c1c(I)c(C(=O)NCC(O)CO)c(I)c(C(=O)NCC(O)CO)c1I]

wherein the asterisk denotes the point of attachment to the rest of the compound of Formula I.

In one embodiment of the compound of the present invention each $R^4$ is the same.

In one embodiment of the compound of the present invention each $R^3$ is independently selected from the group comprising $C_{1-3}$ alkyl or hydrogen.

In one embodiment of the compound of the present invention each $R^3$ is $C_{1-3}$ alkyl.

In one embodiment of the compound of the present invention each $R^3$ is methyl.

In one embodiment of the compound of the present invention each $R^3$ is hydrogen.

In one embodiment of the compound of the present invention each $R^3$ is the same.

In one embodiment of the compound of the present invention each n is an integer from 1-6.

In one embodiment of the compound of the present invention each n is 2.

In one embodiment of the compound of the present invention wherein m is 3.

In one embodiment of the compound of the present invention $R^1$ is $C_{1-3}$ alkyl.

In one embodiment of the compound of the present invention $R^1$ is a methyl group.

In one embodiment of the compound of the present invention $R^1$ is —(CH$_2$)$_m$—Y—C(=X)—Z wherein X, Y, Z and m are as defined herein.

In one embodiment of the compound of the present invention $R^2$ represents 0 substituents.

In one embodiment of the compound of the present invention $R^2$ represents 2 hydroxy groups. In one embodiment of the compound of the present invention said hydroxyl groups are at the meta positions on the pyridyl ring.

In one embodiment the compound of the present invention comprises at least 4 hydroxy groups.

In one embodiment the compound of the present invention comprises 4-15 hydroxy groups.

In one embodiment the compound of the present invention comprises 5-10 hydroxy groups.

In one embodiment of the compound of the present invention said Mn is an enriched isotope of Mn selected from the group comprising $^{52}$Mn and $^{54}$Mn.

Non-limiting examples of particular compounds of Formula I of the invention include the following compounds:

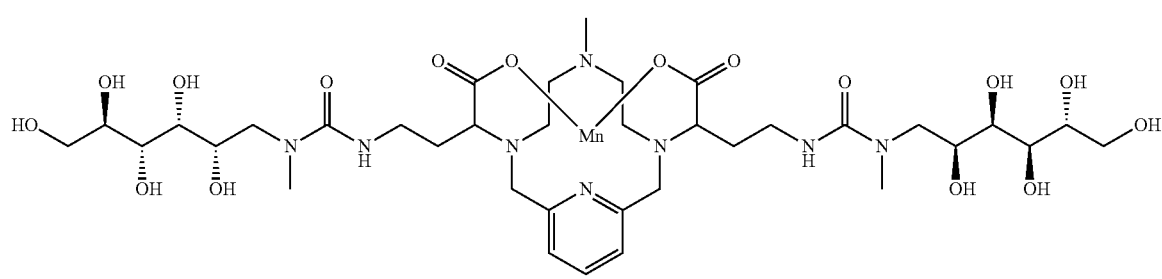

3

-continued
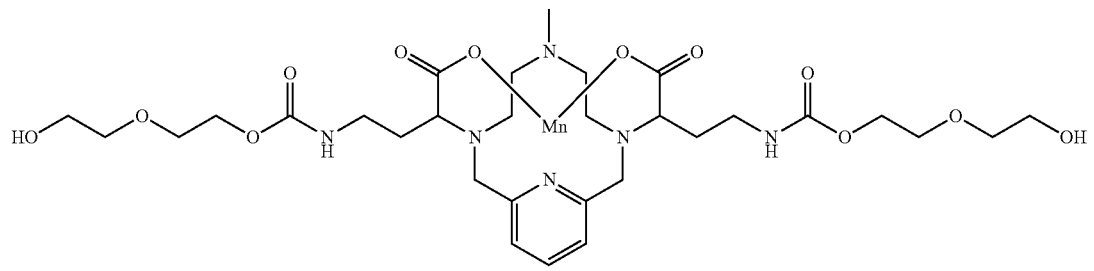
4
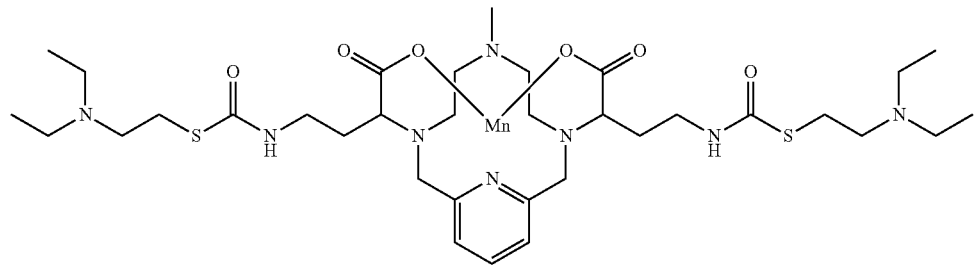
5
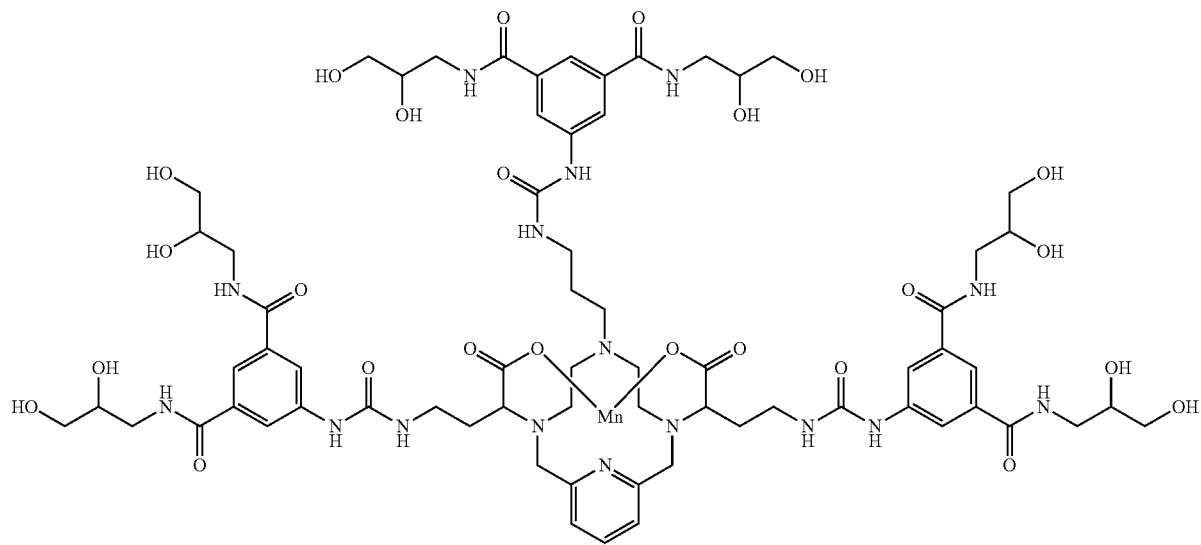
8
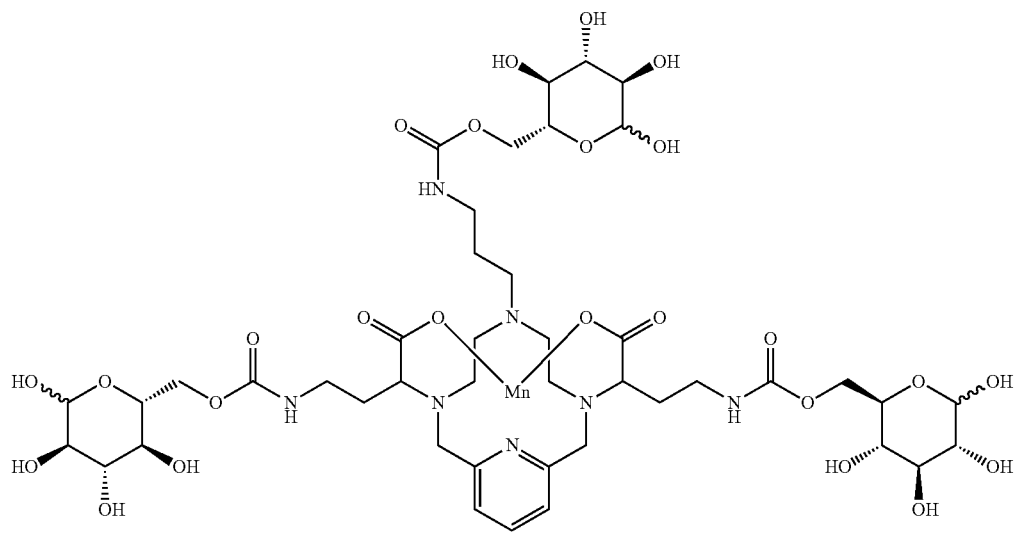
9

-continued
10
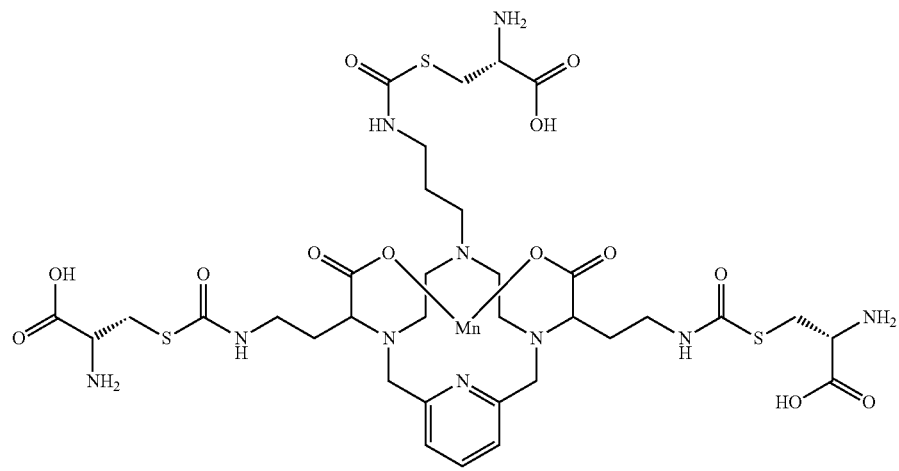
14
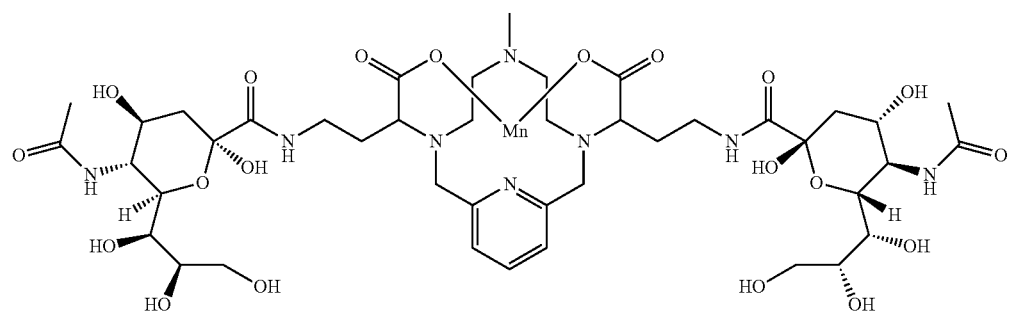
15
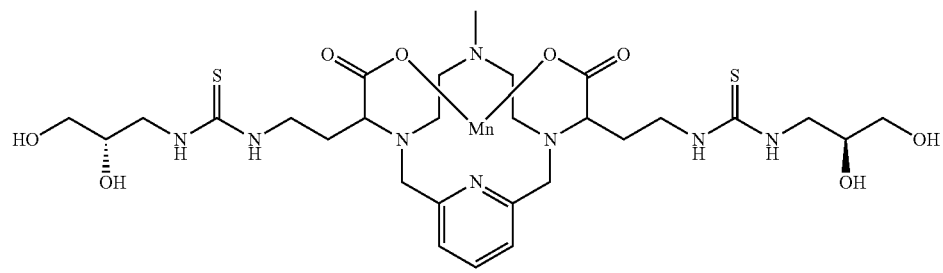
16
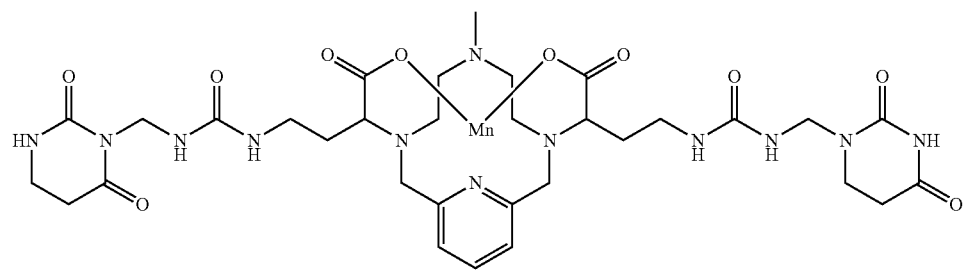
17
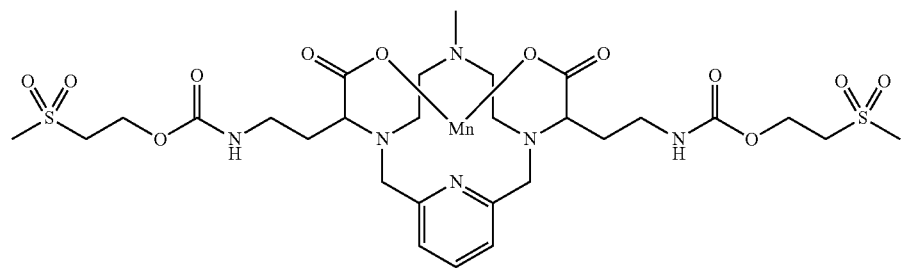

19
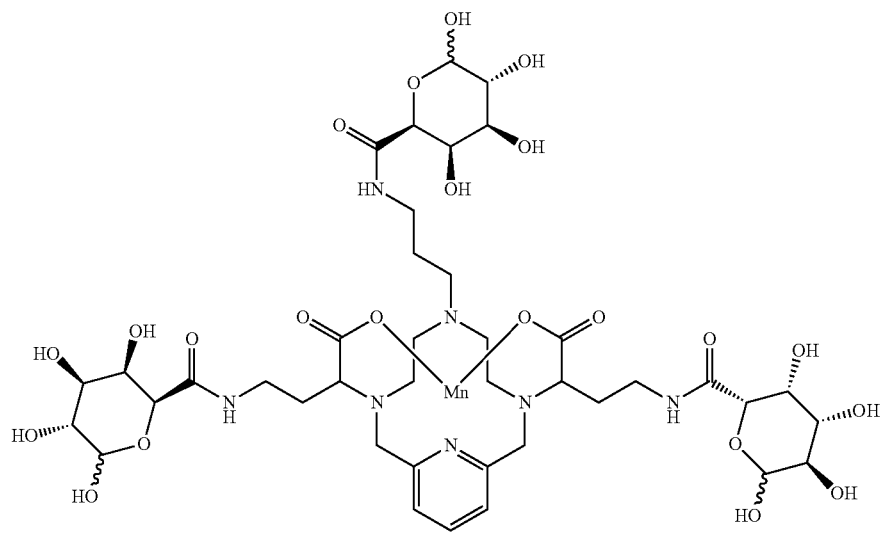
20
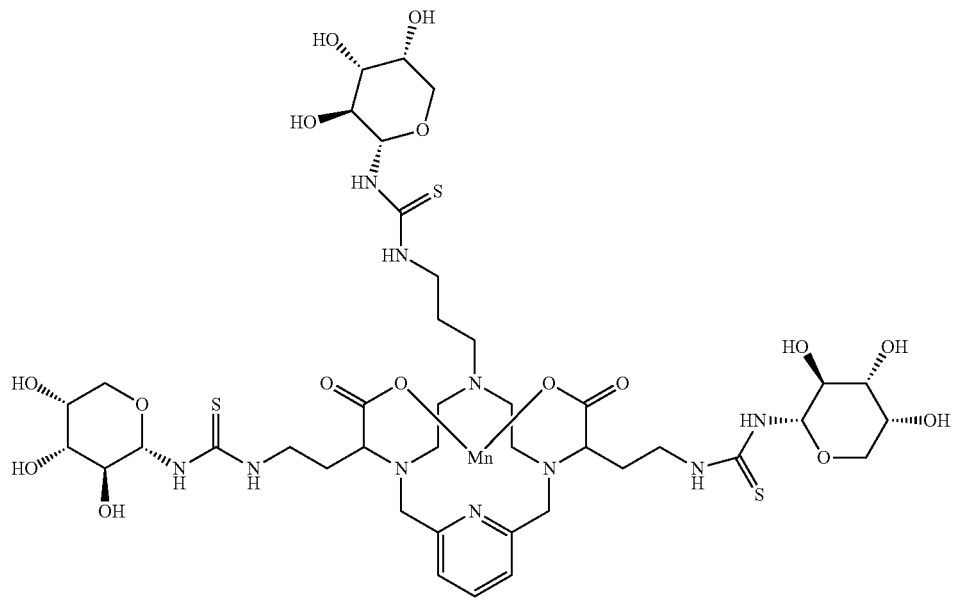
21
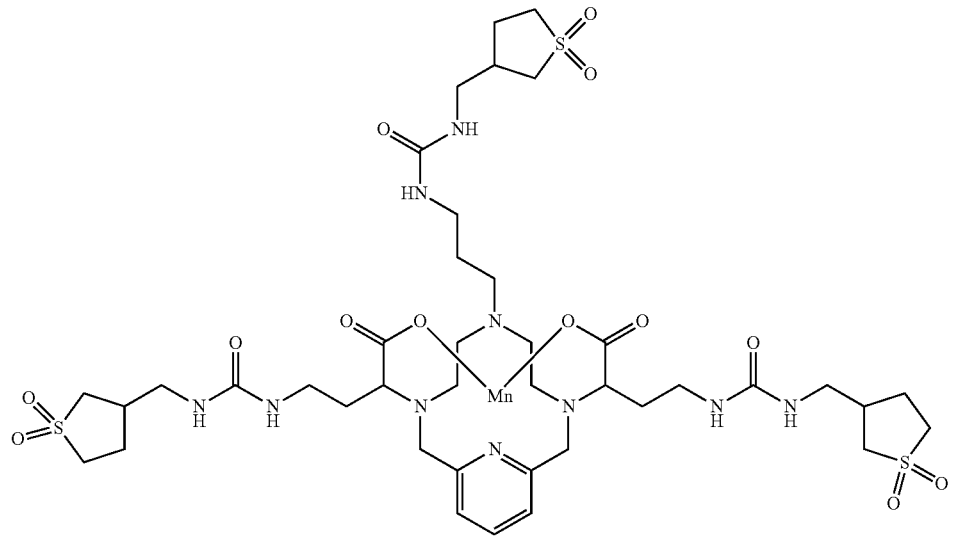

22
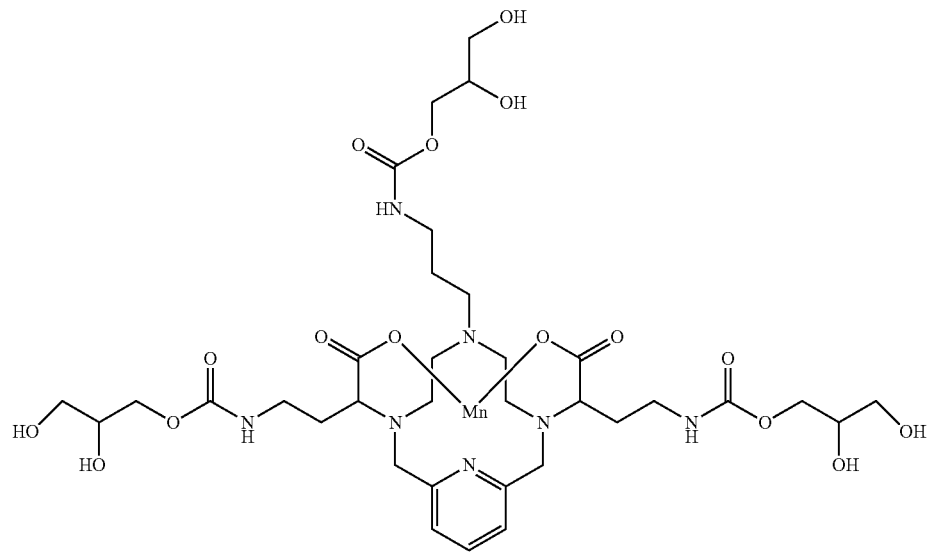
24
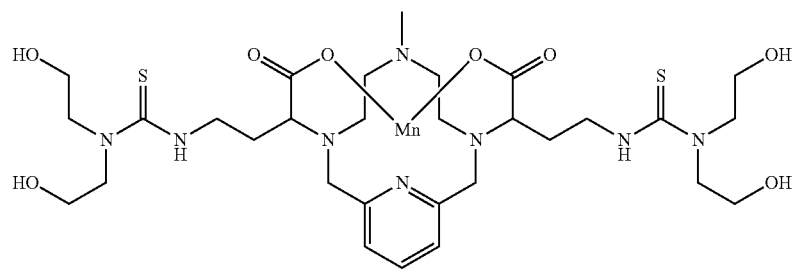
25
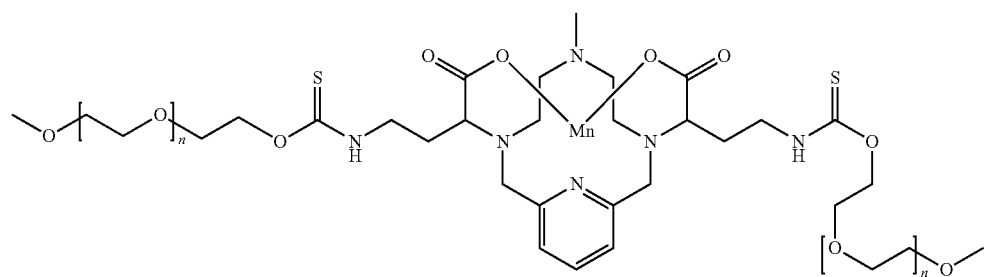
26
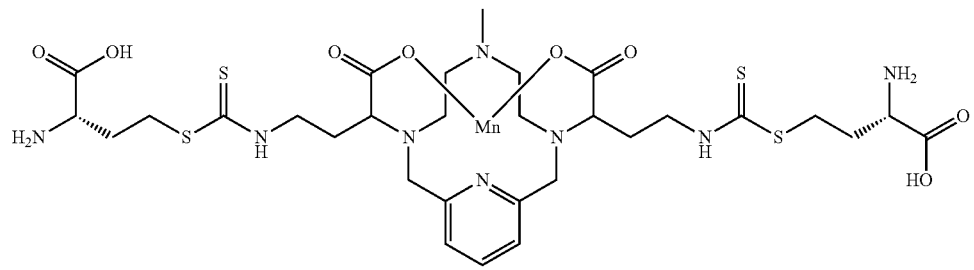

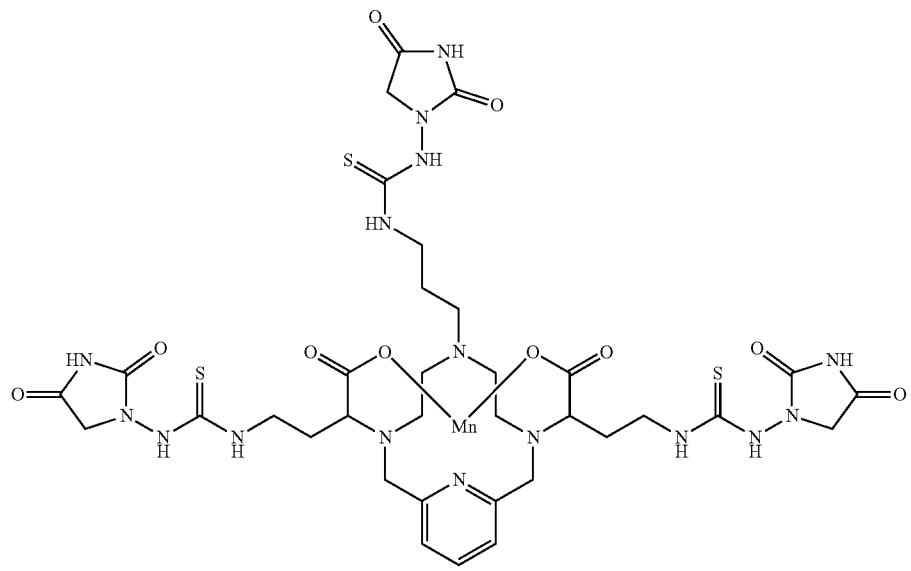
28
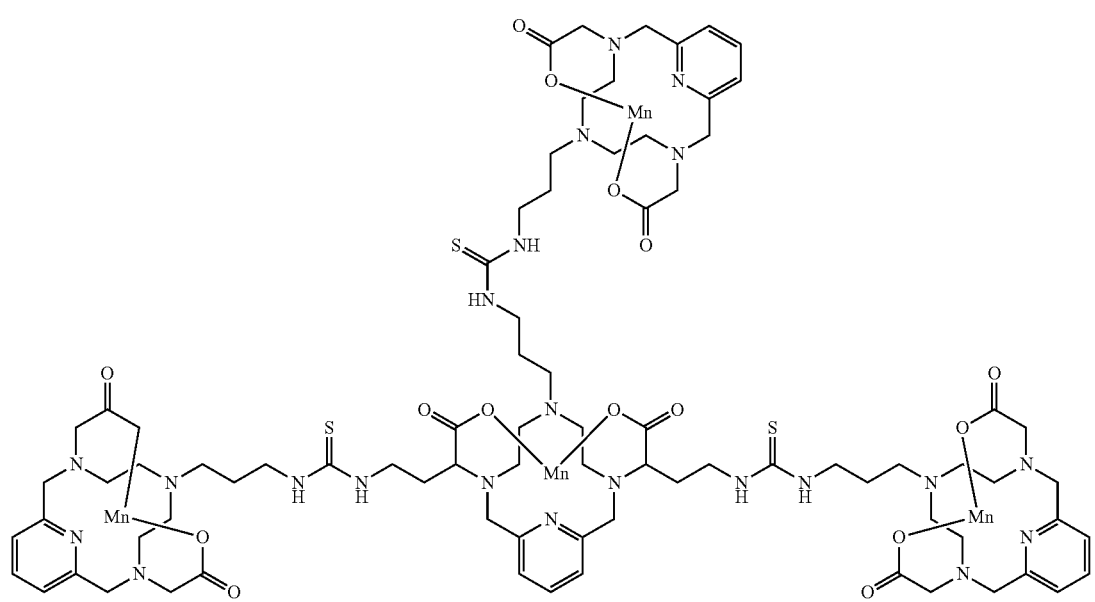
30

32
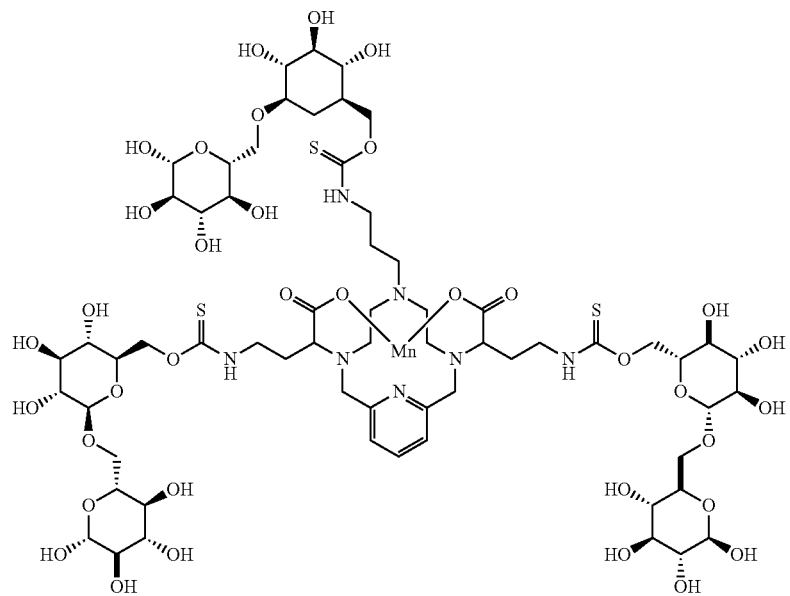
34
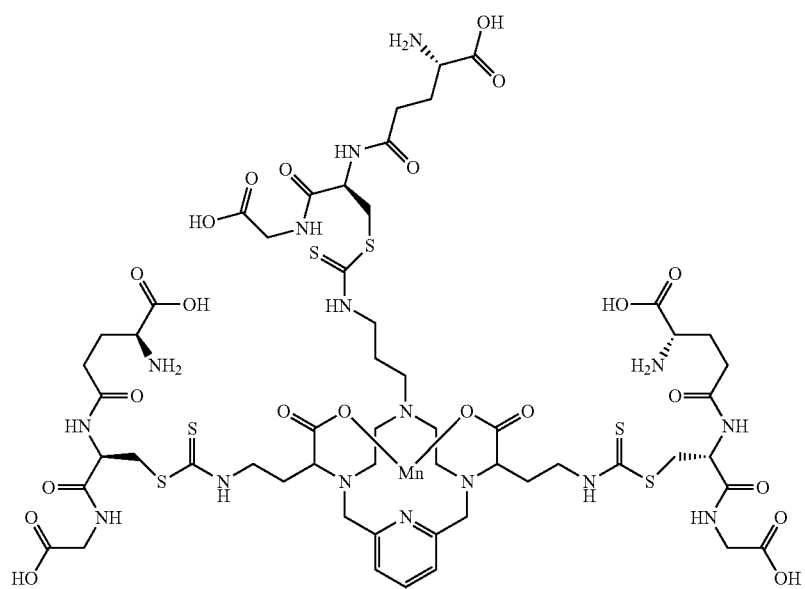
37
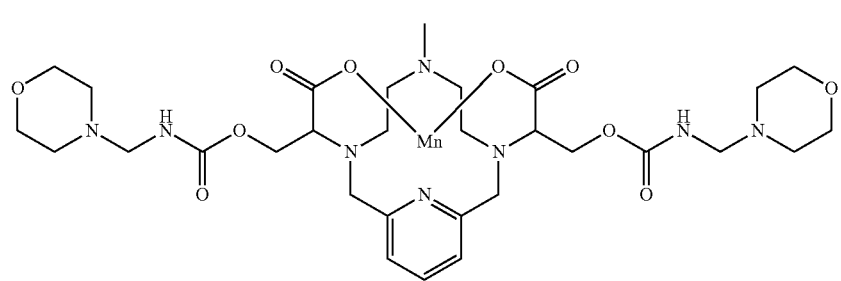

-continued

38

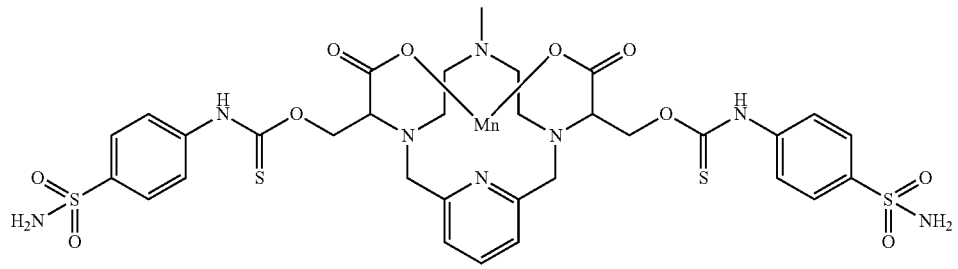

41

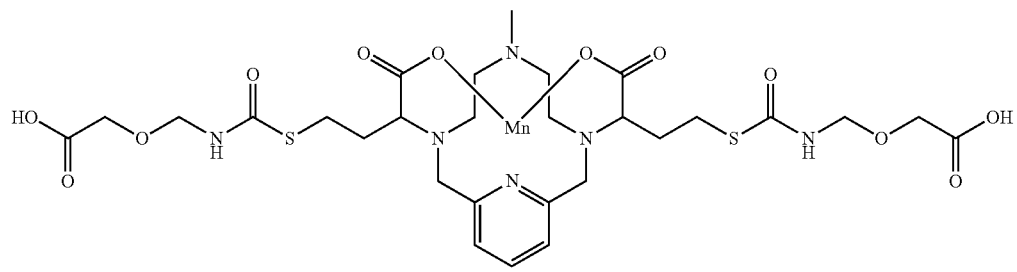

42

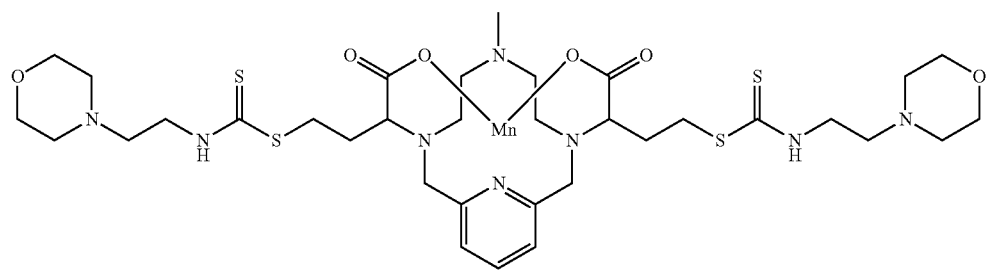

51

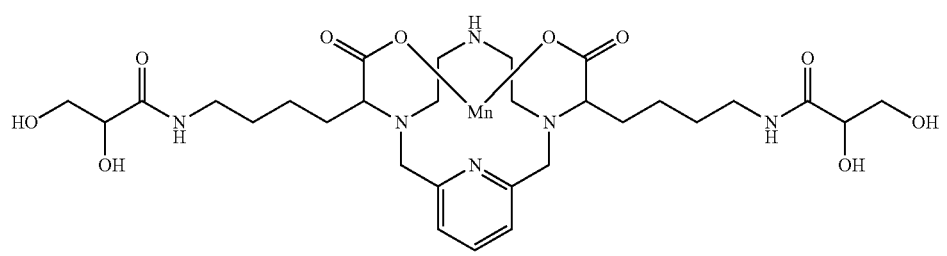

52

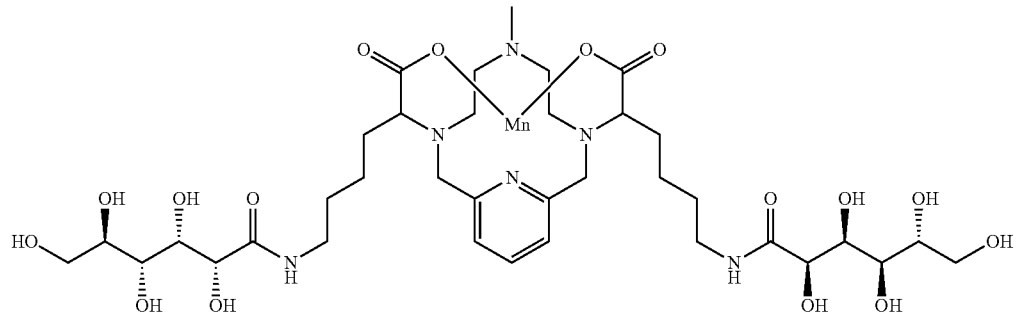

In the compounds of Formula I the carbons attached to the carboxylate arms are stereocentres. The compounds of Formula I of the invention may be provided as racemic mixture or as an enantiomerically-enriched mixture, or the racemic mixture may be separated using well-known techniques and an individual enantiomer may be used alone. In one embodiment the compound of Formula I is either a racemic mixture or diastereomerically pure.

Hydrophilic derivatization of the compounds of the invention is achieved via a non-coordinating attachment group selected from an amide, a urea, a thiourea, a carbamate, a thiocarbamate or a dithiocarbamate. The non-coordinating attachment group is too distant from the manganese ion to be significantly involved in manganese coordination thus allowing for direct manganese coordination with water and the subsequent observed contrast. The length of the non-coordinating linker of Formula I is very important, if too short (e.g. if m=1 in Formula I) there is risk it will coordinate the manganese ion, thus blocking access of water molecule, dramatically reducing the overall relaxivity of the complex. The length of the non-coordinating linker attached to a carboxymethyl arm (coordinating group) can be short (i.e. where n=0 in Formula I) as the same "arm" is unable to facilitate two coordinating groups (coordination angle will be too strained).

The compounds of Formula I can be synthesized by several synthetic pathways known to the skilled artisan from commercially available starting materials. Suitable sources of manganese for incorporation into a chelate when making compounds of the present invention include salts of carbonate ($MnCO_3$), oxide (MnO), acetate ($Mn(OAc)_2$), chloride ($MnCl_2$), hydroxide ($Mn(OH)_2$), oxalate ($MnC2O_4$), formate ($Mn(HCO_2)_2$) and nitrate ($Mn(NO_3)_2$).

The following generalized procedure may be used and/or readily adapted to obtain compounds of Formula I:

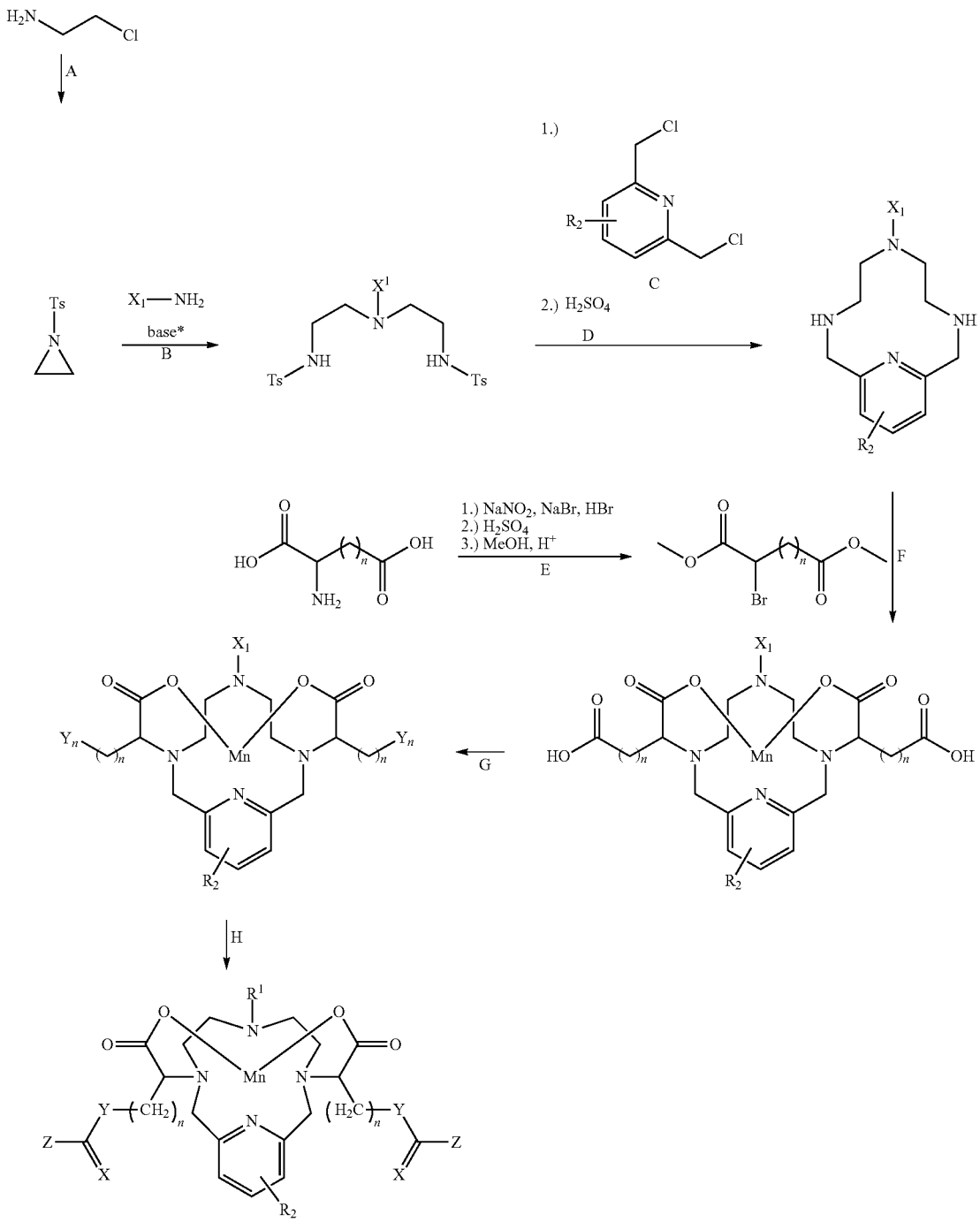

$R_2$, X, Y and Z are as defined elsewhere herein. $X_1$ represents $CH_3$ or $CH_2CH_2CH_2COOH$. $Y_n$ is as variously defined in step H below.

In summary:

A: Tosylation of aminoethanol gives aziridine. (Carrillo, Arkivoc, 2007)

B: Aziridation of aminobutanoic acid (Sigma Aldrich catalogue 56-12-2). In one embodiment aziridination of methylamine proceeds in neat acetonitrile). In one embodiment for this amino acid some base is used to activate amine. Optionally the acid functionality could be protected as an ester.

C: Cyclization with 2,6-bis(chloromethyl)-Pyridine (Sigma Aldrich catalogue 3099-28-3). In one embodiment this step is carried out in acetonitrile with potassium carbonate as the base.

D: De-tosylation using in one embodiment concentrated sulphuric acid. In one embodiment this step proceeds quantitatively.

E: Bromination based on method described in literature (Henig, J., Tóth, É., Engelmann, J., Gottschalk, S., & Mayer, H. a. (2010). Inorganic Chemistry, 49(13), 6124-38).

F: Alkylation of the polyamine/Metal incorporation, Ester Hydrolysis—In one embodiment this step is carried out in aqueous solution. In embodiments where secondary halides react sluggishly it is possible to synthesize bis-ester (E) and switch to an organic solvent to improve alkylation rate. Following alkylation the esters can be hydrolyzed with base and then following pH neutralization, the Mn(II) ion can be loaded with $MnCl_2$ and excess Mn can be precipitated using base.

G: Carboxylate activation to $Y_n$ (wherein n represents various Y groups $Y^{1-5}$ as defined for Formula I herein).

H: Coupling of various activated species with nucleophiles and electrophiles:

The carbxylates can be activated to the isocyanate using diphenylphosphorylazide (Gilman, J. W. and Otonari, Y. A (1993) Synthetic Communications 23(3) 335-341) to provide the activated intermediate $Y^1$ which can be further reacted in H with amines ([a] Ranjan, A.; et. al. (2014) Organic Letters, 16(21), 5788-5791. [b]. Petersen, T. P. et. al. (2013) 19(28), 9343-9350), alcohols ([a] Amamoto, Y. et. al. (2007) Journal of the American Chemical Society, 129(43), 13298, [b] Kim, I. et. al. (2004) Journal of Medicinal Chemistry 47(8), 2110-2122.) or thiols ([a] Peters, K. (2001) Journal of Enzyme Inhibition, 16(4), 339-350 [b] Safavi-Sohi, R. (2016) ACS Applied Materials & Interfaces 8(35) 22808-22818) to provide ureas, carbamates, and S-thiocarbamates respectively.

Additionally, the isocyanate $Y^1$ can be decomposed to produce the amine $Y^2$ by treatment with base (Chavboun, I. et. al. (2015) Journal of Natural Products, 78(5), 1026-1036.)

The amine derivatives $Y^2$ can be reacted with various carboxylic acids, isocyanates, isothiocyanates, and chloroformates to produce amides, ureas, thioureas, and carbamates respectively.

Alternatively, the amine $Y^2$ can be converted to an activated thioisocyanate $Y^3$ by treatment under various conditions including but not limited to treatment with thionyldiimidazole in DMF. The activated thioisocyanates electrophiles can subsequently coupled with amines, alcohols, or thiols to provide thioureas, O-thiocarbamates, and dithiocarbamates respectively.

Additionally, there are some instances where $Y_n$ can be activated as an alcohol (see synthesis of the diol 36) to provide alcohols ($Y^4$) which can react with isocyanates, isothiocyanates to produce carbamates and 0-thiocarbamates respectively.

Further there are instances where $Y_n$ can be activated as a nucleophilic thiol ($Y^5$) as depicted in the synthesis of the dithiol 40. Subsequent reaction of thiols with isocyanates, or isothiocyanates would lead to the formation of S-thiocarbamates, and dithiocarbamates respectively.

In step H the compound of the following formula can be used for the addition of a heterocycle:

| $Z_n$ | Name | Exemplary structure |
|---|---|---|
| $Z_1$ | amino | HN—⟨tetrahydropyran⟩ |
| $Z_2$ | aminoalkylene | $H_2N$—⟨tetrahydropyran⟩ |
| $Z_3$ | hydroxyalkylene | HO—⟨tetrahydropyran⟩ |
| $Z_4$ | thioalkylene | HS—⟨tetrahydropyran⟩ |
| $Z_5$ | isocyanatoalkylene | O=C=N—⟨tetrahydropyran⟩ |
| $Z_6$ | isothiocyanatoalkylene | S=C=N—⟨tetrahydropyran⟩ |

The resultant compounds of Formula I have a structure of Formula Ia:

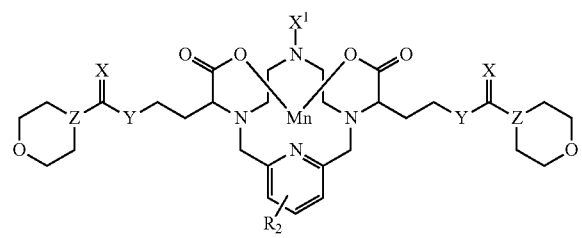

(Ia)

Where the compound of Formula I comprises at $R^4$ a substituted aryl such as a triiodiated phenyl, the compounds may be obtained using or adapting the following reaction scheme (where X, Y, Z, $R^2$ and n are as defined herein, and $Y^2$ and $Z^2$ represent functional groups suitable to permit the conjugation reaction to take place:

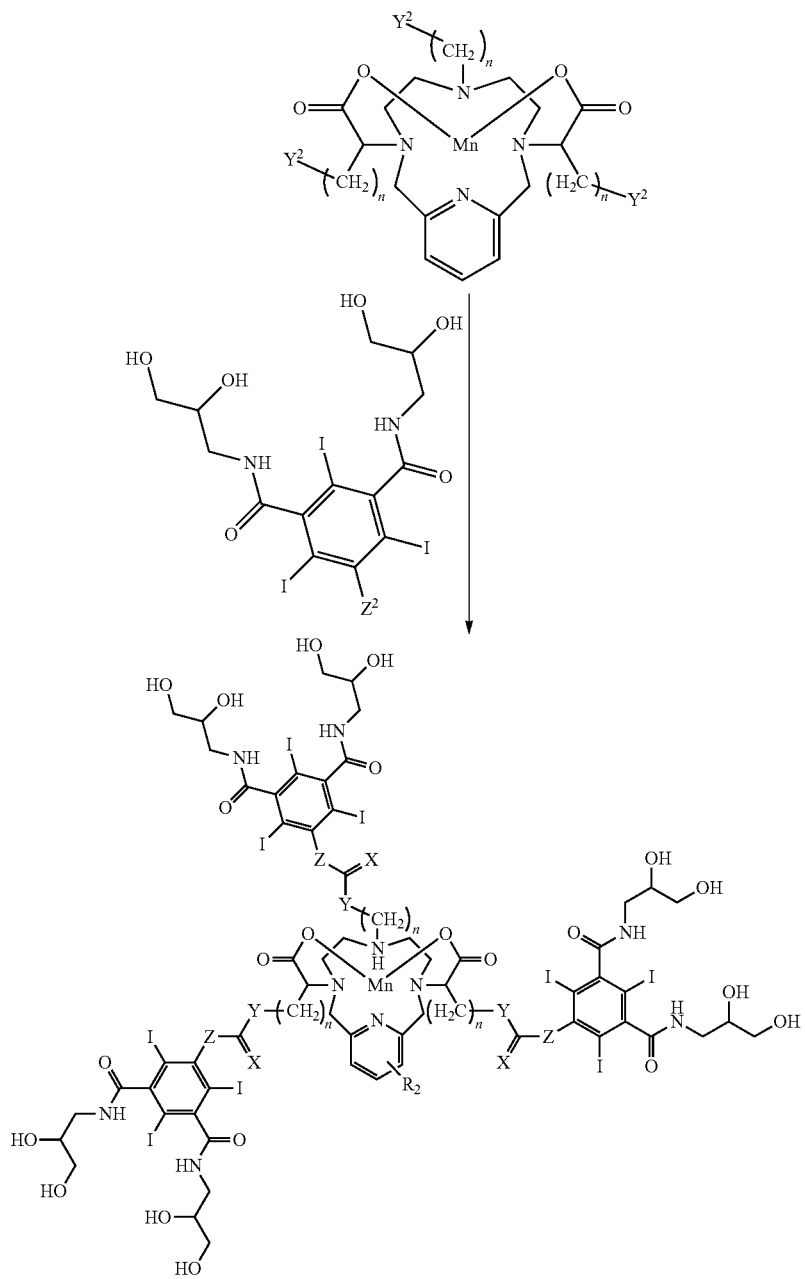

In the experimental examples below the synthesis of particular compounds is provided either via reaction schemes such as those described above, or by alternative reaction schemes. These alternative reaction schemes could also be readily adapted by a person skilled in the art to obtain other compounds of Formula I.

The reverse amide chemical structure of the Mn chelate compounds of the present invention distinguishes them from similar prior Mn chelate compounds.

It is believed that the compounds of the present invention have increased stability for Mn retention as well as against in vivo metabolism.

Suitable methods for in vitro characterization of chelate stability can be found in the literature (Idee, J.-M. Journal of Magnetic Resonance Imaging: JMRI, 2009, 30(6), 1249-58 and Baranyai, Z. Chemistry—A European Journal, 2015, 21(12), 4789-4799). Other suitable methods include in vitro studies of physiological media (i.e. human serum or plasma) to monitor the transmetallation inertness. Another suitable method of assessing transmetallation inertness would be to measure retention of metal ions in vivo, following injection of the chelated metal. It is known that intact chelates normally follow very rapid clearance kinetics.

In one aspect of the invention the compound of Formula I is provided as a pharmaceutical composition. A "pharmaceutical composition" is a composition comprising the compound of the invention, together with a biocompatible carrier in a form suitable for mammalian administration. The "biocompatible carrier" is a fluid, especially a liquid, in which the compound of Formula I is suspended or dissolved, such that the resulting composition is physiologically tolerable, i.e. can be administered to the mammalian body without toxicity or undue discomfort (which can be understood to be a definition of the term "suitable for mammalian administration").

The pharmaceutical composition of the invention is suitable for use as a magnetic resonance (MR) contrast medium in magnetic resonance imaging (MRI) of the human and non-human animal body.

In one embodiment the pharmaceutical composition of the invention may comprise one or more pharmaceutically-acceptable excipients. These suitably do not interfere with the manufacture, storage or use of the final composition.

Non-limiting examples of suitable pharmaceutically-acceptable excipients include buffering agents, stabilizers, antioxidants, osmolality adjusting agents, pH adjusting agents, excess cheland and weak complexes of physiologically tolerable ions. These and other suitable excipients will be well known to those of skill in the art and are further described in e.g. WO1990003804, EP0463644-A, EP0258616-A and U.S. Pat. No. 5,876,695 the content of which are incorporated herein by reference. The pharmaceutical composition of the invention in one embodiment is in a form suitable for parenteral administration, for example injection. The pharmaceutical composition according to the invention may therefore be formulated for administration using physiologically acceptable excipients in a manner fully within the skill of the art. For example, the compound of Formula I, optionally with the addition of pharmaceutically acceptable excipients, may be suspended or dissolved in an aqueous medium, with the resulting solution or suspension then being sterilized.

A non-limiting example of a suitable buffering agent is tromethamine hydrochloride.

The term "excess cheland" is defined as any compound capable of scavenging free paramagnetic ion (manganese), but not paramagnetic ion (manganese) retained within the complexes of this invention, as described in EP2988756A1.

Although small amounts are essential to human health, overexposure to free manganese ions may result in the neurodegenerative disorder known as "manganism" with symptoms resembling Parkinson's disease. However, the fundamental issue for Mn, as well as other metals, as contrast agents is in their chelation stability. Chelation stability is an important property that reflects the potential release of free metal ions in vivo. It is known that there is a correlation between the amount of excess cheland in a paramagnetic chelate formulation and the amount of paramagnetic metal deposited in animal models (Sieber 2008 J Mag Res Imaging; 27(5): 955-62). Therefore, in another embodiment, an amount of excess cheland is selected that can act as a Mn scavenger so as to reduce or prevent release of Mn from the formulation post injection. The optimal amount of free cheland will result in a pharmaceutical composition having suitable physicochemical properties (i.e. viscosity, solubility and osmolality) and avoiding toxological effects such as zinc depletion in the case of too much free cheland. U.S. Pat. No. 5,876,695 describes in particular an excess of linear chelate, in particular of free DTPA, and this is a non-limiting example of an excess cheland suitable for use in the pharmaceutical composition of the present invention. This formulation strategy is used for products such as Magnevist™, Vasovist™ or Primovist™. WO2009103744 describes a similar formulation strategy, based on the addition of a precise amount of free chelate, so as to have a very small excess of said chelate and a zero concentration of free lanthanide.

The physiologically tolerable ion may in one embodiment be selected from physiologically tolerable ions include calcium or sodium salts such as calcium chloride, calcium ascorbate, calcium gluconate or calcium lactate.

Parenterally administrable forms should be sterile and free from physiologically unacceptable agents and should have low osmolality to minimize irritation or other adverse effects upon administration and thus the pharmaceutical composition should be isotonic or slightly hypertonic. Non-limiting examples of suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, $22^{nd}$ Edition (2006 Lippincott Williams & Wilkins) and The National Formulary (https://books.google.com/books?id=O3qixPEMwssC&=THE+NANATIONAL+FORMULARY&dq=THE+NATIONAL+FORMULARY&hl=en&sa=X&ved=0CC8Q6AEwAGoVChMImfPHrdTgyAIVJfNyCh1RJw_E).

For the pharmaceutical composition of the invention to be administered parenterally, i.e. by injection its preparation further comprises steps including removal of organic solvent, addition of a biocompatible buffer and any optional further ingredients such as excipients or buffers. For parenteral administration, steps to ensure that the pharmaceutical composition is sterile and apyrogenic also need to be taken.

In another embodiment the present invention provides a method comprising administration of the compound of Formula I as defined herein in the generation of MR images and/or MR spectra.

Methods of administration and subjects envisaged as suitable in the context of the present invention have been described hereinabove in connection with the pharmaceutical composition. Administration of the compound of Formula I is preferably carried out parenterally, and most preferably intravenously. The intravenous route represents the most efficient way to deliver the compound throughout the body of the subject. Furthermore, intravenous administration does not represent a substantial physical intervention or a substantial health risk. The compound of Formula I of the invention is preferably administered as the pharmaceutical composition of the invention, as defined above. The method of the invention can also be understood as comprising steps (ii)-(iii) carried out on a subject to whom the compound of the invention has been pre-administered. In one embodiment the pharmaceutical composition is administered in an amount suitable to enhance the contrast in a method of MR imaging (MRI). For further detail on MRI methods the reader is referred to the common general knowledge in the art, e.g. as taught in Chapter 27 "Contrast Agents and Magnetic Resonance Imaging" in "Magnetic Resonance Imaging: Physical and Biological Principles" ($4^{th}$ Edition 2015 Elsevier, Stewart Carlyle Bushong & Geoffrey Clarke, Eds.) or in "Contrast Agents I: Magnetic Resonance Imaging" (2002 Springer-Verlang, Werner Krause, Ed.).

The method of the invention may be used to study a biological marker or process in healthy subjects, or alternatively in subjects known or suspected to have a pathological condition associated with abnormal expression of a biological marker. When the method is used to image a subject known or suspected to have a pathological condition it has utility in a method for the diagnosis of said condition.

The "detection" step of the method of the invention involves detection of signals emitted by the compound of Formula I by means of a detector sensitive to said signals. This detection step can also be understood as the acquisition of signal data.

The "qeneration" step of the method of the invention is carried out by a computer which applies a reconstruction algorithm to the acquired signal data to yield a dataset. This dataset is then manipulated to generate one or more images and/or one or more spectra showing the location and/or amount of signals.

The "subject" of the invention can be any human or animal subject. In one embodiment the subject of the invention is a mammal. In one embodiment said subject is an intact mammalian body in vivo. In another embodiment, the subject of the invention is a human.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All patents and patent applications mentioned in the text are hereby incorporated by reference in their entireties, as if they were individually incorporated.

Brief Description of the Examples

The examples hereunder describe methods by which a non-limiting selection of compounds of the present invention may be obtained. Compounds 3-5, 8-10, 14-17, 19-22, 24-26, 28, 30, 32, 34, 37, 38, 41, 42 and 51 represent examples of compounds of the present invention. For any examples that are prophetic, adjustments may need to be made to account for variations in reagent solubility and reactivity including the use of alternative solvents, different reaction times, temperatures, or concentrations or alternate but equivalent reagent systems. Any such adjustments are regarded as routine for one of skill in the art.

Synthesis of the Bisisocyanate 2

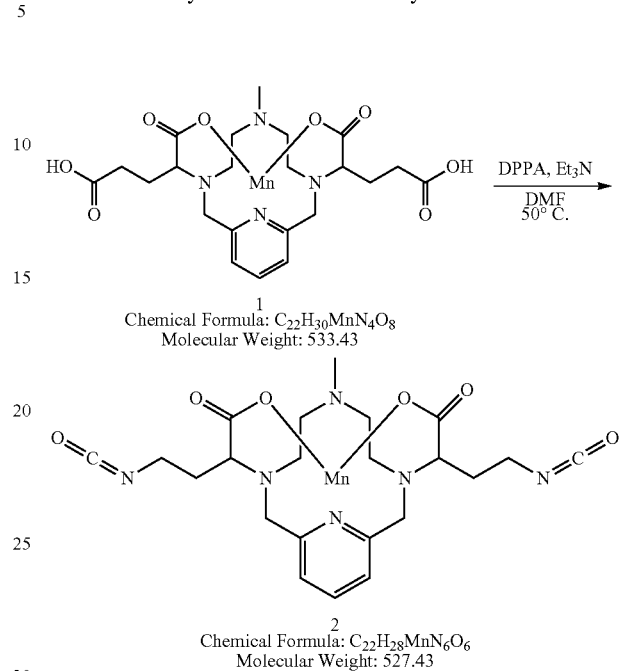

The starting material 1 is suspended in degassed dimethylformamide. Triethylamine (2 equivalents) is added, followed by diphenylphosphorylazide (2 equivalents). The reaction mixture is stirred with heating at 50° C. until analytical chromatography indicates consumption of the starting material. The use of additional equivalents of triethylamine and diphenylphosphorylazide may be required to drive the reaction to completion. Once complete, the isocyanate 2 is used directly in subsequent reactions as a solution in DMF.

Synthesis of Conjugate 3

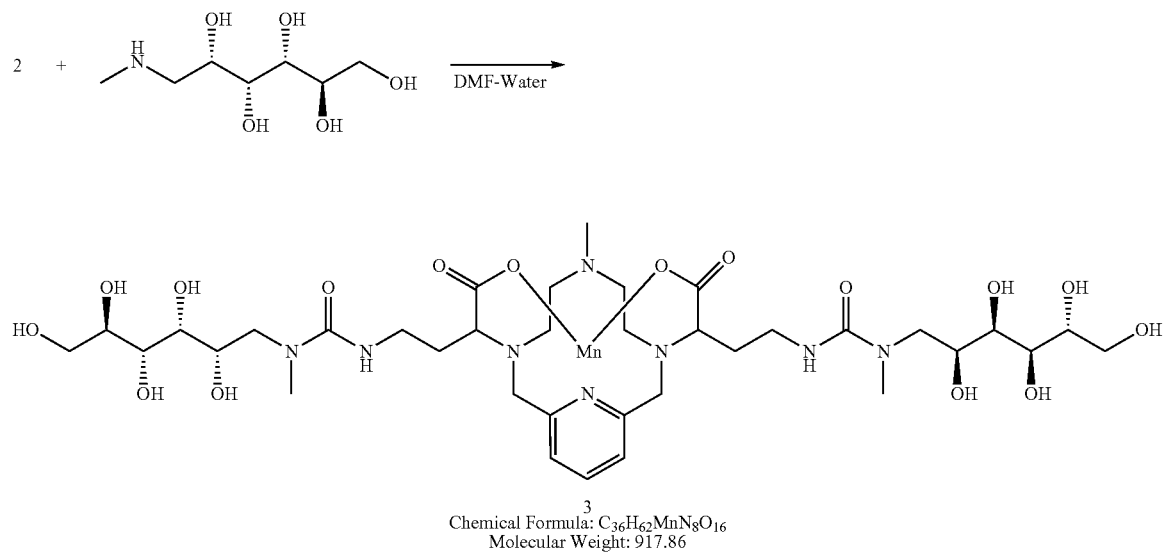

A solution of N-methyl-D-glucamine in water (2 equivalents) is added to the isocyanate 2 in DMF. The reaction mixture is stirred for several hours at room temperature and its progress is monitored using analytical chromatographic techniques. The addition of excess N-methyl-D-glucamine may be necessary to drive the reaction to completion. The product 3 is purified using reversed phase chromatography on C-18 functionalized silica gel and eluting with water-acetonitrile or water-methanol mixtures.

Synthesis of Conjugate 4

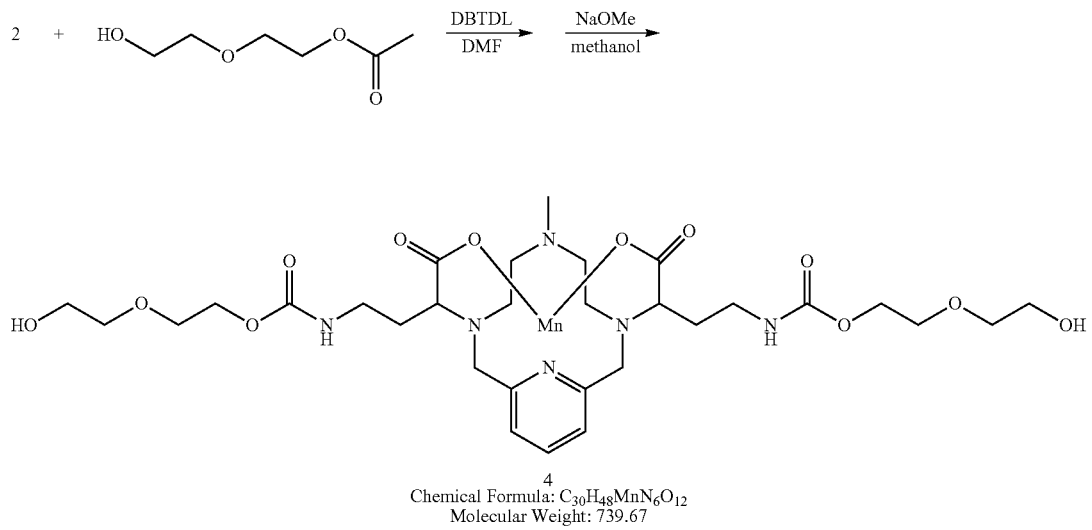

A solution of 2-(2-hydroxyethoxy)ethyl acetate in DMF (2 equivalents) is added to a solution of the isocyanate 2 in DMF. A catalytic amount of dibutyltin dilaurate is added to the reaction mixture and the mixture is heated to 70° C. to drive the reaction to completion, analytical chromatographic procedures are used to ascertain reaction progress. Upon completion, the solvent is removed under reduced pressure, the residue is suspended in a solution of methanol containing a catalytic quantity of sodium methoxide. The reaction is allowed to proceed until complete hydrolysis of the acetate protecting groups is observed. Once complete, the reaction mixture is concentrated under reduced pressure, and the residue is purified using reversed phase chromatography on C-18 functionalized silica gel and eluting with water-acetonitrile or water-methanol mixtures.

Synthesis of Conjugate 5

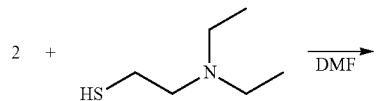

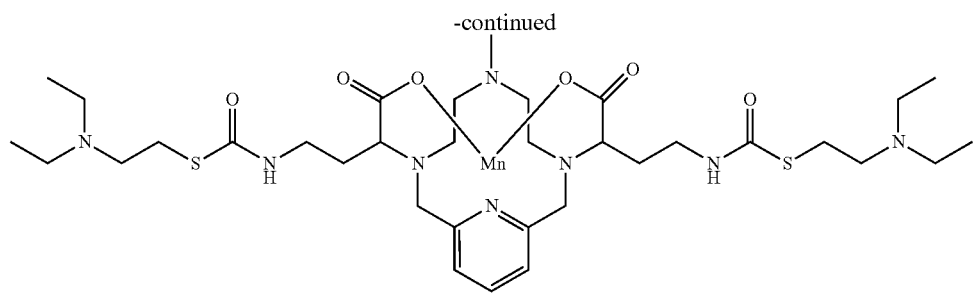

5
Chemical Formula: $C_{34}H_{58}MnN_8O_6S_2$
Molecular Weight: 793.94

A solution of 2-(Diethylamino)ethanethiol hydrochloride (2 equivalents) and triethylamine (2 equivalents) in degassed DMF is added to a solution of the isocyanate 2 in DMF. The reaction mixture is allowed to stir at room temperature and the progress of the reaction is monitored using analytical chromatography. Upon completion, the solvent is removed under reduced pressure, and the residue is purified using reversed phase chromatography on C-18 functionalized silica gel and eluting with water-acetonitrile or water-methanol mixtures.

Synthesis of the Trisisocyanate 7

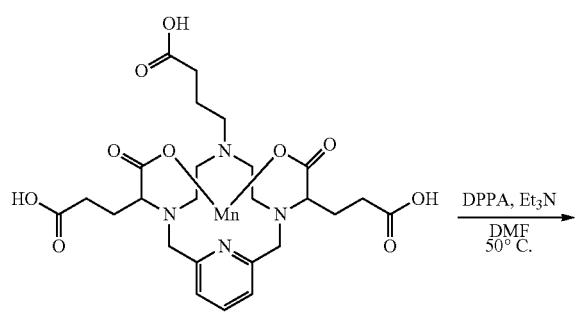

6
Chemical Formula: $C_{25}H_{34}MnN_4O_{10}$
Molecular Weight: 605.50

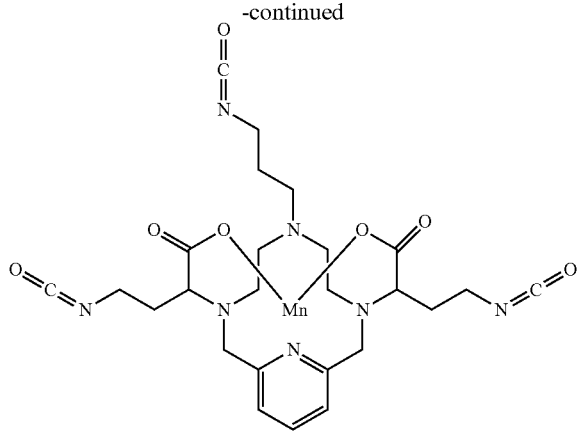

7
Chemical Formula: $C_{25}H_{31}MnN_7O_7$
Molecular Weight: 596.49

The starting material 6 is suspended in degassed dimethylformamide. Triethylamine (3 equivalents) is added, followed by diphenylphosphorylazide (3 equivalents). The reaction mixture is stirred with heating at 50° C. until analytical chromatography indicates consumption of the starting material. The use of additional equivalents of triethylamine and diphenylphosphorylazide may be required to drive the reaction to completion. Once complete, the isocyanate 7 is used directly in subsequent reactions as a solution in DMF.

Synthesis of Conjugate 8

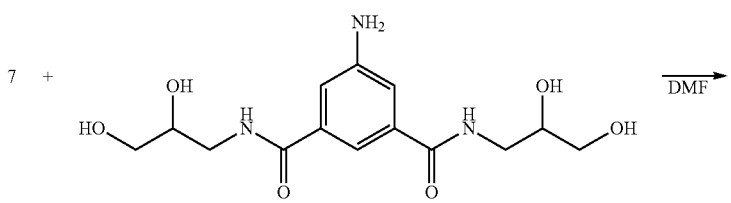

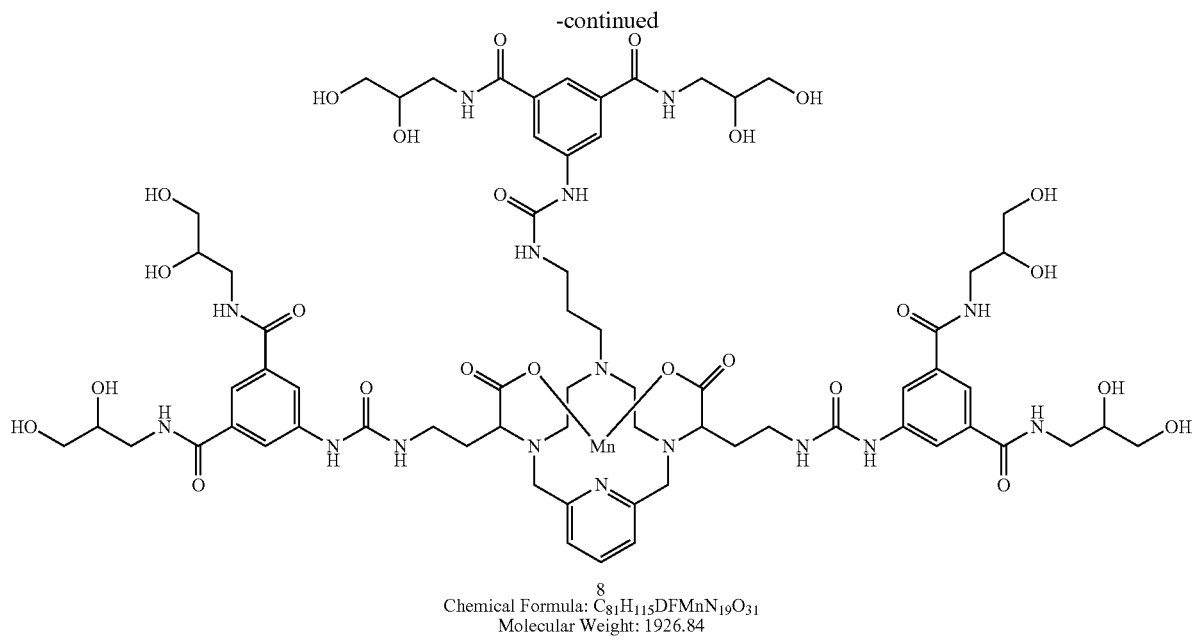

8
Chemical Formula: $C_{81}H_{115}DFMnN_{19}O_{31}$
Molecular Weight: 1926.84

A solution of 5-Amino-N,N'-bis(2,3-dihydroxypropyl) isophthalamide in DMF (2 equivalents) is added to the isocyanate 7 in DMF. The reaction mixture is stirred for several hours at room temperature and its progress is monitored using analytical chromatographic techniques. The addition of excess 5-Amino-N,N'-bis(2,3-dihydroxypropyl) isophthalamide may be necessary to drive the reaction to completion. The product 8 is purified using reversed phase chromatography on C-18 functionalized silica gel and eluting with water-acetonitrile or water-methanol mixtures.

Synthesis of Conjugate 9

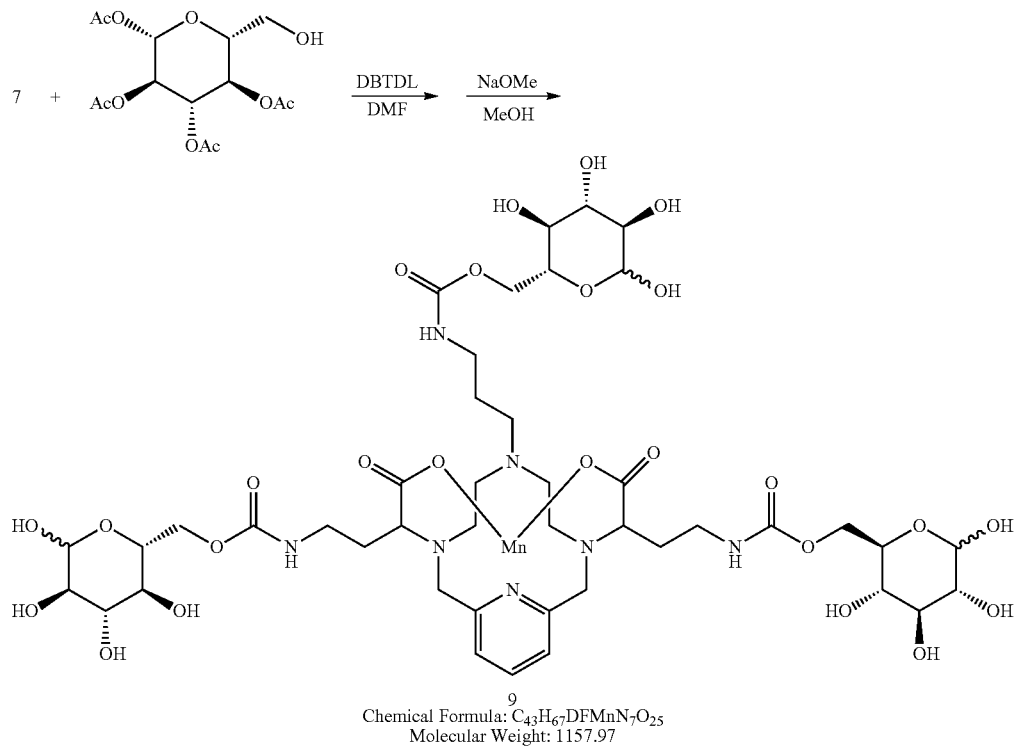

9
Chemical Formula: $C_{43}H_{67}DFMnN_7O_{25}$
Molecular Weight: 1157.97

Synthesis of conjugate 9—A solution of β-D-glucopyrannose, 1,2,3,4 tetraacetate in DMF (3 equivalents) is added to a solution of the isocyanate 7 in DMF. A catalytic amount of dibutyltin dilaurate is added to the reaction mixture and the mixture is heated to 70° C. to drive the reaction to completion, analytical chromatographic procedures are used to ascertain reaction progress. Additional portions of β-D-glucopyrannose, 1,2,3,4 tetraacetate may be required to drive the reaction to completion. Upon completion, the solvent is removed under reduced pressure, the residue is suspended in a solution of methanol containing a catalytic quantity of sodium methoxide. The reaction is allowed to proceed until complete hydrolysis of the acetate protecting groups is observed. Once complete, the reaction mixture is concentrated under reduced pressure, and the residue is purified using reversed phase chromatography on C-18 functionalized silica gel and eluting with water-acetonitrile or water-methanol mixtures.

Synthesis of Conjugate 10

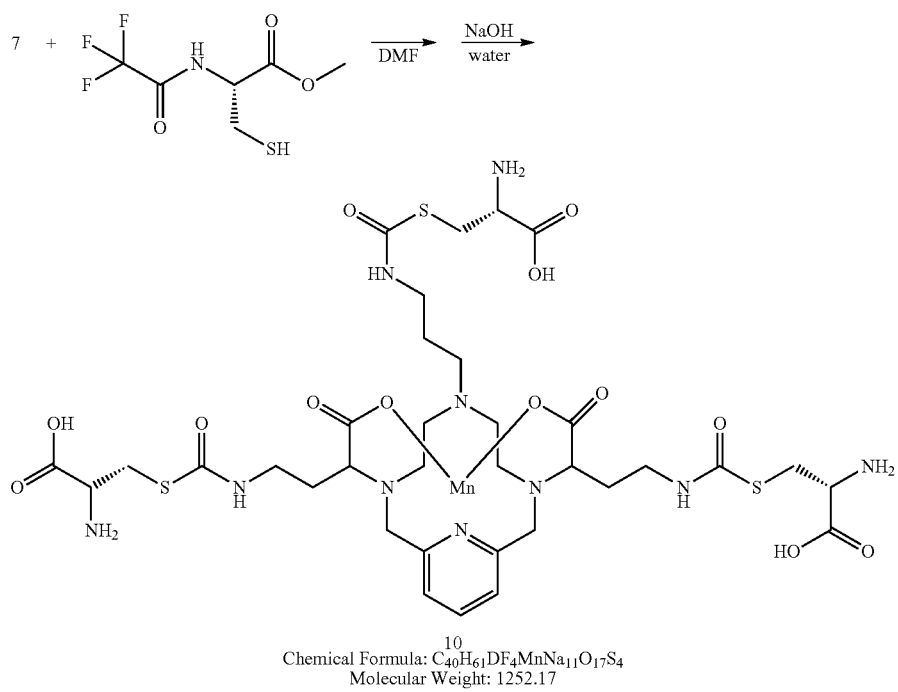

A solution of N-trifluoroacetyl-L-cysteine methylester (3 equivalents) in degassed DMF is added to a solution of the isocyanate 7 in DMF. The reaction mixture is allowed to stir at room temperature and the progress of the reaction is monitored using analytical chromatography. Upon completion, the solvent is removed under reduced pressure, and the reside is treated with sodium hydroxide in water to remove the methylester and trifluoroacetamide protecting groups. The pH of the reaction mixture is adjusted to 7 through the addition of aqueous HCl and the reaction is directly purified using reversed phase chromatography on C-18 functionalized silica gel and eluting with water-acetonitrile or water-methanol mixtures.

Synthesis of the Amine Functionalized Chelate 11

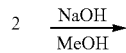

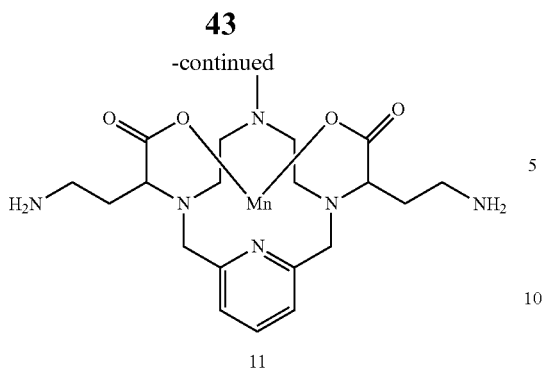

The bisisocyanate 2 is dissolved in anhydrous methanol at room temperature. Subsequently a solution of NaOH in methanol is added to hydrolyze the resulting bismethyl carbamate to the desired amine 11. The progress if the reaction is monitored by analytical chromatography. Upon completion, the reaction pH is adjusted to 7 and the solvent is removed under reduced pressure. If necessary, the isolated residue can by purified using reversed phase chromatography on C-18 functionalized silica gel and eluting with water-acetonitrile or water-methanol mixtures to provide pure 11.

Alternate Synthesis of the Amine Functionalized Chelate 11

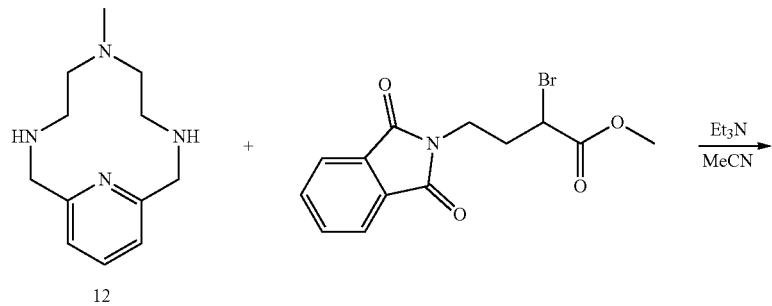

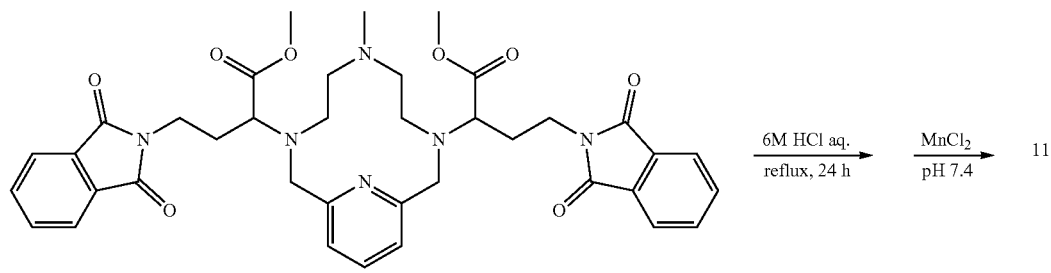

13
Chemical Formula: $C_{38}H_{42}N_6O_8$
Molecular Weight: 710.18

The pyramine 12 and methyl 2-bromo-4-(1,3-dioxoisoindolin-2-yl)butanoate (2 equivalents) are dissolved in acetonitrile and triethylamine (2.2 equivalents is added. The reaction is allowed to continue stirring at room temperature and the reaction progress to 13 is monitored using analytical chromatography. Upon completion, the reaction is concentrated under reduced pressure and the resulting residue is purified using reversed phase chromatography on C-18 functionalized silica gel by eluting with water acetonitrile or water-methanol mixtures to provide 13. The compound 13 is suspended in 6M aqueous HCl and heated with stirring to 100° C. for 24 h. Following this time the reaction mixture is filtered to remove insoluble solids and the filtrate is collected and its pH adjusted to 7.4 using a 50% w/w solution of sodium hydroxide. Once the pH of the reaction mixture is stable at 7.4, $MnCl_2 \cdot xH_2O$ (~2.4 equivalents) is added to the reaction mixture and the mixture is stirred at room temperature. Additional NaOH solution is added to the reaction mixture to maintain the pH of the reaction mixture between 7.0 and 7.4. The progress of the manganese incorporation is monitored by analytical chromatography, and upon completion, the reaction pH is adjusted to 12 by the addition of aqueous NaOH. The reaction mixture is allowed to continue stirring for 1 h at room temperature, and then the reaction mixture is filtered to remove solids and the filtrate is collected and its pH adjusted to 7.4 through the addition of an aqueous solution of HCl. The desired compound 11 is further purified using reversed phase chromatography on C-18 functionalized silica gel and eluting with water-acetonitrile or water-methanol mixtures.

Synthesis of the Conjugate 14

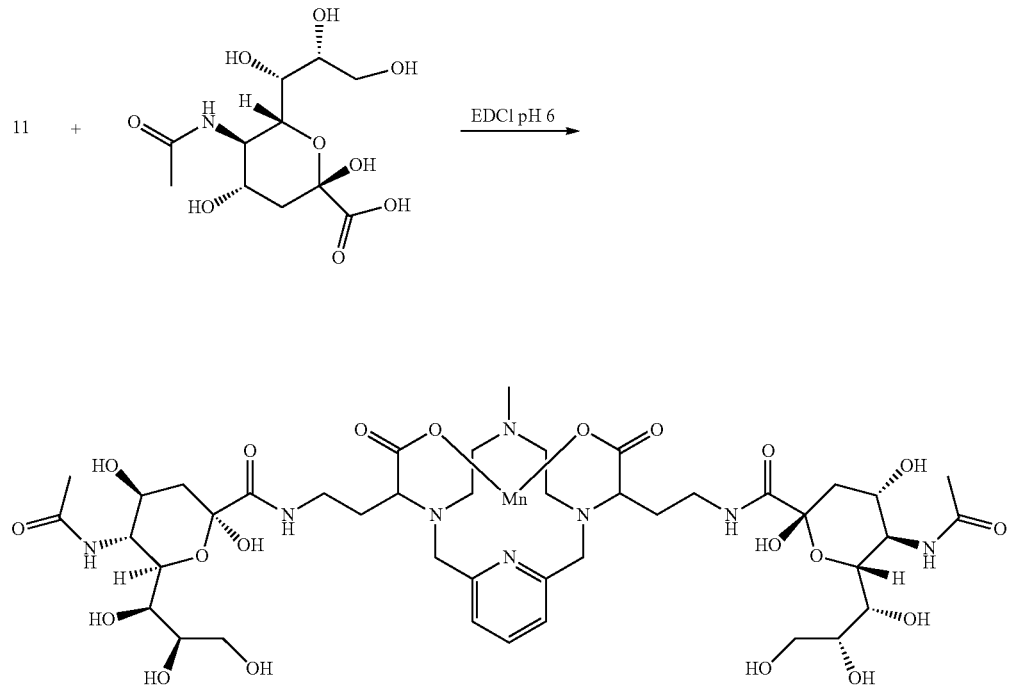

14
Chemical Formula: $C_{42}H_{66}MnN_8O_{20}$
Molecular Weight: 1057.95

The aminopyramine 13 is dissolved in water and N-acetylneuraminic acid (2.1 eq) and EDCl-HCl (2.1 eq) are added. The pH is adjusted to 6.5 with HCl and HOBt (0.4 eq) is then added. The pH of the resulting solution is maintained at approximately 6 while stirring for 16 h. Additional EDCl-HCl (1.1 eq) is then added, and the reaction pH is maintained at pH approximately 6 and is stirred for an additional 16 h. The solvent is removed in vacuo and the desired compound 14 is further purified using reversed phase chromatography on C-18 functionalized silica gel and eluting with water-acetonitrile or water-methanol mixtures.

Synthesis of the Conjugate 15

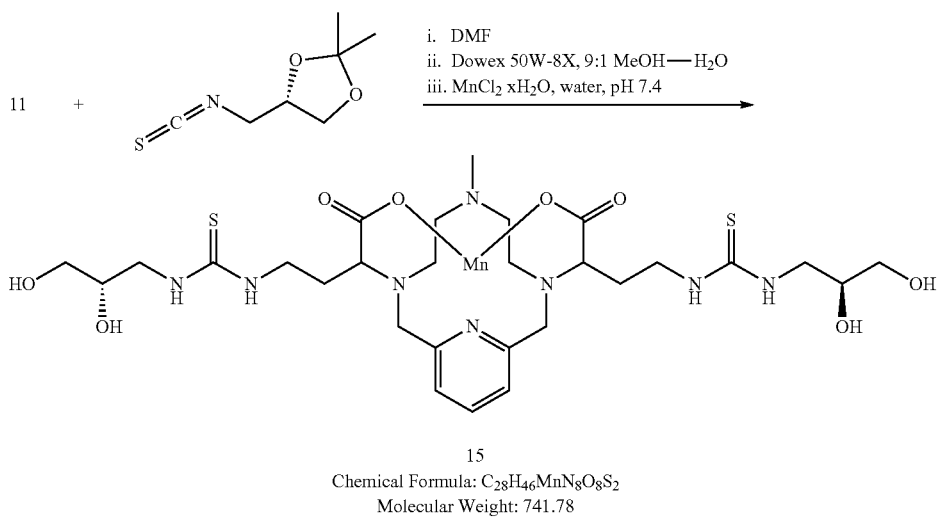

15
Chemical Formula: $C_{28}H_{46}MnN_8O_8S_2$
Molecular Weight: 741.78

A solution of (S)-4-(isothiocyanatomethyl)-2,2-dimethyl-1,3-dioxolane in DMF (2 equivalents) is added to the diamine 11 in DMF. The reaction mixture is stirred for several hours at room temperature and its progress is monitored using analytical chromatographic techniques. The addition of excess (S)-4-(isothiocyanatomethyl)-2,2-dimethyl-1,3-dioxolane may be necessary to drive the reaction to completion. Upon completion, the reaction mixture is concentrated under reduced pressure, and the residue is taken up in 9:1 MeOH—H$_2$O and Dowex 50W-8X resin is added. The heterogeneous mixture is stirred at room temperature and progress of the reaction is assessed by analytical chromatography. Upon completion, the resin is removed by filtration and the filtrate is concentrated under reduced pressure. The residue is taken up in water and the pH of the mixture is adjusted to 7.4. Additional MnC12 xH$_2$O (1 equivalent) is added and the mixture is stirred at room temperature. Additional NaOH solution is added to the reaction mixture to maintain the pH of the reaction mixture between 7.0 and 7.4. The progress of the manganese incorporation is monitored by analytical chromatography, and upon completion, the reaction pH is adjusted to 12 by the addition of aqueous NaOH. The reaction mixture is allowed to continue stirring for 1 h at room temperature, and then the reaction mixture is filtered to remove solids and the filtrate is collected and its pH adjusted to 7.4 through the addition of an aqueous solution of HCl. The desired compound 15 is further purified using reversed phase chromatography on C-18 functionalized silica gel and eluting with water-acetonitrile or water-methanol mixtures.

Synthesis of Conjugate 16

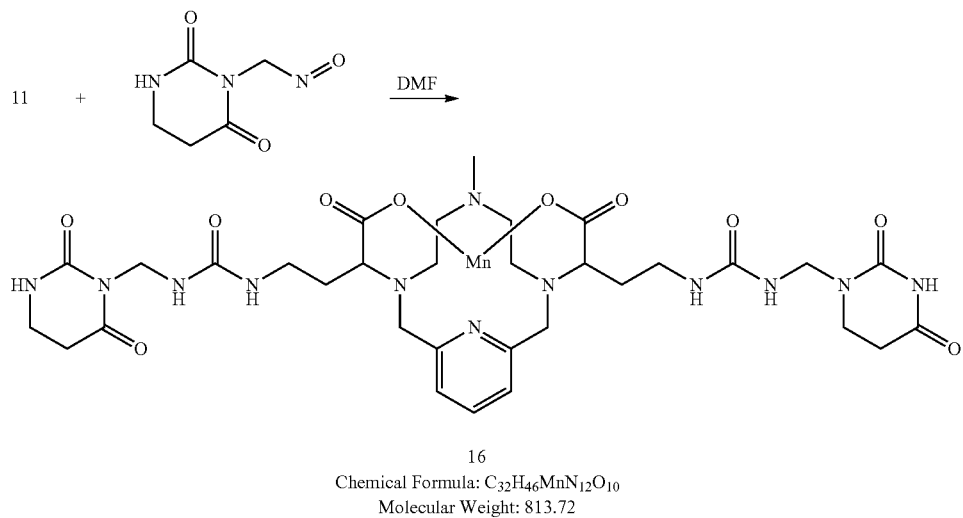

16
Chemical Formula: $C_{32}H_{46}MnN_{12}O_{10}$
Molecular Weight: 813.72

A solution of 11 in degassed DMF is added to 3-(isocyanatomethyl)dihydropyrimidine-2,4(1H,3H)-dione (2 equivalents) in DMF. The reaction mixture is stirred for several hours at room temperature and its progress is monitored using analytical chromatographic techniques. The addition of excess 3-(isocyanatomethyl)dihydropyrimidine-2,4(1H,3H)-dione may be necessary to drive the reaction to completion. The product 16 is purified using reversed phase chromatography on C-18 functionalized silica gel and eluting with water-acetonitrile or water-methanol mixtures.

Synthesis of Conjugate 17

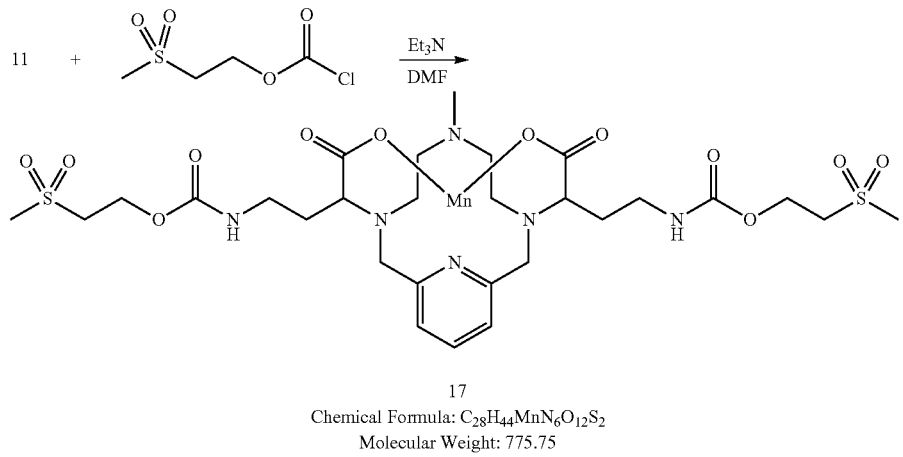

17
Chemical Formula: $C_{28}H_{44}MnN_6O_{12}S_2$
Molecular Weight: 775.75

A solution of 2-(methylsulfonyl)ethyl carbonochloridate in DMF (2 equivalents) is added to a solution of 11 and triethylamine (2.5 equivalents) in DMF at 0° C. The solution is allowed to warm to room temperature overnight. Analytical chromatographic procedures are used to ascertain reaction progress. Additional portions of 2-(methylsulfonyl) ethyl carbonochloridate may be required to drive the reaction to completion. Upon completion, the solvent is removed under reduced pressure, the residue is purified using reversed phase chromatography on C-18 functionalized silica gel and eluting with water-acetonitrile or water-methanol mixtures to provide the title compound 17.

Synthesis of the Amine Functionalized Chelate 18

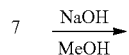

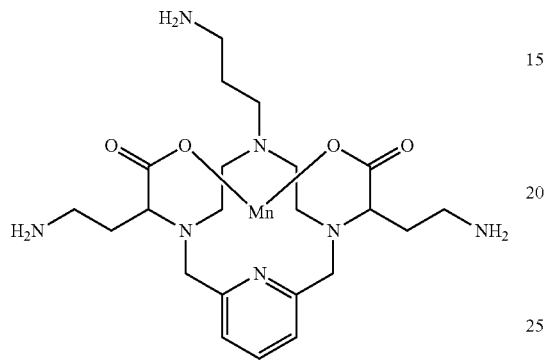

18
Chemical Formula: $C_{22}H_{37}MnN_7O_4$
Molecular Weight: 518.51

The trisisocyanate 7 is dissolved in anhydrous methanol at room temperature. Subsequently a solution of NaOH in methanol is added to hydrolyze the resulting trismethyl carbamate. The progress if the reaction is monitored by analytical chromatography. Upon completion, the reaction pH is adjusted to 7 and the solvent is removed under reduced pressure. If necessary, the isolated residue can by purified using reversed phase chromatography on C-18 functionalized silica gel and eluting with water-acetonitrile or water-methanol mixtures to provide pure 18.

Synthesis of the Conjugate 19

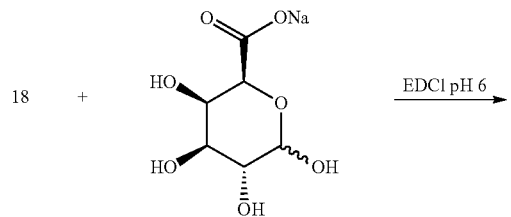

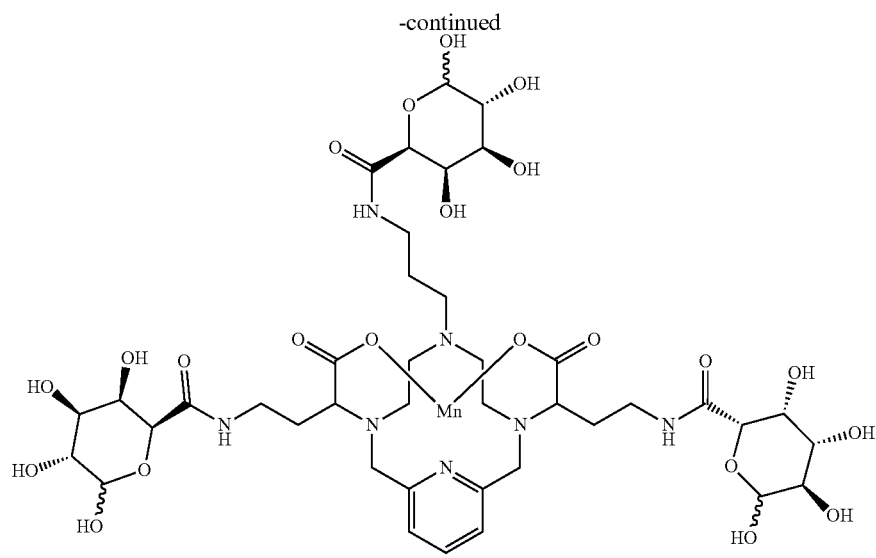

19
Chemical Formula: $C_{40}H_{61}MnN_7O_{22}$
Molecular Weight: 1046.88

The aminopyramine 18 is dissolved in water and D-Galacturonic acid sodium salt (3.1 eq) and EDCl-HCl (3.1 eq) are added. The pH is adjusted to 6.5 with HCl and HOBt (0.6 eq) is then added. The pH of the resulting solution is maintained at approximately 6 while stirring for 16 h. Additional EDCl-HCl (1.6 eq) is then added, and the reaction pH is maintained at pH approximately 6 and is stirred for an additional 16 h. The solvent is removed in vacuo and the desired compound 19 is further purified using reversed phase chromatography on C-18 functionalized silica gel and eluting with water-acetonitrile or water-methanol mixtures.

Synthesis of the Conjugate 20

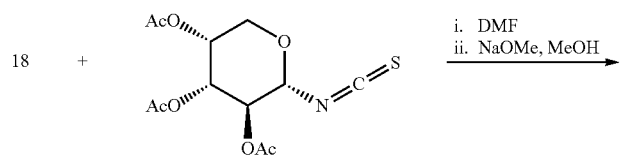

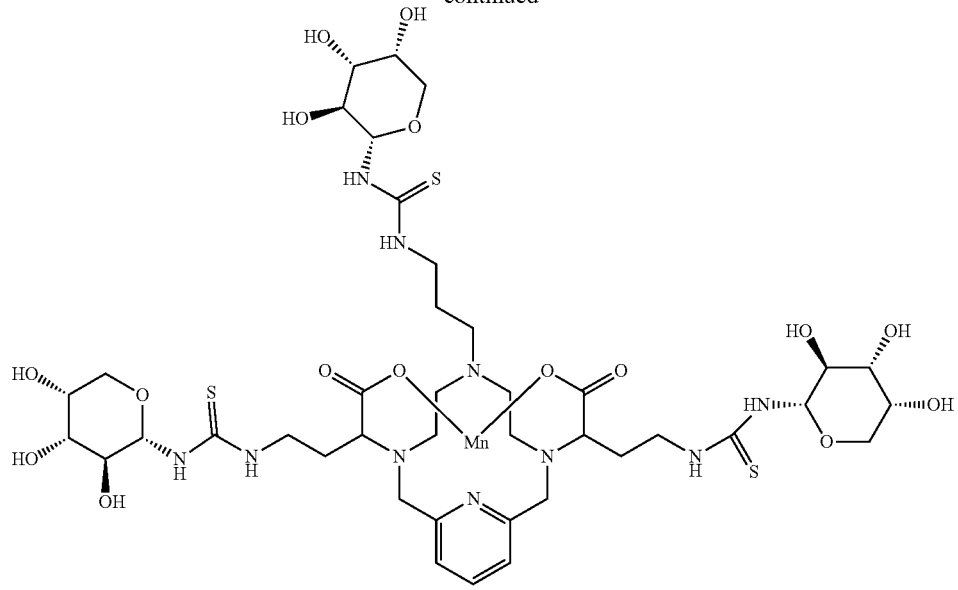

20
Chemical Formula: $C_{40}H_{64}MnN_{10}O_{16}S_3$
Molecular Weight: 1092.13

A solution of 2,3,4-tri-O-acetyl-α-D-arabinopyranosylisothiocyanate in degassed DMF (3.1 equivalents) is added to the triamine 18 in DMF. The reaction mixture is stirred for several hours at room temperature and its progress is monitored using analytical chromatographic techniques. The addition of excess isothiocyanate may be necessary to drive the reaction to completion. Upon completion, the reaction mixture is concentrated under reduced pressure, and the residue is taken up in a solution of methanol containing a catalytic quantity of sodium methoxide. The reaction is allowed to proceed until complete hydrolysis of the acetate protecting groups is observed. Once complete, the reaction mixture is concentrated under reduced pressure, and the residue is purified using reversed phase chromatography on C-18 functionalized silica gel and eluting with water-acetonitrile or water-methanol mixtures.

Synthesis of the Conjugate 21

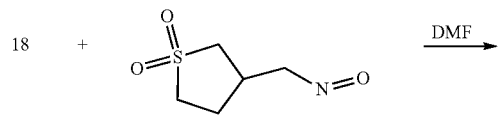

-continued

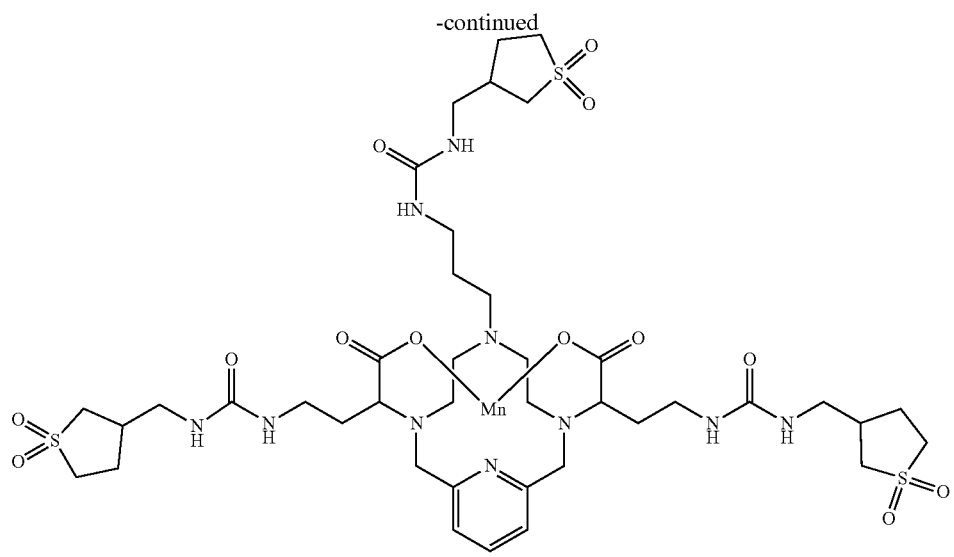

21
Chemical Formula: $C_{40}H_{64}MnN_{10}O_{13}S_3$
Molecular Weight: 1044.13

A solution of 18 in degassed DMF is added to 3-(isocyanatomethyl)tetrahydrothiophene 1,1-dioxide (3 equivalents) in DMF. The reaction mixture is stirred for several hours at room temperature and its progress is monitored using analytical chromatographic techniques. The addition of excess 3-(isocyanatomethyl)tetrahydrothiophene 1,1-dioxide may be necessary to drive the reaction to completion. The product 21 is purified using reversed phase chromatography on C-18 functionalized silica gel and eluting with water-acetonitrile or water-methanol mixtures.

Synthesis of the Conjugate 22

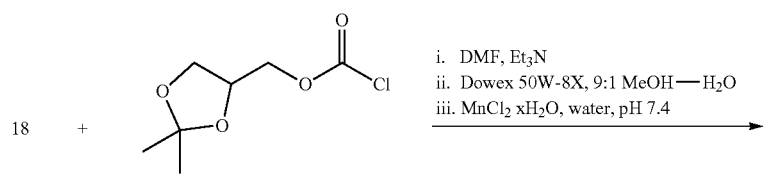

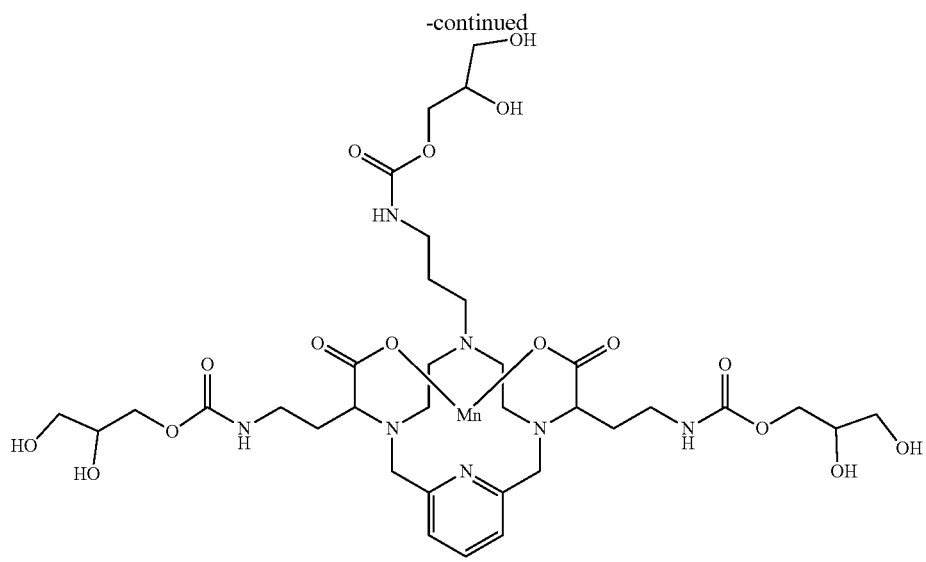

22
Chemical Formula: $C_{34}H_{55}MnN_7O_{16}$
Molecular Weight: 872.78

A solution of (2,2-dimethyl-1,3-dioxolan-4-yl)methyl carbonochloridate in DMF (3 equivalents) is added to a solution of 18 and triethylamine (3.5 equivalents) in DMF at 0° C. The solution is allowed to warm to room temperature over 16 h. Analytical chromatographic procedures are used to ascertain reaction progress. Additional portions of (2,2-dimethyl-1,3-dioxolan-4-yl)methyl carbonochloridate may be required to drive the reaction to completion. Upon completion, the solvent is removed under reduced pressure, and the residue is taken up in 9:1 MeOH—$H_2O$ and Dowex 50W-8X resin is added. The heterogeneous mixture is stirred at room temperature and progress of the reaction is assessed by analytical chromatography. Upon completion, the resin is removed by filtration and the filtrate is concentrated under reduced pressure. The residue is taken up in water and the pH of the mixture is adjusted to 7.4. Additional $MnCl_2 \cdot xH_2O$ (1 equivalent) is added and the mixture is stirred at room temperature. Additional NaOH solution is added to the reaction mixture to maintain the pH of the reaction mixture between 7.0 and 7.4. The progress of the manganese incorporation is monitored by analytical chromatography, and upon completion, the reaction pH is adjusted to 12 by the addition of aqueous NaOH. The reaction mixture is allowed to continue stirring for 1 h at room temperature, and then the reaction mixture is filtered to remove solids and the filtrate is collected and its pH adjusted to 7.4 through the addition of an aqueous solution of HCl. The desired compound 22 is further purified using reversed phase chromatography on C-18 functionalized silica gel and eluting with water-acetonitrile or water-methanol mixtures.

Synthesis of Bisisothiocyanate 23

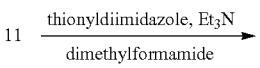

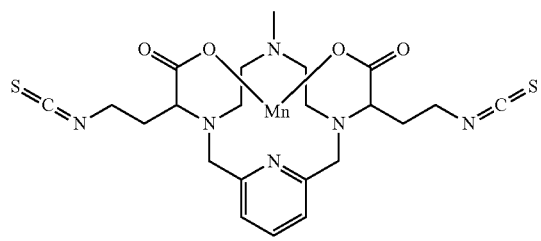

23
Chemical Formula: $C_{22}H_{28}MnN_6O_4S_2$
Molecular Weight: 559.56

The starting material 11 is suspended in degassed dimethylformamide. Triethylamine (2 equivalents) is added, followed by thionyldiimidazole (2 equivalents). The reaction mixture is stirred with heating at 80° C. until analytical chromatography indicates consumption of the starting material. The use of additional equivalents of triethylamine and thionyldiimidazole may be required to drive the reaction to completion. Once complete, the bisthioisocyanate 23 is used directly in subsequent reactions as a solution in DMF.

Synthesis of Bisthiourea 24

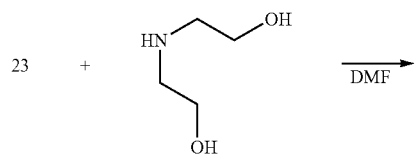

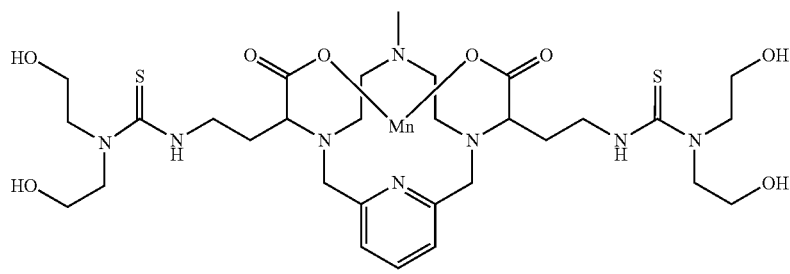

24
Chemical Formula: C$_{30}$H$_{50}$MnN$_8$O$_8$S$_2$
Molecular Weight: 769.83

To a solution of 23 in DMF at room temperature is added 2,2'-azanediyldiethanol (2.1 equivalents). The reaction mixture is allowed to continue stirring at room temperature and the progress of the reaction is monitored by analytical chromatography. The addition of excess 2,2'-azanediyldiethanol may be necessary to drive the reaction to completion. Upon completion, the solvent is removed under reduced pressure, the residue is purified using reversed phase chromatography on C-18 functionalized silica gel and eluting with water-acetonitrile or water-methanol mixtures to provide the title compound 24.

Synthesis of Conjugate 25

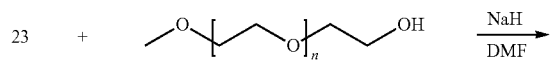

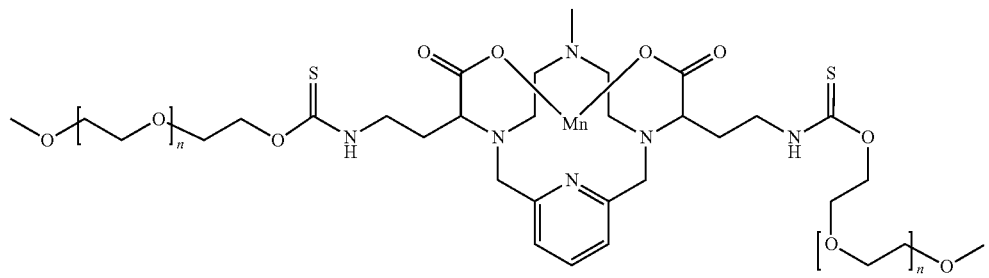

25

An oligopolyethylene glycol monomethylether (where n is between 0 and 150, and can be either a discrete chemical entity, or a mixture of chemical entities consisting of varying "n" values) is dissolved in DMF at 0° C. and treated with a substoichiometric amount of NaH. The mixture is stirred at 0° C. for 1 h, and then a solution of 23 in DMF is added to the mixture. The mixture is allowed to continue stirring, slowly warming to room temperature over several hours. The progress of the reaction is followed by analytical chromatography. On completion, the solvent is removed under reduced pressure, the residue is purified using reversed phase chromatography on C-18 functionalized silica gel and eluting with water-acetonitrile or water-methanol mixtures to provide the title compound 25.

Synthesis of Conjugate 26

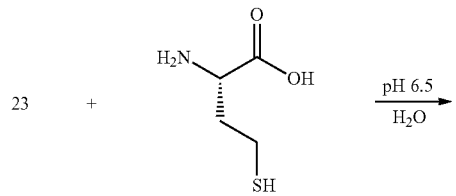

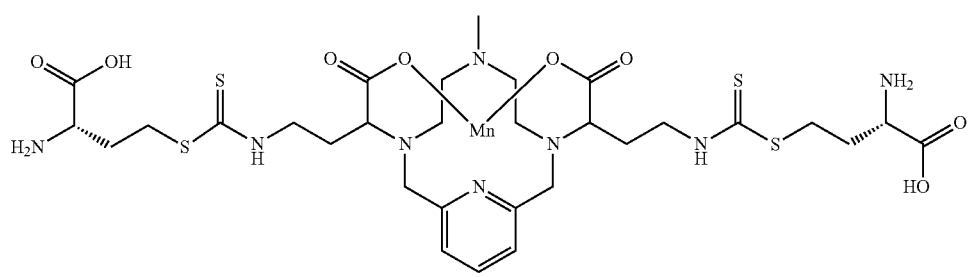

26
Chemical Formula: $C_{30}H_{46}MnN_8O_8S_4$
Molecular Weight: 829.93

A solution of 23 in DMF is added to a solution of homocysteine HCl in water. The pH of the solution is adjusted to 6.5 and the mixture is allowed to react and its progress monitored by analytical chromatography. Upon completion, the reaction mixture is concentrated to provide a crude residue that is further purified using reversed phase chromatography on C-18 functionalized silica gel and eluting with water-acetonitrile or water-methanol mixtures to provide the title compound 26.

Synthesis of Trisisothiocyanate 27

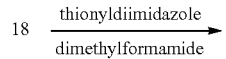

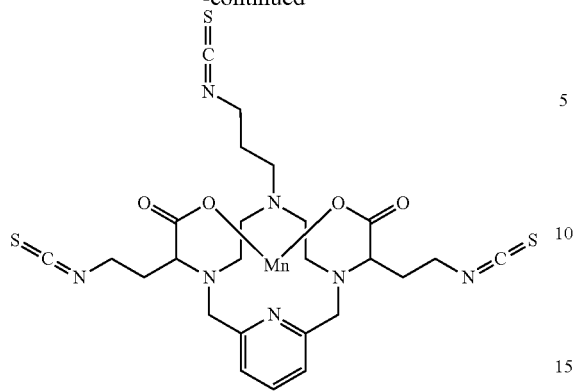

27
Chemical Formula: $C_{25}H_{31}MnN_7O_4S_3$
Molecular Weight: 644.69

The starting material 18 is suspended in degassed dimethylformamide. Triethylamine (3 equivalents) is added, followed by thionyldiimidazole (3 equivalents). The reaction mixture is stirred with heating at 80° C. until analytical chromatography indicates consumption of the starting material. The use of additional equivalents of triethylamine and thionyldiimidazole may be required to drive the reaction to completion. Once complete, the tristhioisocyanate 23 is used directly in subsequent reactions as a solution in DMF.

Synthesis of Conjugate 28

27 + 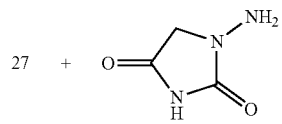 $\xrightarrow{\text{DMF}}$ 1-aminoimidazolidine-
2,4-dione

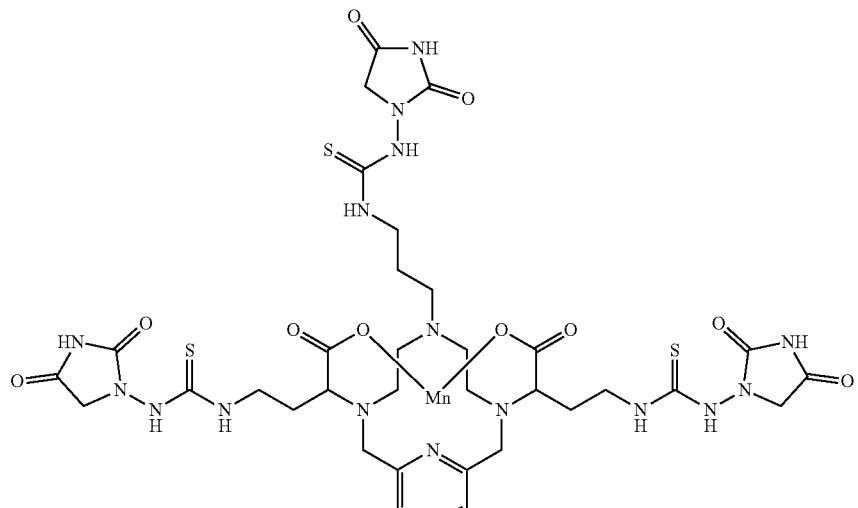

28
Chemical Formula: $C_{34}H_{46}MnN_{16}O_{10}S_3$
Molecular Weight: 989.96

To a solution of 27 in DMF at room temperature is added 1-aminoimidazolidine-2,4-dione (3.1 equivalents). The reaction mixture is allowed to continue stirring at room temperature and the progress of the reaction is monitored by analytical chromatography. The addition of excess 1-aminoimidazolidine-2,4-dione may be necessary to drive the reaction to completion. Upon completion, the solvent is removed under reduced pressure, the residue is purified using reversed phase chromatography on C-18 functionalized silica gel and eluting with water-acetonitrile or water-methanol mixtures to provide the title compound 28.

Synthesis of Coupling Partner 32

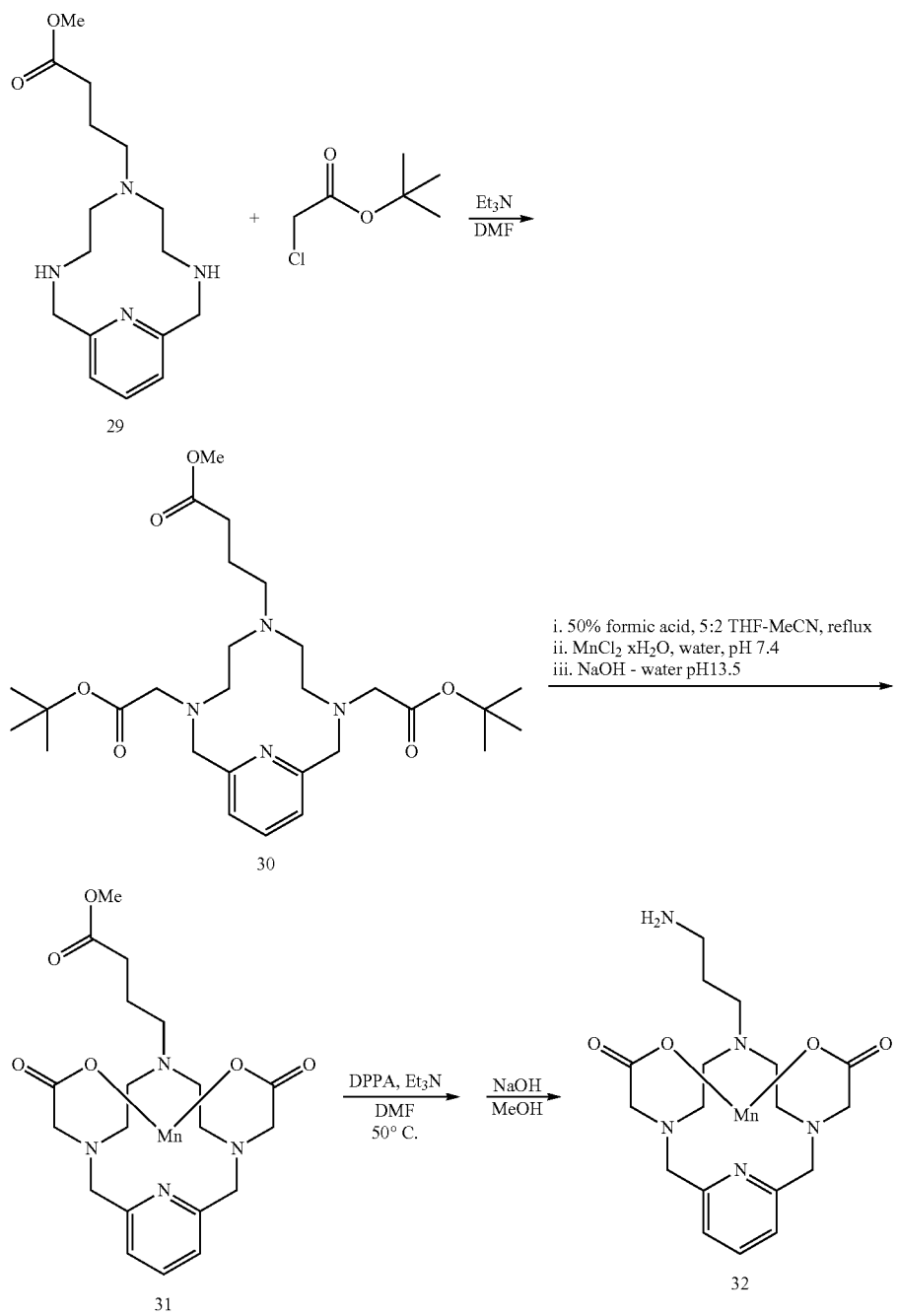

The starting material 29 is dissolved in DMF and triethylamine (3 equivalents) is added followed by tert-butylchloroacetate.

Synthesis of Conjugate 30

27 + 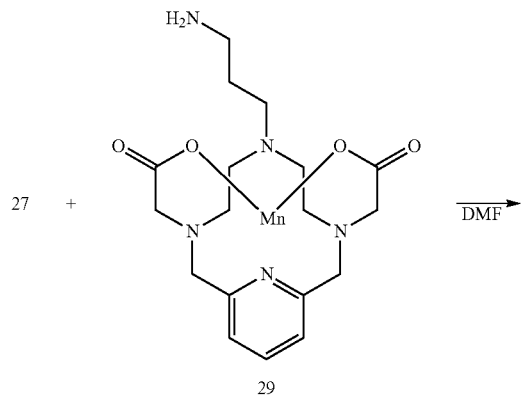 $\xrightarrow{\text{DMF}}$

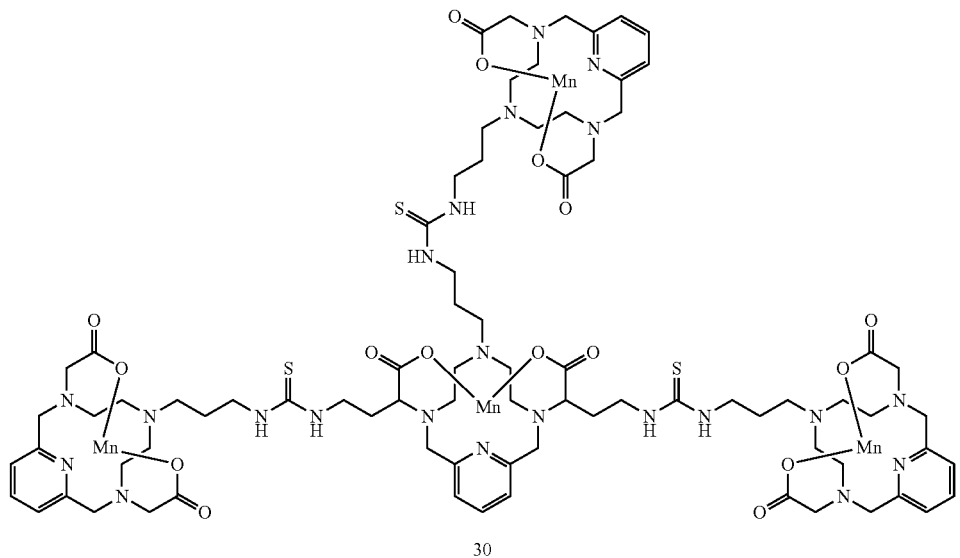

Chemical Formula: $C_{79}H_{112}Mn_4N_{22}O_{16}S_3$
Molecular Weight: 1941.82

To a solution of 27 in DMF at room temperature is added 29 (3.1 equivalents). The reaction mixture is allowed to continue stirring at room temperature and the progress of the reaction is monitored by analytical chromatography. The addition of excess 29 may be necessary to drive the reaction to completion. Upon completion, the solvent is removed under reduced pressure, the residue is purified using reversed phase chromatography on C-18 functionalized silica gel and eluting with water-acetonitrile or water-methanol mixtures to provide the title compound 30.

Synthesis of Conjugate 32

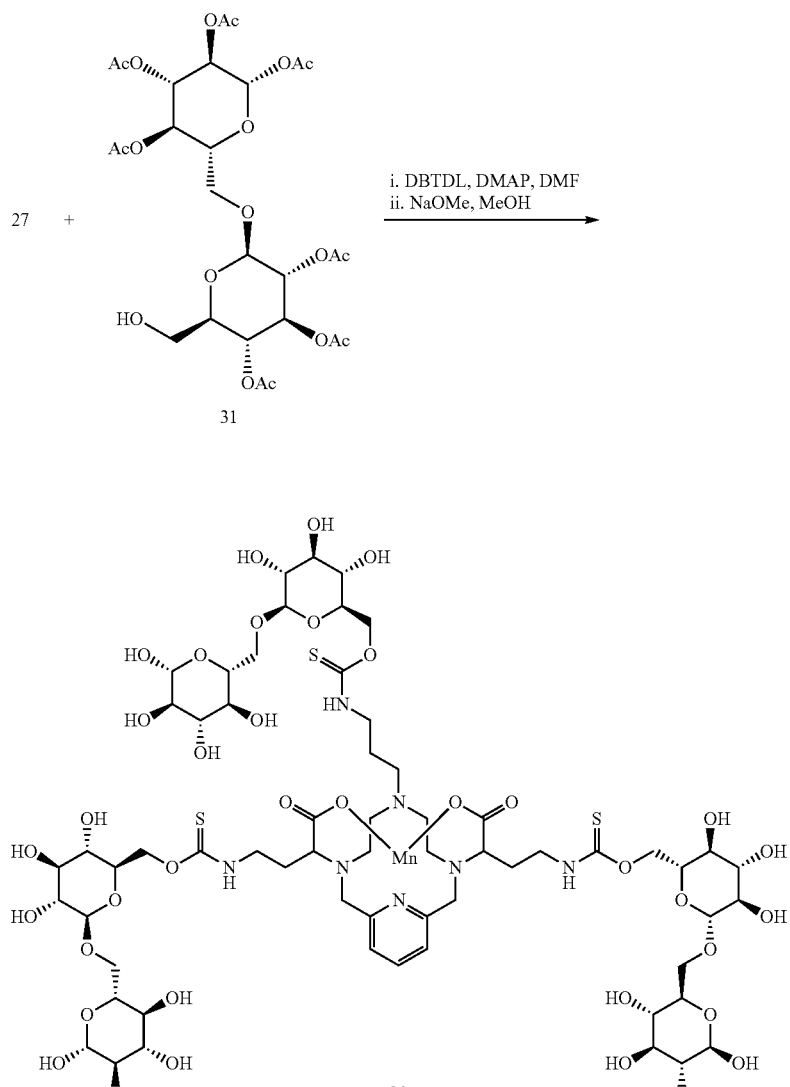

32
Chemical Formula: $C_{61}H_{97}MnN_7O_{37}S_3$
Molecular Weight: 1671.58

A solution of 31 in DMF (3 equivalents) is added to a solution of the isothiocyanate 27 in DMF containing 4-dimethylaminopyridine (0.3 eq), and dibutyltindilaurate (0.03 eq). The mixture is heated to 70° C. to drive the reaction to completion, analytical chromatographic procedures are used to ascertain reaction progress. Additional portions of 31 may be required to drive the reaction to completion. Upon completion, the solvent is removed under reduced pressure, the residue is suspended in a solution of methanol containing a catalytic quantity of sodium methoxide. The reaction is allowed to proceed until complete hydrolysis of the acetate protecting groups is observed. Once complete, the reaction mixture is concentrated under reduced pressure, and the residue is purified using reversed phase chromatography on C-18 functionalized silica gel and eluting with water-acetonitrile or water-methanol mixtures.

Synthesis of Conjugate 34

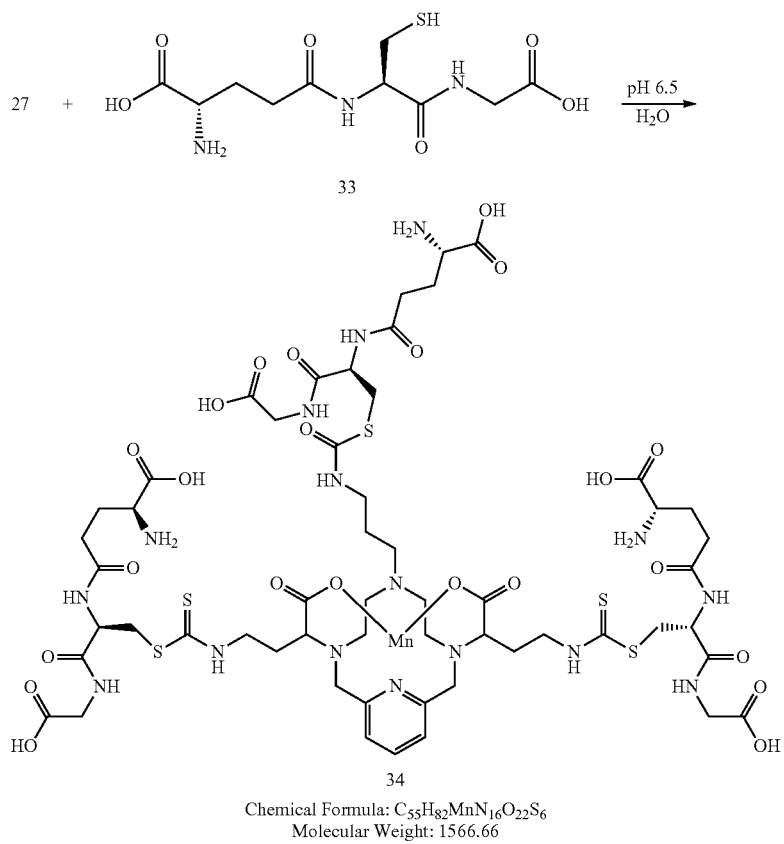

A solution of 27 in DMF is added to a solution of 33 in water. The pH of the solution is adjusted to 6.5 and the mixture is allowed to react and its progress monitored by analytical chromatography. Upon completion, the reaction mixture is concentrated to provide a crude residue that is further purified using reversed phase chromatography on C-18 functionalized silica gel and eluting with water-acetonitrile or water-methanol mixtures to provide the title compound 34.

Synthesis of the Diol 36

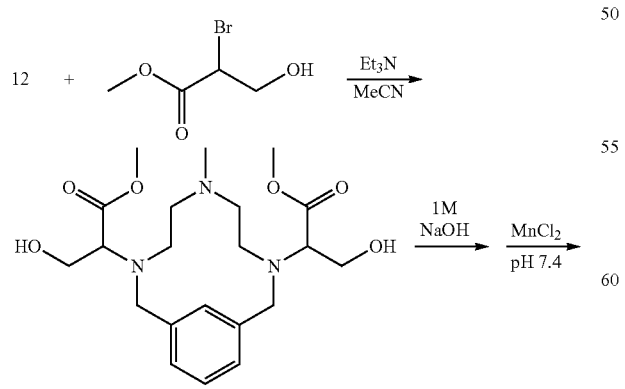

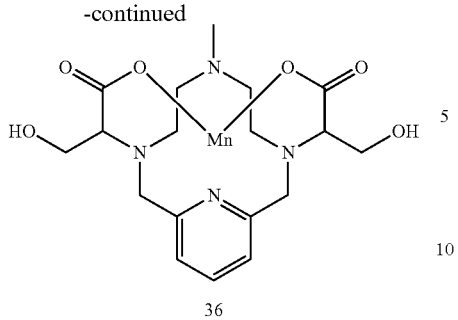

36

The pyramine 12 and methyl 2-bromo-3-hydroxypropanoate (2 equivalents) are dissolved in acetonitrile and triethylamine (2.2 equivalents) is added. The reaction is allowed to continue stirring at room temperature and the reaction progress to 35 is monitored using analytical chromatography. Upon completion, the reaction is concentrated under reduced pressure and the resulting residue is purified using reversed phase chromatography on C-18 functionalized silica gel by eluting with water acetonitrile or water-methanol mixtures to provide 35. The compound 35 is dissolved in water and solid NaOH is added (4 equivalents). The reaction is stirred at room temperature and its progress is monitored by analytical chromatography. Upon completion, a pH probe is added to the reaction mixture and the reaction pH is adjusted to 7.4 with an aqueous HCl solution. Upon achieving the desired pH, MnC12 xH$_2$O (~1.1 equivalents) is added to the reaction mixture and the mixture is stirred at room temperature. Additional NaOH solution is added to the reaction mixture to maintain the pH of the reaction mixture between 7.0 and 7.4. The progress of the manganese incorporation is monitored by analytical chromatography, and upon completion, the reaction pH is adjusted to 12 by the addition of aqueous NaOH. The reaction mixture is allowed to continue stirring for 1 h at room temperature, and then the reaction mixture is filtered to remove solids and the filtrate is collected and its pH adjusted to 7.4 through the addition of an aqueous solution of HCl. The desired compound 36 is further purified using reversed phase chromatography on C-18 functionalized silica gel and eluting with water-acetonitrile or water-methanol mixtures.

Synthesis of Conjugate 37

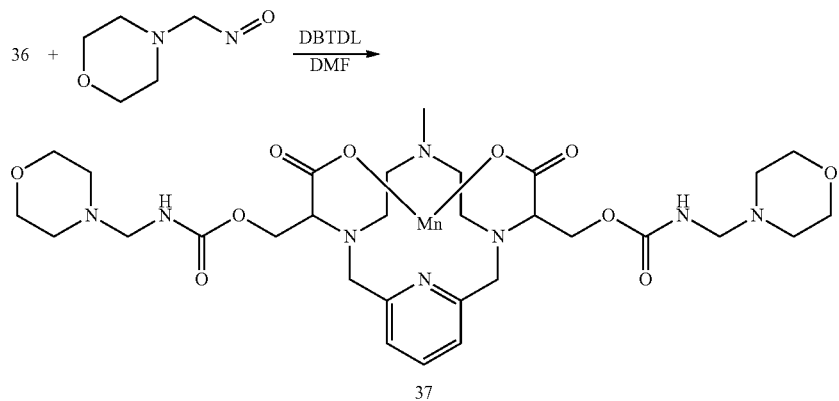

37

Chemical Formula: C$_{30}$H$_{46}$MnN$_8$O$_{10}$
Molecular Weight: 733.67

A solution of 36 in DMF is added to a solution of 4-(isocyanatomethyl)morpholine (2.1 equivalents) in DMF. A catalytic amount of dibutyltin dilaurate is added to the reaction mixture and the mixture is heated to 70° C. to drive the reaction to completion, analytical chromatographic procedures are used to ascertain reaction progress. If necessary, additional 4-(isocyanatomethyl)morpholine is added to the reaction mixture. Once complete, the reaction mixture is concentrated under reduced pressure, and the residue is purified using reversed phase chromatography on C-18 functionalized silica gel and eluting with water-acetonitrile or water-methanol mixtures to provide 37.

Synthesis of Conjugate 38

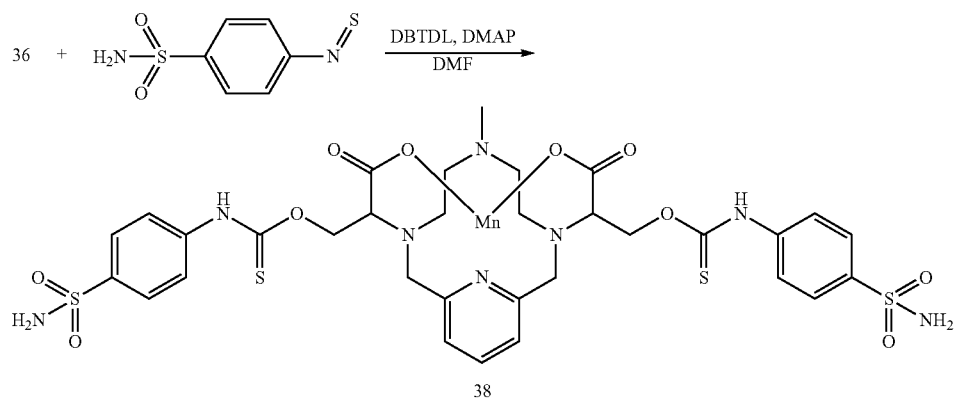

38

Chemical Formula: $C_{32}H_{38}MnN_8O_{10}S_4$
Molecular Weight: 877.89

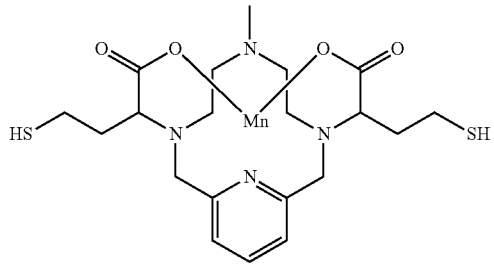

40

A solution of 4-isothiocyanatobenzenesulfonamide in DMF (2.1 equivalents) is added to a solution of the 36 in DMF containing 4-dimethylaminopyridine (0.3 eq), and dibutyltindilaurate (0.03 eq). The mixture is heated to 70° C. to drive the reaction to completion, analytical chromatographic procedures are used to ascertain reaction progress. Additional portions of 4-isothiocyanatobenzenesulfonamide may be required to drive the reaction to completion. Once complete, the reaction mixture is concentrated under reduced pressure, and the residue is purified using reversed phase chromatography on C-18 functionalized silica gel and eluting with water-acetonitrile or water-methanol mixtures.

Synthesis of Dithiol 40

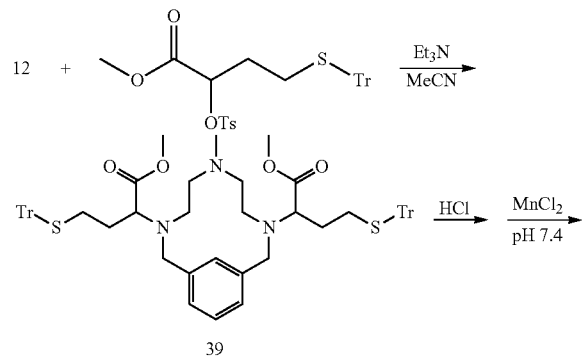

39

The pyramine 12 and methyl 2-(tosyloxy)-4-(tritylthio)butanoate (2 equivalents) are dissolved in acetonitrile and triethylamine (2.2 equivalents) is added. The reaction is allowed to continue stirring at room temperature and the reaction progress to 39 is monitored using analytical chromatography. Upon completion, the reaction is concentrated under reduced pressure and the resulting residue is purified using reversed phase chromatography on C-18 functionalized silica gel by eluting with water acetonitrile or water-methanol mixtures to provide 39. The protected compound 39 is dissolved 2M aqueous HCl that is carefully degassed under nitrogen before use. The reaction is heated under inert atmosphere promote hydrolysis of the methyl ester and cleavage of the trityl thioether. The progress of this reaction is monitored by analytical chromatography, on completion, the pH of the reaction mixture is adjusted to 7.4 through the addition of degassed 2M NaOH solution. Upon achieving the desired pH, $MnCl_2$ $xH_2O$ (~1.0 equivalents) is added to the reaction mixture and the mixture is stirred at room temperature. Additional NaOH solution is added to the reaction mixture to maintain the pH of the reaction mixture between 7.0 and 7.4. The progress of the manganese incorporation is monitored by analytical chromatography, and upon completion, the reaction pH is adjusted to 12 by the addition of aqueous NaOH. The reaction mixture is allowed to continue stirring for 1 h at room temperature, and then the reaction mixture is filtered to remove solids and the filtrate is collected and its pH adjusted to 7.4 through the addition of a degassed aqueous solution of HCl. The desired compound 40 is further purified using reversed phase chromatography on C-18 functionalized silica gel and eluting with water-acetonitrile or water-methanol mixtures.

Synthesis of Conjugate 41

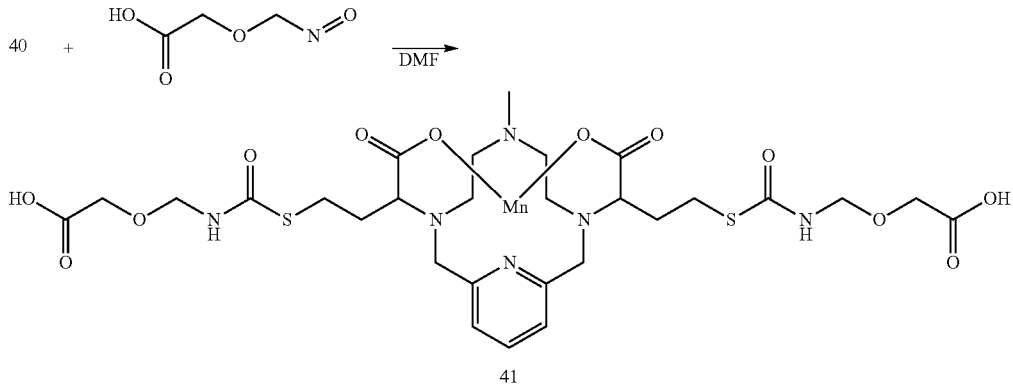

41

Chemical Formula: C$_{28}$H$_{40}$MnN$_6$O$_{12}$S$_2$
Molecular Weight: 771.72

A solution of 2-(isocyanatomethoxy)acetic acid (2 equivalents) and triethylamine (2 equivalents) in degassed DMF is added to a solution of 40 in degassed DMF. The reaction mixture is allowed to stir at room temperature and the progress of the reaction is monitored using analytical chromatography. Upon completion, the solvent is removed under reduced pressure, and the residue is purified using reversed phase chromatography on C-18 functionalized silica gel and eluting with water-acetonitrile or water-methanol mixtures.

Synthesis of Conjugate 42

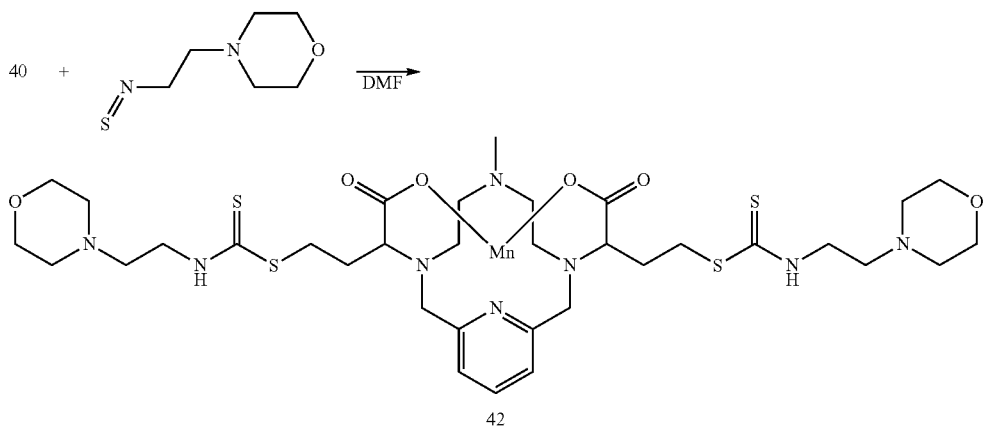

42

Chemical Formula: C$_{34}$H$_{54}$MnN$_8$O$_6$S$_4$
Molecular Weight: 854.04

4-(2-isothiocyanatoethyl)morpholine (2.1 equivalents is added to a solution of 40 in water. The pH of the solution is adjusted to 7.2 and the mixture is allowed to react and its progress monitored by analytical chromatography. Upon completion, the reaction mixture is concentrated to provide a crude residue that is further purified using reversed phase chromatography on C-18 functionalized silica gel and eluting with water-acetonitrile or water-methanol mixtures to provide the title compound 42.

Alternate Synthesis of 41

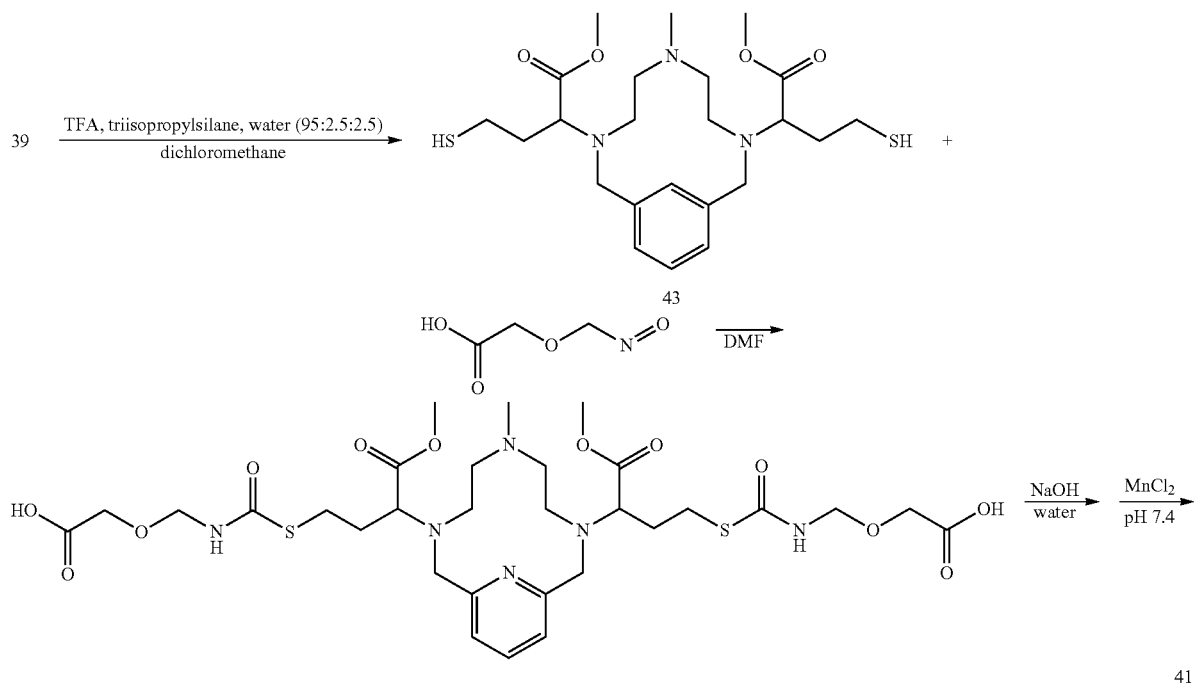

The intermediate 39 is dissolved in dichloromethane and added to a solution of trifluoroacetic acid, triisopropylsilane, and water (95:2.5:2.5 v/v/v). The reaction mixture is allowed to react at room temperature, and the progress of the reaction is monitored by analytical chromatography. On completion, the reaction mixture is concentrated to provide a crude residue that is further purified using reversed phase chromatography on C-18 functionalized silica gel and eluting with water-acetonitrile or water-methanol mixtures to provide the title compound 43. A solution of 2-(isocyanatomethoxy)acetic acid (2 equivalents) and triethylamine (2 equivalents) in degassed DMF is added to a solution of 43 in degassed DMF. The reaction mixtureaction mixture is allowed to stir at room temperature and the progress of the reaction is monitored using analytical chromatography. Once complete, the solvent is removed under reduced pressure, and the residue is treated with 1M NaOH in water. Analytical chromatography is used to monitor hydrolysis of the methylesters. On completion, the pH of the reaction mixture is adjusted to 7.4 by the addition of 2M aqueous HCl and $MnCl_2$ $xH_2O$ (1.0 equivalents) is added to the reaction mixture and the mixture is stirred at room temperature. Additional NaOH solution is added to the reaction mixture to maintain the pH of the reaction mixture between 7.0 and 7.4. The progress of the manganese incorporation is monitored by analytical chromatography, and upon completion, the reaction pH is adjusted to 12 by the addition of aqueous NaOH. The reaction mixture is allowed to continue stirring for 1 h at room temperature, and then the reaction mixture is filtered to remove solids and the filtrate is collected and its pH adjusted to 7.4 through the addition of a degassed aqueous solution of HCl.

The desired compound 41 is further purified using reversed phase chromatography on C-18 functionalized silica gel and eluting with water-acetonitrile or water-methanol mixtures.

Alternate Synthesis of 42

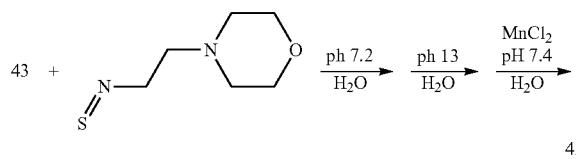

4-(2-isothiocyanatoethyl)morpholine (2.1 equivalents) is added to a solution of 43 in water. The pH of the solution is adjusted to 7.2 and the mixture is allowed to react and its progress monitored by analytical chromatography. On completion, the pH of the reaction mixture is raised to 13.5 by the addition of 2.0 M aqueous NaOH. Saponification of the methylesters is monitored by analytical chromatography. Once complete, the pH of the reaction mixture is lowered to 7.4 by the addition of 2M HCl solution and $MnCl_2 \cdot xH_2O$ (~1.0 equivalents) is added to the reaction mixture and the mixture is stirred at room temperature. Additional NaOH solution is added to the reaction mixture to maintain the pH of the reaction mixture between 7.0 and 7.4. The progress of the manganese incorporation is monitored by analytical chromatography, and upon completion, the reaction pH is adjusted to 12 by the addition of aqueous NaOH. The reaction mixture is allowed to continue stirring for 1 h at room temperature, and then the reaction mixture is filtered to remove solids and the filtrate is collected and its pH adjusted to 7.4 through the addition of a degassed aqueous solution of HCl. The desired compound 41 is further purified using reversed phase chromatography on C-18 functionalized silica gel and eluting with water-acetonitrile or water-methanol mixtures.

Synthesis of 51

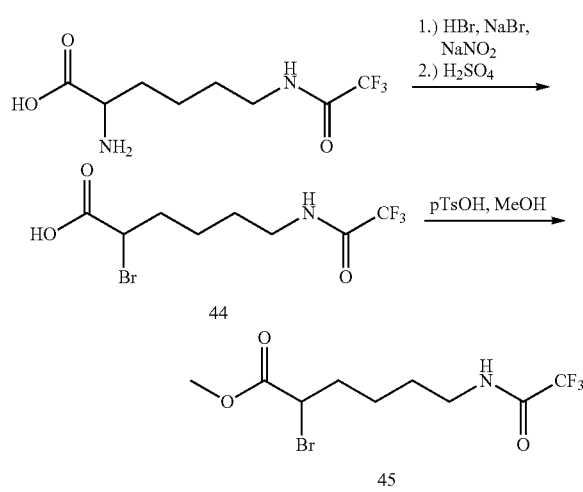

2-bromo-6-(2,2,2-trifluoroacetamido)hexanoic acid (44)

N-ε-trifluoroacetamido-L-lysine (25 g, 103.2 mmol) and sodium bromide (37.2 g, 361.2 mmol) were added to a 500 mL, 3-necked jacketed reaction vessel fitted with an internal thermocouple, mechanical stirrer, and a powder funnel. The solids were subsequently dissolved in 69 mL of water and aqueous HBr solution (20.9 mL, 8.9M). The powder funnel was removed and an addition funnel charged with sodium nitrite (12.8 g, 185.8 mmol) that had been predissolved in 16.5 mL of water fitted with a nitrogen inlet was added to the reaction vessel. The reaction exhaust was passed through a solution of sodium sulfite prior to being vented into the fume hood. The internal temperature of the reaction mixture was chilled to <0° C. and then the sodium nitrite solution was slowly added to the reaction mixture at such a rate that the internal reaction temperature was not allowed to exceed 3° C. Upon completion of the sodium nitrite addition the reaction mixture was nearly colorless. The addition funnel that contained the sodium nitrite solution was removed, and a second addition funnel preloaded with concentrated sulfuric acid (5.5 mL) was added to the reaction vessel. The sulfuric acid was added to the reaction mixture at such a rate that the internal reaction temperature did not exceed 5° C. The reaction mixture turned brown and evolved bromine during this addition. Following sulfuric acid addition, the addition funnel that contained the sulfuric acid was replaced with an active $N_2$ purge to remove evolved bromine from the reaction mixture and headspace. After sparging for 20 minutes at room temperature, the reaction mixture had lightened considerably. The active $N_2$ purge was discontinued, and the reaction mixture was partitioned against 80 mL of methyl-tert-butyl ether (MTBE). The mixture was rapidly stirred for five minutes, and then the phases were separated. The yellow-brown colored organic layer was collected, and the aqueous layer was extracted with two additional 70 mL portions of MTBE. The combined organic layers were washed with several portions of $Na_2SO_3$ solution until nearly colorless, and then subsequently washed with brine (100 mL), dried ($MgSO_4$), filtered and concentrated under reduced pressure to provide a pale yellow colored oil. The isolated material was dried under high vacuum overnight, and a sample was subsequently taken for analytical characterization (UPLC-MS demonstrated >80% conversion to 44 (m/z 306)) The isolated material was weighed, 28.1 g, and the residue was subsequently taken on to the next step without additional purification.

Methyl 2-bromo-6-(2,2,2-trifluoroacetamido)hexanoate (45)

Compound 44 (28.1 g) was dissolved in methanol (350 mL) and p-toluenesulfonic acid (0.35 g, 1.8 mmol) was added. The mixture was heated at 65° C. under nitrogen, overnight. Following this time, heating was stopped and the reaction mixture was allowed to cool to room temperature. The reaction mixture was concentrated under reduced pressure to provide a yellow oil that was subsequently purified by flash chromatography on silica gel (330 g column, 200 mL/min., elution with mixtures of ethyl acetate in hexanes) Gradient program was: initial condition 5% ethyl acetate in hexanes, hold 5% ethyl acetate in hexanes for 1 column volume, then execute a linear gradient to 50% ethyl acetate in hexanes over 12 column volumes, finally hold 50% ethyl acetate in hexanes for 2 additional column volumes. The column eluents were monitored by UV at 230 nm and 254 nm and by evaporative light scattering. The desired product eluted from the column between 6.4 and 9 column volumes. The isolated product was a colorless oil 20.3 g (63 mmol), $[\alpha]_{20.0}^{D}=-31.10\pm0.01$ (c=10.07 g/100 mL in MeOH), ESI-MS 322, 320 m/z; $^1$H NMR (CD$_3$CN, 599.79 MHz) δ 7.58 (br. s., 1H), δ 4.35 (t., 1H), δ 3.73 (s., 3H), δ 3.25 (dd., 2H), δ 2.08-2.02 (m., 1H), δ 1.99-1.93 (m., 1H), δ 1.61-1.53 (m., 2H), δ 1.51-1.44 (m., 1H), δ 1.40-1.33 (m., 1H); $^{13}$C NMR (CD$_3$CN, 150.83 MHz) δ 171.18, 157.83 (q., J=37.0 Hz), 117.17 (q., J=286.7 Hz), 53.57, 46.94, 40.03, 35.09, 28.59, and 25.01; $^{19}$F NMR (CD$_3$CN, 564.32 MHz) δ −76.67.
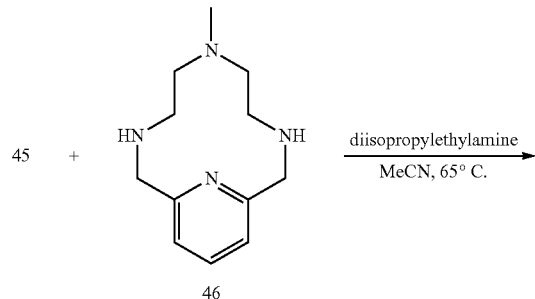
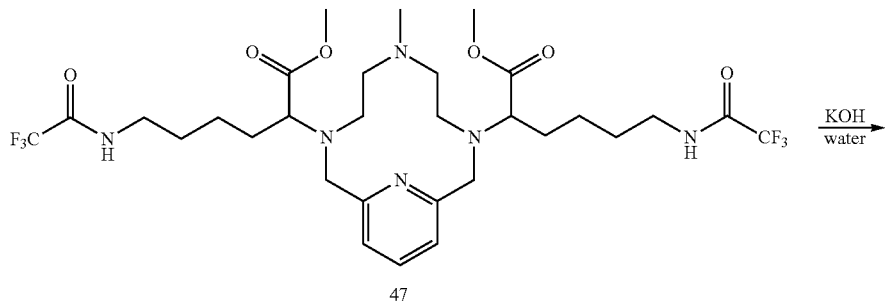
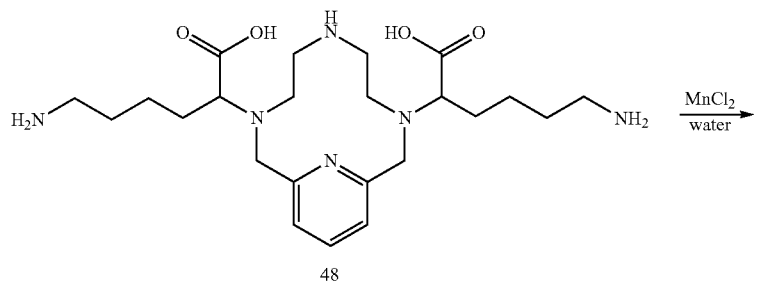
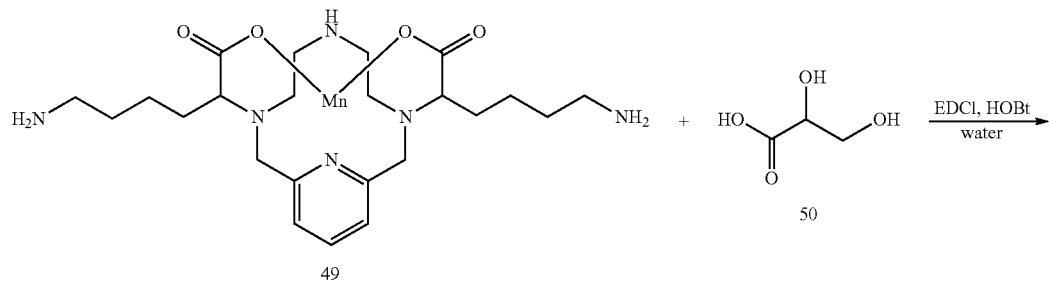

-continued

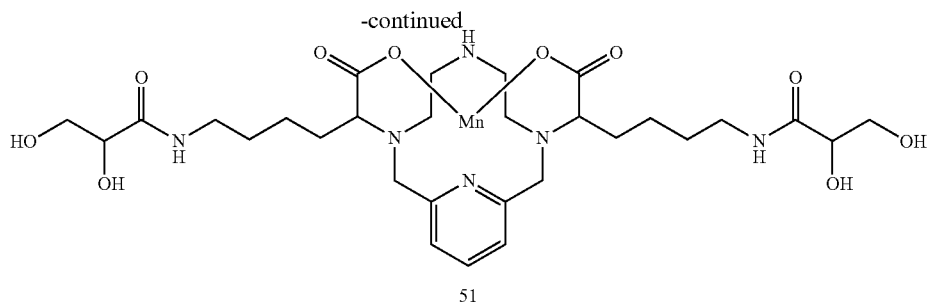

51

Compound (47) To a 100 mL flask containing the methylpyramine 46 (5 g, 21.7 mmol) was added 45 mL of anhydrous MeCN followed by 9.3 mL (52.1 mmol) diisopropylethylamine. After stirring for 5 minutes, 45 (15.3 g, 74.8 mmol) was added to the reaction mixture. The reaction vessel was placed in an oil bath maintained at 65° C. for 18 h. Following this time, an additional 1.9 mL (10.8 mmol) of diisopropylethylamine and 3 g (9.4 mmol) of 45 were added to the reaction mixture. The reaction was allowed to continue stirring in a 65° C. at oil bath for an additional 24 h. Following the allotted time, the reaction mixture was cooled to ambient temperature, and the reaction mixture was subsequently concentrated under reduced pressure to provide a red oily residue. The isolated residue was partitioned between ethyl acetate and water and the phases were separated. The organic layer was washed with two additional portions of water, and then the combined aqueous washings were back extracted with two additional portions of ethyl acetate. The combined organic extracts were dried ($Na_2SO_4$), filtered, and concentrated under reduced pressure to provide a red oil that foamed under vacuum. The isolated oil was triturated with triturated with two 40 mL portions of diethylether for 10 minutes at ambient temperature, and then the ether layer was decanted away and discarded. The residue was washed with 50 mL of water (heated for 10 min in a 60° C. water bath). The water suspension was allowed to cool to <35° C. and then the mixture was extracted with two 15 mL portions of diethylether. The ether extracts were discarded. The aqueous layer was diluted with an equivolume portion of brine and exhaustively extracted with ethyl acetate (extractions were continued until there was little to no signal for the product remaining in the aqueous layer by HPLC, (5×30 mL). The combined ethyl acetate extracts were dried ($Na_2SO_4$), filtered, and concentrated under reduced pressure to provide a nearly colorless foam 14.3 g (20.5 mmol, 94%), ESI-MS 699.70 (m/z).

Compound (48) To a 50 mL round bottomed flask fitted with a magnetic stir bar was added 47 (2.018 g, 2.89 mmol) and in $H_2O$ (9 mL). KOH (1.302 g, 23.2 mmol) was added and the resulting solution was stirred at ambient temperature for 1.5 h. HPLC-MS analysis showed complete reaction (ESI-MS: 479 (M+H+) (m/z)). The pH of the reaction solution was adjusted to 10.1 with conc. HCl and used without further purification.

Compound (49) $MnCl_2$-$4H_2O$ (0.638 g, 3.22 mmol) was added to the pH 10.1 solution described in the synthesis of compound 5 and the pH decreased to 5.8 and was adjusted to 7.0 with 3.4 M aqueous KOH. The resulting solution was then heated to 90° C. for 3 h before cooling to ambient temperature. The pH was then increased to 10.0 with KOH and the resulting cloudy brown solution was stirred at ambient temperature for 14.5 h. Filtration through a 0.45 µm PTFE filter gave a slightly cloudy filtrate which was concentrated to dryness in vacuo. The resulting brown residue was triturated with MeOH (10 mL) to give a white solid in a clear brown solution. The solid was removed via filtration through a 0.45 µm PTFE filter and the clear brown filtrate was concentrated to dryness in vacuo. The resulting brown residue was dissolved in $H_2O$ (5 mL) and purified on $C_{18}$ silica (5% AcN in water to 10% AcN in water) to give 1.41 g (92%) of the desired product as a pale yellow solid. ESI-MS: 532 (M+H+) (m/z).

Compound (51) 20 wt % aqueous 50 (1.651 mL, 3.11 mmol) was added to a 25 mL 2-necked flask fitted with a magnetic stir bar and a pH probe. The pH of the glyceric acid solution was adjusted from 2.2 to 7.2 with 3.4 M KOH. 49 (0.701 g, 1.38 mmol) was added followed by EDCl-HCl (0.634 g, 3.31 mmol) and hydroxybenzotriazole hydrate (0.028 g, 0.183 mmol). The pH of the resulting solution was maintained between 6 and 7 with the addition of 6M HCl and/or 3.4 M KOH as appropriate while stirring at ambient temperature for 4.5 h. EDCl-HCl (0.530 g, 2.76 mmol) was added and the resulting solution was stirred at ambient temperature for an additional 15.5 h. All solvent was removed in vacuo to give a golden yellow oil that was purified on C18 silica (2% AcN in water to 20% AcN in water) to afford 0.31 g (32%) of the desired product as an off white solid. ESI-MS: 708 $(M+^H)$ (m/z).

The invention claimed is:
1. A compound of Formula I or a salt or solvate thereof:

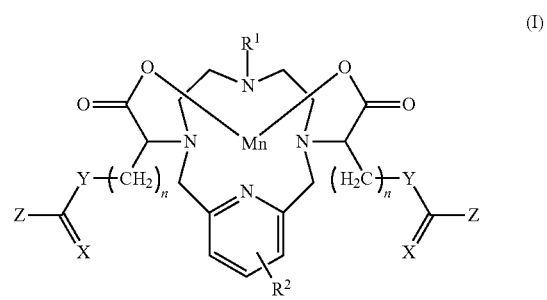

(I)

wherein:
X is O or S;
Y is O, S or Q-$R^3$ where Q is N or CH and $R^3$ is selected from $C_{1-20}$ hydroxyalkyl, $C_{1-6}$ alkyl or hydrogen;
Z is O-L-$R^4$, S-L-$R^4$ or Q-$R^3$-(L-$R^4$) where Q and $R^3$ are as defined for Y and L is an optional linker selected from $C_{1-6}$ alkylene, $C_{1-6}$ hydroxyalkylene or a PEG linker, $R^4$ is selected from $C_{1-6}$ alkyl-$R^5$, $C_{3-6}$ aryl-$R^5$, hydroxy, —O—$C_{1-3}$ alkyl-$R^5$, sulfonyl, a 5-6-membered heterocyclic ring, a carbohydrate moiety, a chelate moiety, or an amino acid moiety, wherein $R^5$ represents one or more optional substituents selected from hydroxy, amino, oxo, halo, $C_{1-3}$ alkyl, sulfonamide or —C(=O)—NH—$C_{1-6}$ hydroxyalkyl; or Z itself forms part of a carbohydrate moiety or a 5-6-membered heterocyclic ring;

$R^1$ is $C_{1-3}$ alkyl or -(CH$_2$)$_m$—Y$^1$—C(=X$^1$)—Z$^1$ wherein $X^1$, $Y^1$ and $Z^1$ are as defined for X, Y and Z and m is an integer from 2-5;

$R^2$ represents 0-3 substituents independently selected from hydroxy, halo, amino, amido, $C_{1-6}$ alkyl or $C_{1-6}$ hydroxyalkyl; and, each n is an integer from 0-15;

wherein the compound of Formula I comprises at least two hydroxy groups; and, with the proviso that when Y is Q-$R^3$ where Q is CH, Z is not Q-$R^3$-(L-$R^4$) where Q is N.

2. The compound as defined in claim 1 wherein X is O, Y is Q-$R^3$ wherein Q is N and Z is Q-$R^3$-(L-$R^4$) wherein Q is N.

3. The compound as defined in claim 1 wherein X is S, Y is Q-$R^3$ wherein Q is N and Z is Q-$R^3$-(L-$R^4$) wherein Q is N.

4. The compound as defined in claim 1 wherein X is O, either Y is O or Z is O-L-$R^4$ and when Y is not O it is Q-$R^3$ wherein Q is N and when Z is not O-L-$R^4$ it is Q-$R^3$-(L-$R^4$) wherein Q is N.

5. The compound as defined in claim 1 wherein X is S, either Y is O or Z is O-L-$R^4$ and when Y is not O it is Q-$R^3$ wherein Q is N and when Z is not O it is Q-$R^3$-(L-$R^4$) wherein Q is N.

6. The compound as defined in claim 1 wherein X is O, Y is Q-$R^3$ wherein Q is N and Z is Q-$R^3$-(L-$R^4$) wherein Q is CH.

7. The compound as defined in claim 1 wherein X is O, either Y is O or Z is O-L-$R^4$ and when Y is not O it is Q-$R^3$ wherein Q is CH and when Z is not O it is Q-$R^3$-(L-$R^4$) wherein Q is CH.

8. The compound as defined in claim 1 wherein each -L-$R^4$ is $C_{1-12}$ hydroxyalkyl.

9. The compound as defined in claim 1 wherein each -L-$R^4$ is independently selected from:

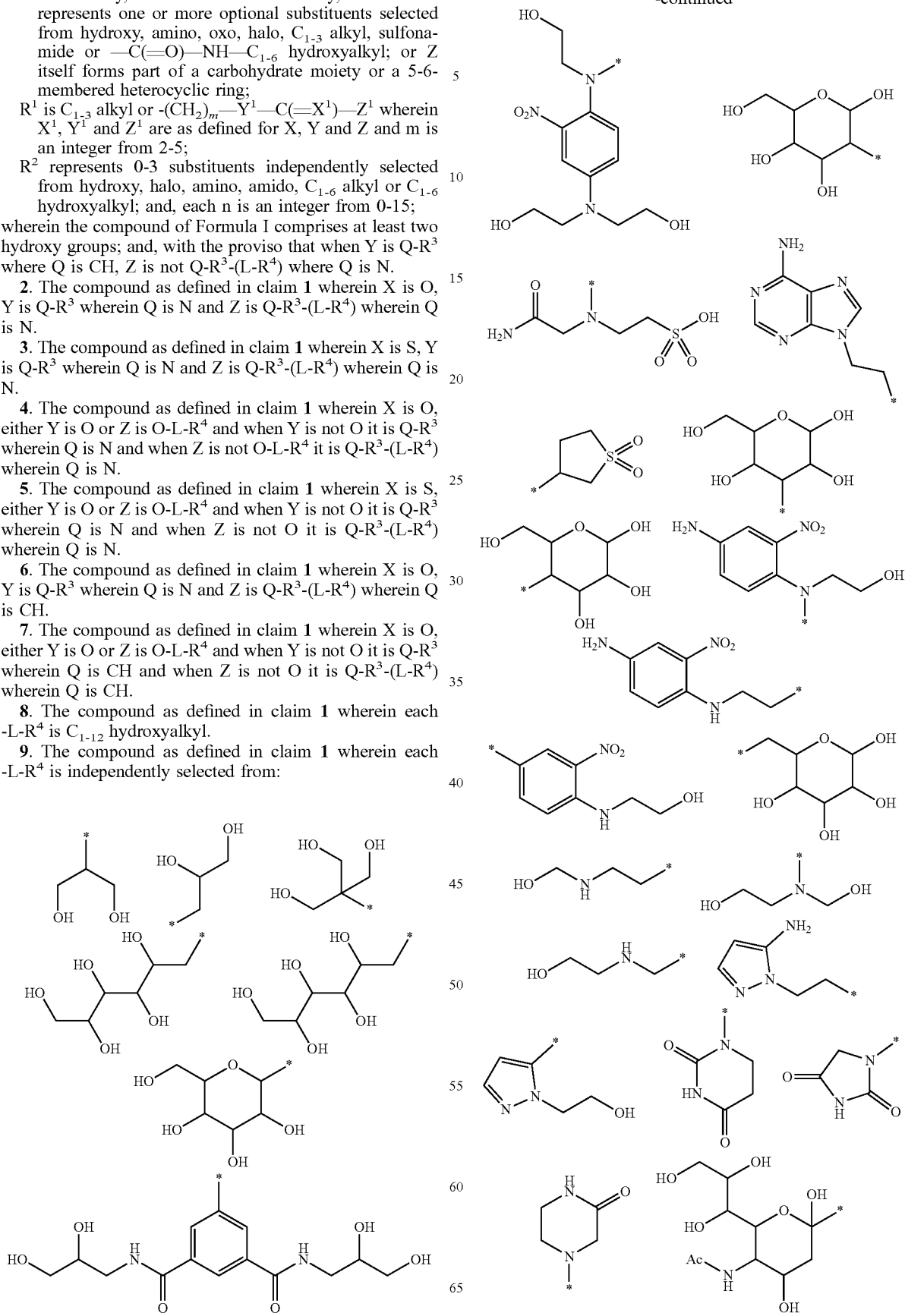

-continued

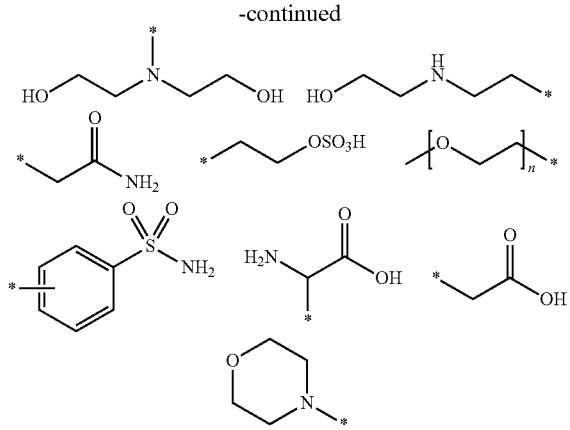

wherein in each case the asterisk denotes the point of attachment to the rest of the compound of Formula I.

10. The compound as defined in claim 1 wherein each $R^4$ is the same.

11. The compound as defined in claim 1 wherein each $R^3$ is independently selected $C_{1-3}$ alkyl or hydrogen.

12. The compound as defined in claim 11 wherein each $R^3$ is $C_{1-3}$ alkyl.

13. The compound as defined in claim 11 wherein each $R^3$ is hydrogen.

14. The compound as defined in claim 1 wherein each $R^3$ is the same.

15. The compound as defined in claim 1 as wherein each n is an integer from 1-6.

16. The compound as defined in claim 1 wherein m is 3.

17. The compound as defined in claim 1 wherein $R^1$ is $C_{1-3}$ alkyl.

18. The compound as defined in claim 1 wherein $R^1$ is —$(CH_2)_m$—Y—C(=X)—Z wherein X, Y, Z and m are as defined in any one of claims 1-16.

19. The compound as defined in claim 1 wherein $R^2$ represents 0 substituents.

20. The compound as defined in claim 1 wherein $R^2$ represents 2 hydroxy groups.

21. The compound as defined in claim 20 wherein said hydroxyl groups are at the meta positions on the pyridyl ring.

22. The compound as defined in claim 1 which comprises at least 4 hydroxy groups.

23. The compound as defined in claim 1 which is selected from the following compounds:

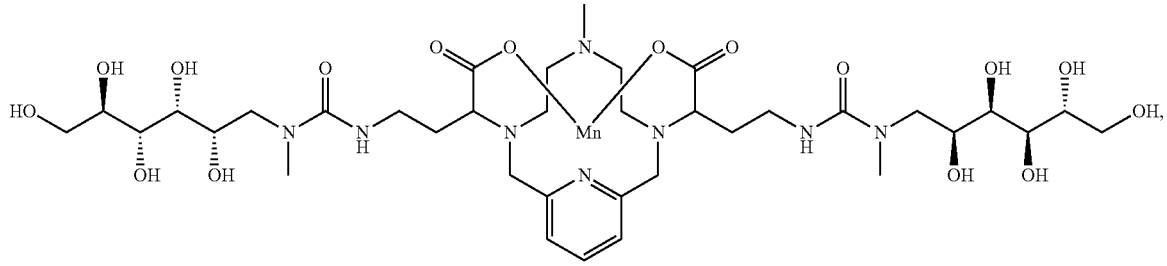

3

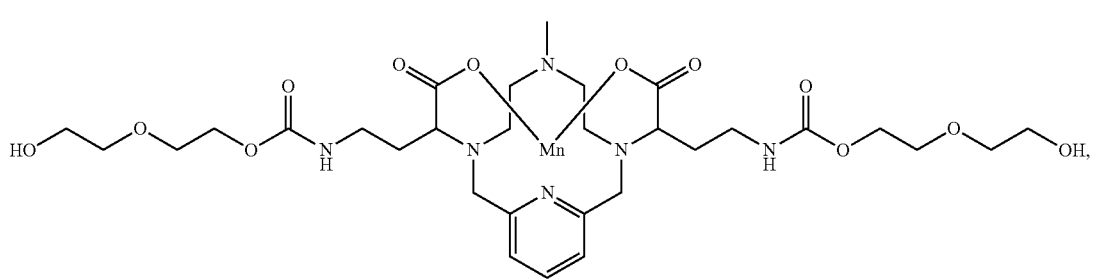

4

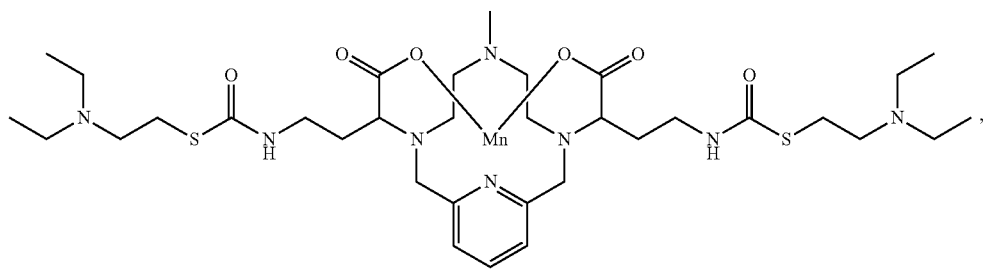

5

-continued
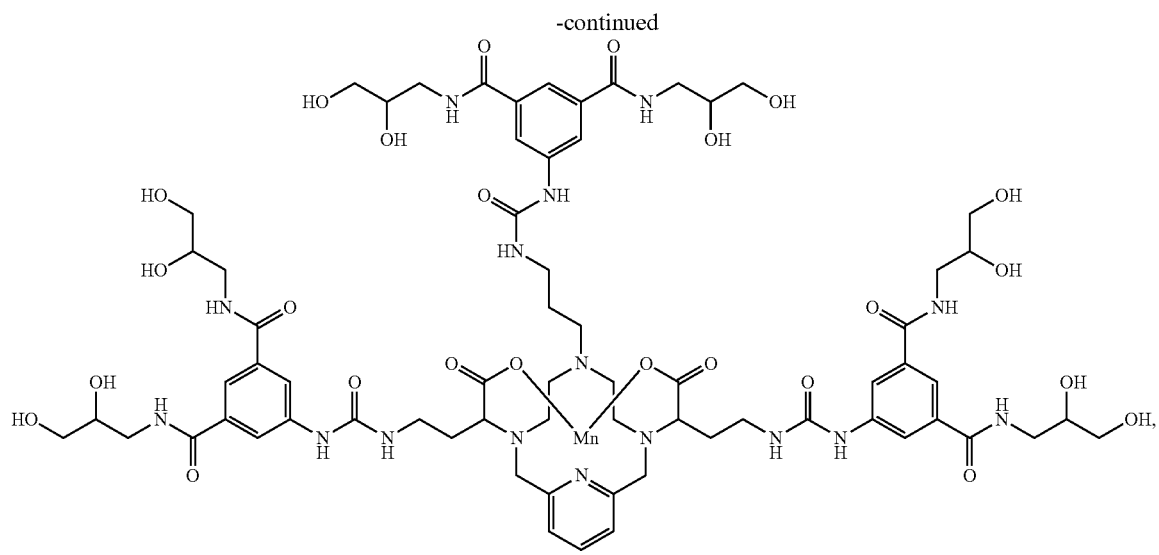
8
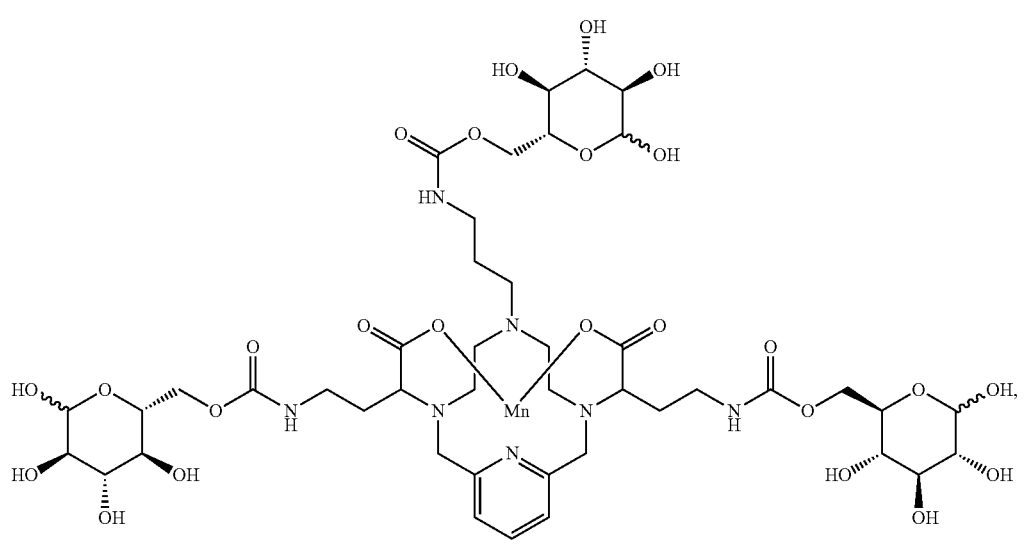
9
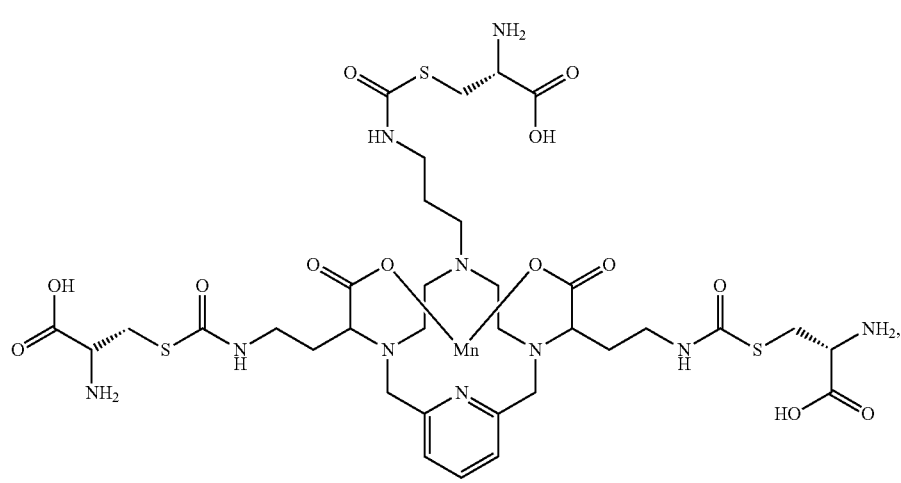
10

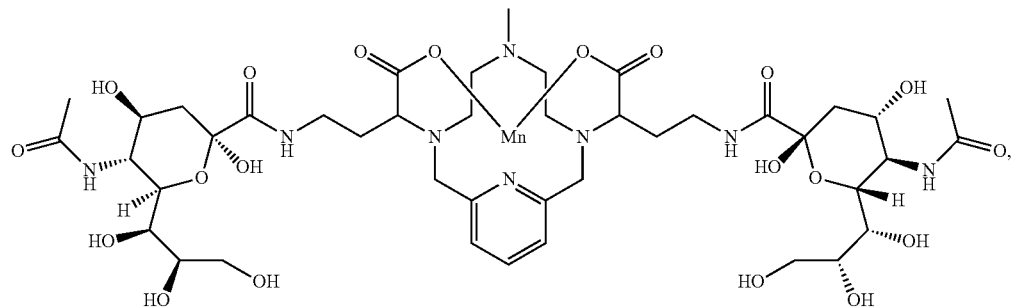
14
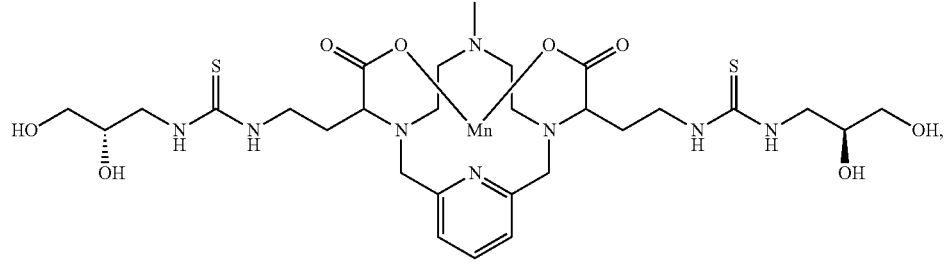
15
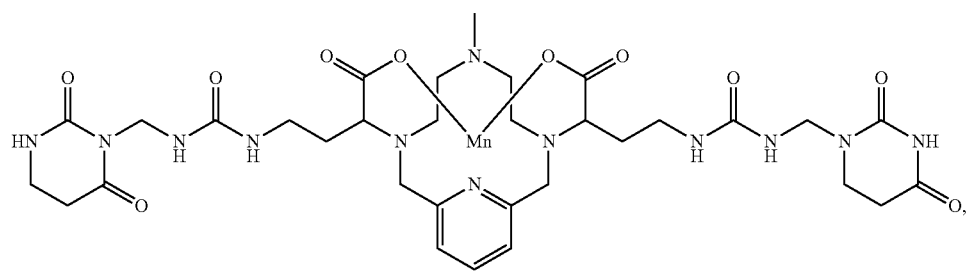
16
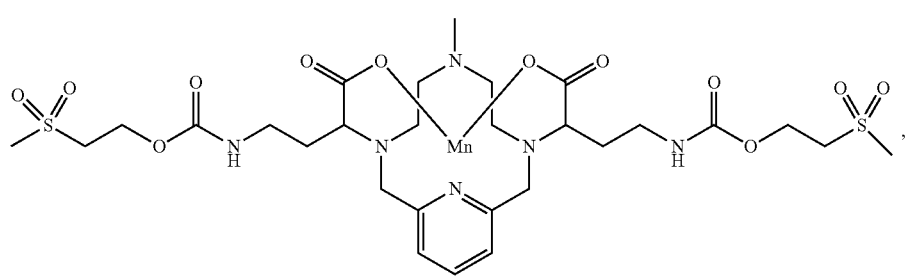
17
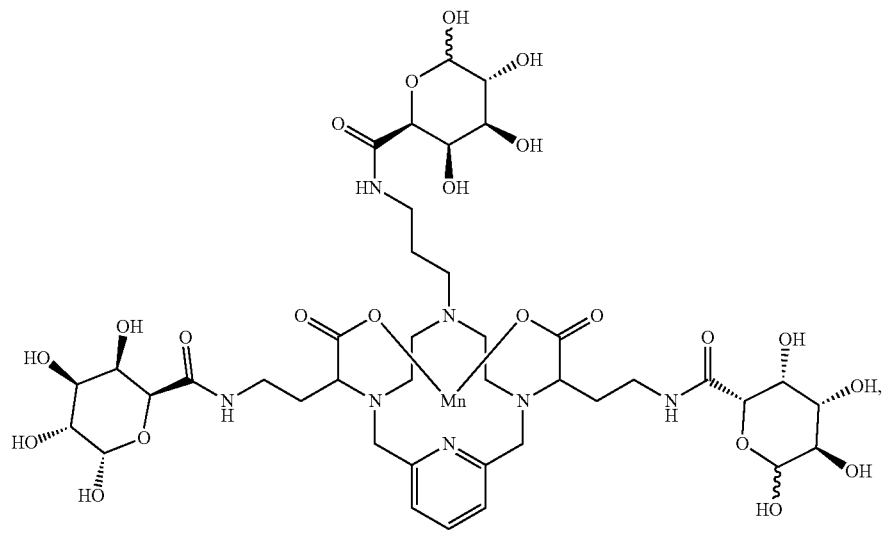
19

20
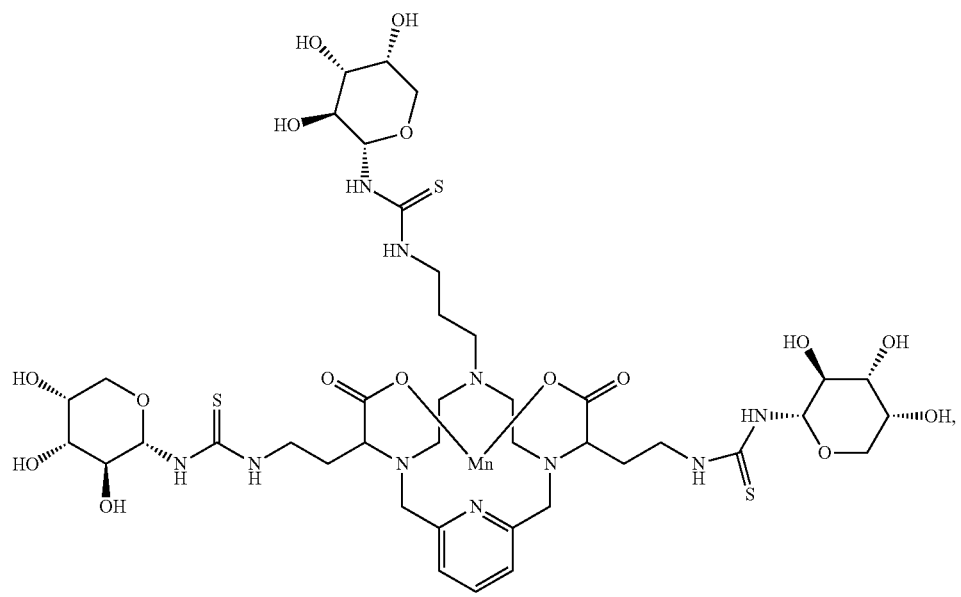
21
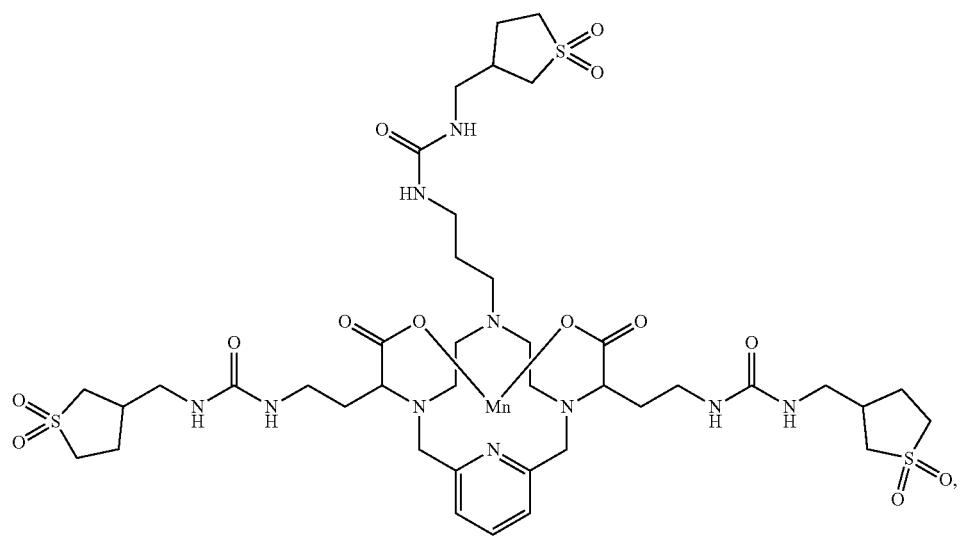
22
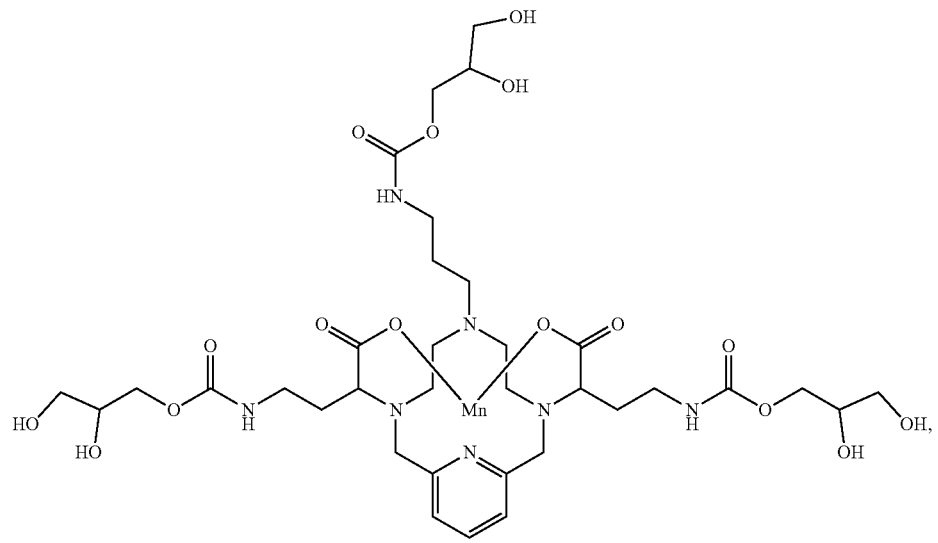

24
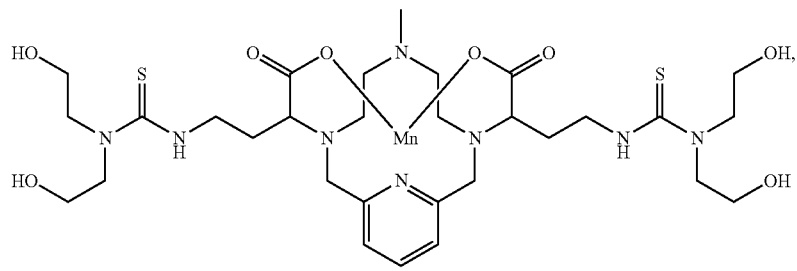
25
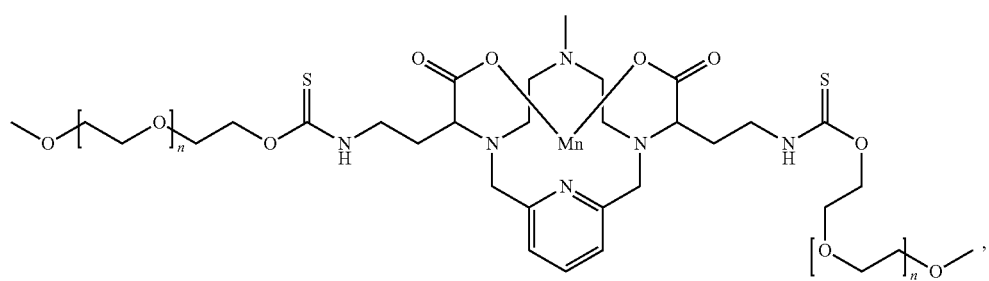
26
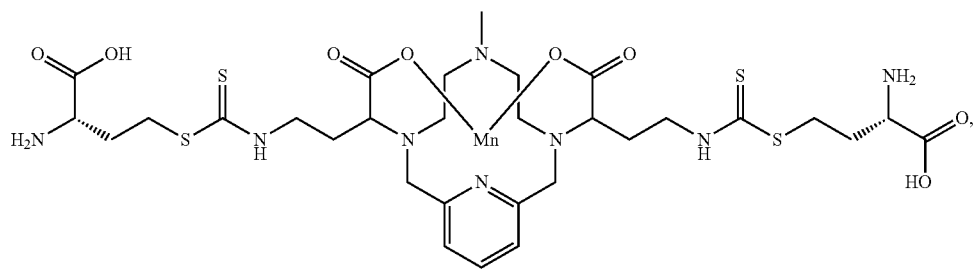
28
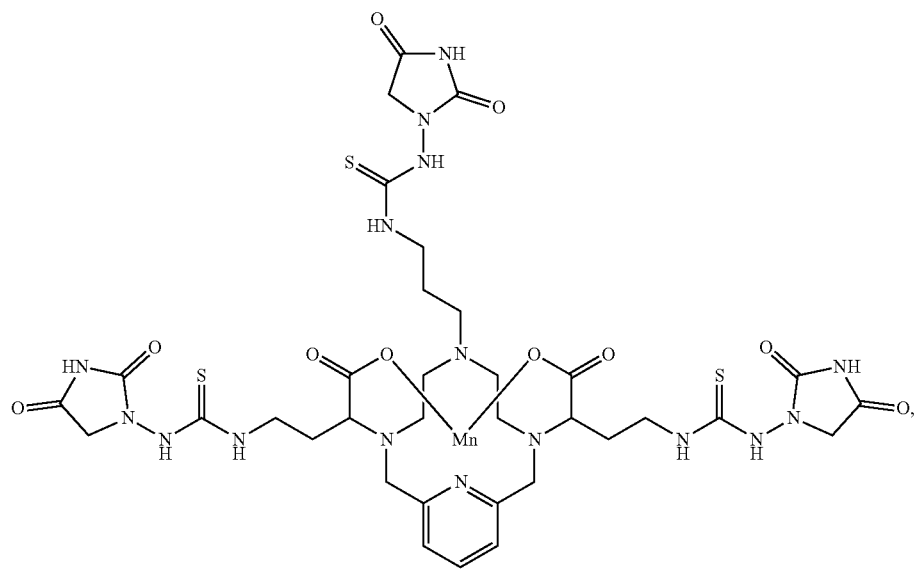

-continued
101
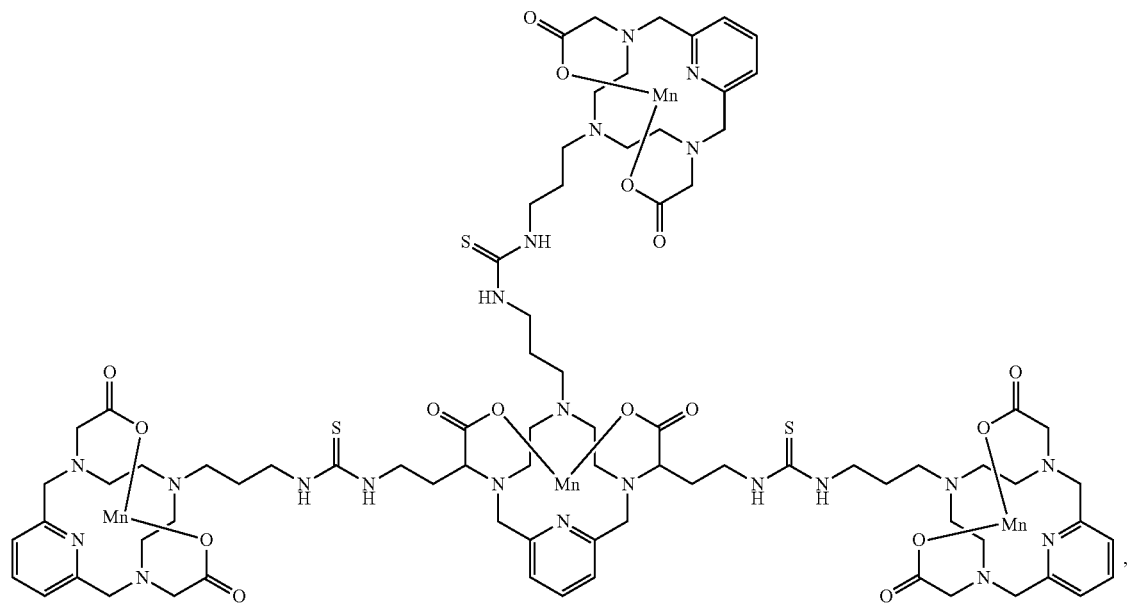
102
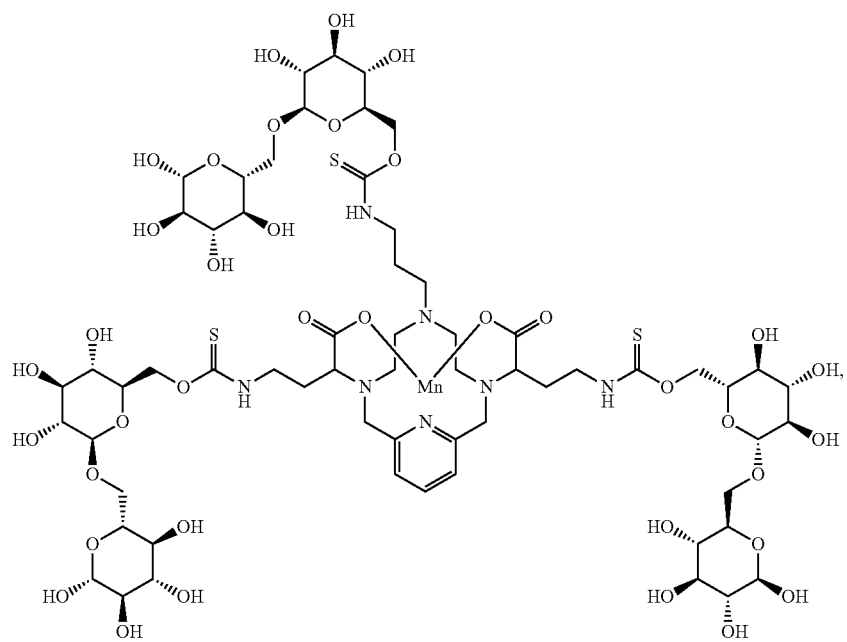

34
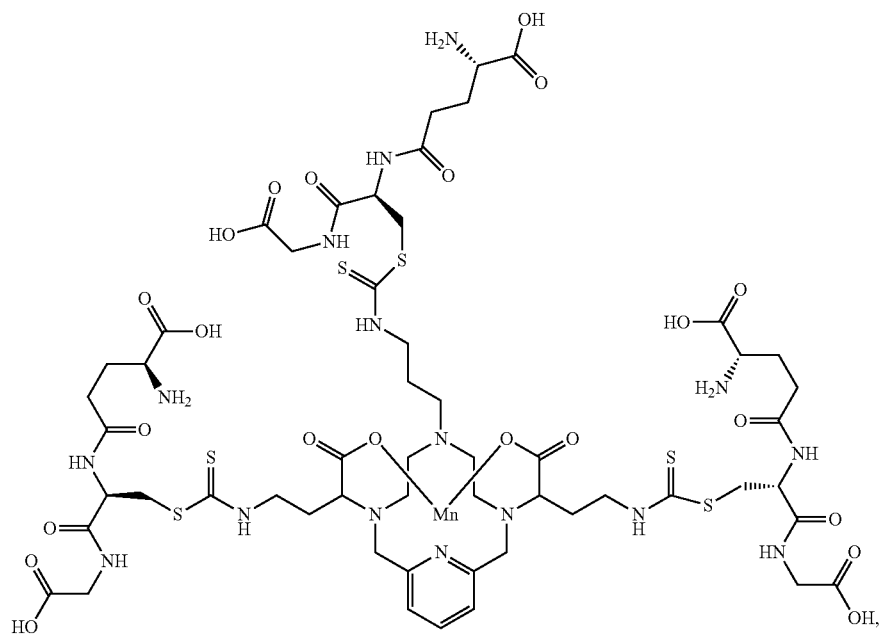
37
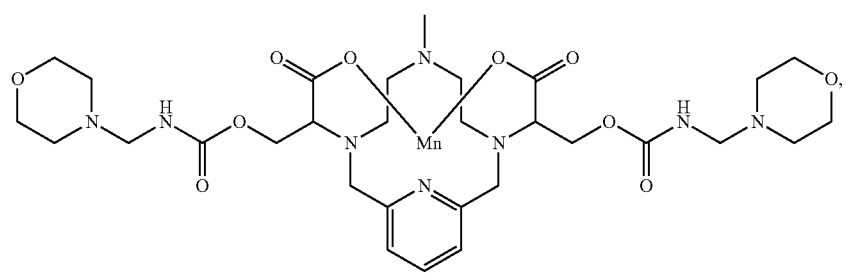
38
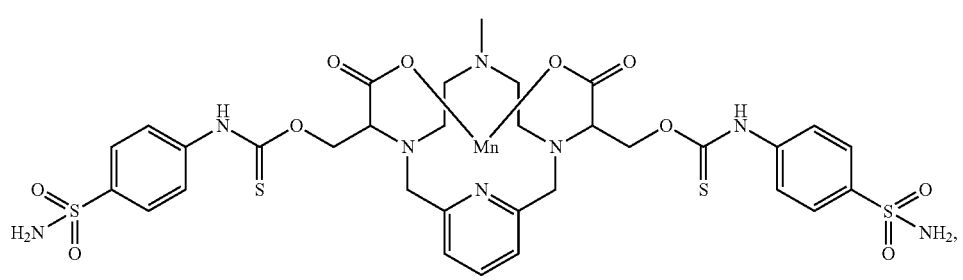
41
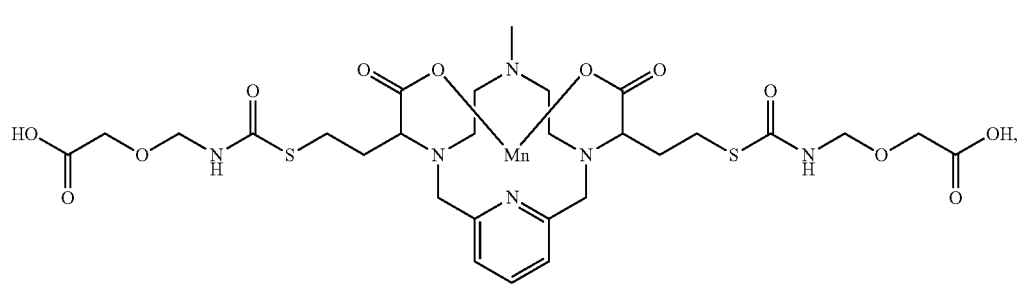

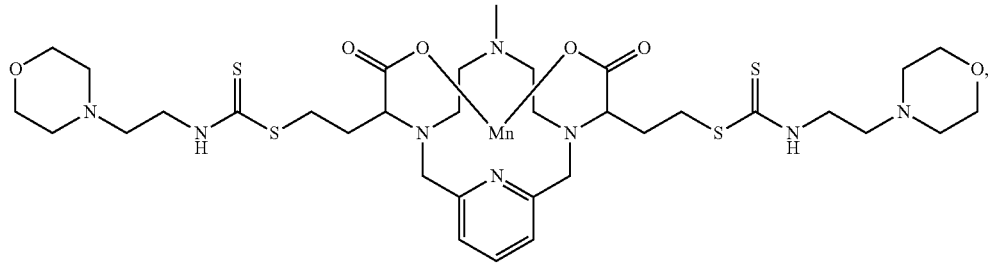

42

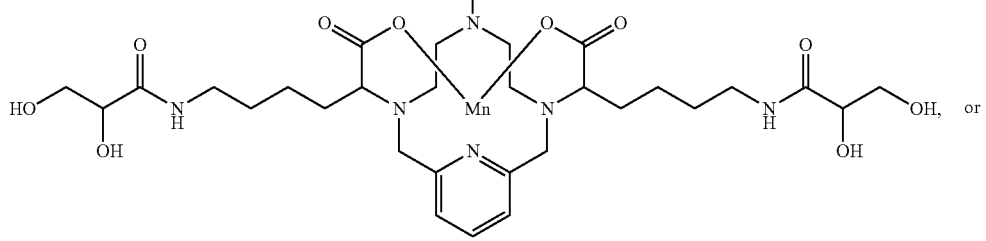

51

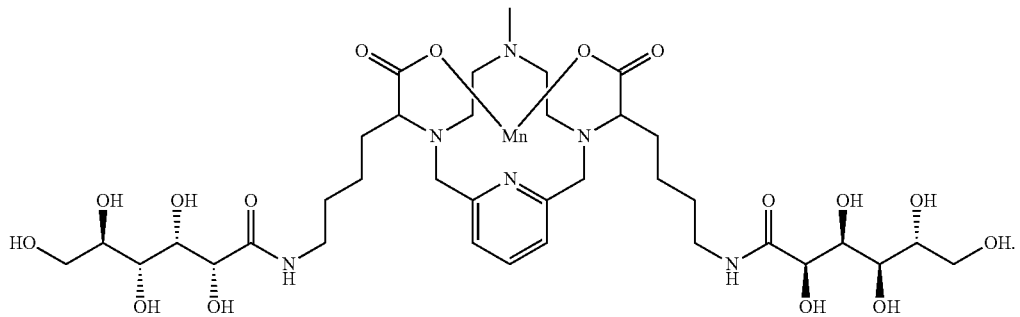

52

24. The compound of Formula I as defined in claim 1 which is either a racemic mixture or diastereomerically pure.

25. A pharmaceutical composition comprising the compound of Formula I as defined in claim 1 together with a biocompatible carrier in a form suitable for mammalian administration.

26. The pharmaceutical composition as defined in claim 25 further comprising one or more pharmaceutically-acceptable excipients.

27. The pharmaceutical composition as defined in claim 26 wherein said pharmaceutically-acceptable excipients are selected from buffering agents, stabilizers, antioxidants, osmolality adjusting agents, pH adjusting agents, excess cheland or weak complexes of physiologically tolerable ions.

28. A method comprising:
(i) administration to a subject of the compound of Formula I as defined in claim 1 or the pharmaceutical composition thereof;
(ii) detection of magnetic resonance (MR) signals from said subject or parts of said subject in which said compound has distributed;
(iii) generation of MR images and/or MR spectra from said detected signals.

29. The compound of Formula I as defined in claim 1 for use in the method as defined in claim 28.

* * * * *